(12) United States Patent
Eugen-Olsen et al.

(10) Patent No.: US 9,645,157 B2
(45) Date of Patent: *May 9, 2017

(54) METHODS OF SELECTING AND TREATING SUBJECTS WITH LOW-GRADE INFLAMMATION AND METABOLIC DISORDERS

(71) Applicant: HVIDOVRE HOSPITAL, Hvidovre (DK)

(72) Inventors: Jesper Eugen-Olsen, Hellerup (DK); Steen B. Haugaard, Frederiksberg (DK); Ove Andersen, Hellerup (DK)

(73) Assignee: Hvidovre Hospital, Hvidovre (DK)

( * ) Notice: Subject to any disclaimer, the term of this patent is extended or adjusted under 35 U.S.C. 154(b) by 202 days.

This patent is subject to a terminal disclaimer.

(21) Appl. No.: 14/312,298

(22) Filed: Jun. 23, 2014

(65) Prior Publication Data

US 2014/0370527 A1    Dec. 18, 2014

Related U.S. Application Data

(62) Division of application No. 12/520,718, filed as application No. PCT/EP2007/064497 on Dec. 21, 2007, now Pat. No. 8,815,519.

(60) Provisional application No. 60/947,074, filed on Jun. 29, 2007, provisional application No. 60/876,838, filed on Dec. 22, 2006.

(30) Foreign Application Priority Data

Dec. 22, 2006 (DK) .................................. 2006 01709
Jun. 29, 2007 (DK) .................................. 2007 00956

(51) Int. Cl.
    *G01N 33/68* (2006.01)
(52) U.S. Cl.
    CPC ............... *G01N 33/6893* (2013.01); *G01N 2333/70596* (2013.01); *G01N 2800/04* (2013.01); *G01N 2800/52* (2013.01); *G01N 2800/7095* (2013.01)

(58) Field of Classification Search
    None
    See application file for complete search history.

(56) References Cited

U.S. PATENT DOCUMENTS

| 6,248,712 B1 | 6/2001 | Danoe | |
| 6,902,884 B1* | 6/2005 | Eugen-Olsen | ... G01N 33/56988 435/215 |
| 8,815,519 B2* | 8/2014 | Eugen-Olsen | ..... G01N 33/6893 435/7.1 |
| 2004/0115190 A1 | 6/2004 | Blasi | |

FOREIGN PATENT DOCUMENTS

| WO | 02058714 | 8/2002 |
| WO | 03031650 | 4/2003 |
| WO | 2005116077 | 12/2005 |

OTHER PUBLICATIONS

Andersen, et al., "Lipodystrophy in human immunodeficiency virus patients impairs insulin action and induces defects in beta-cell function" , Metabolism, 52:1343-1353 (2003).
Andersen, et al., "Soluble urokinase plasminogen activator receptor is a marker of dysmetabolism in HIV-infected patients receiving highly active antiretroviral therapy" , J Med Virol., 80:209-16 (2008).
Better, et al., "*Escherichia coil* secretion of an active chimeric antibody fragment" , Science, 240( 4855):1041-3 (1988).
Bird, et al., "Single-chain antigen-binding proteins" , Science, 242:423-6 (1988).
Cole, et al., "Human monoclonal antibodies" , Mol. Cell Biol., 62:109-120 (1984).
Cote, et al., "Generation of human monoclonal antibodies reactive with cellular antigens" , Proc. Natl. Acad. Sci. USA, 80:2026-2030 (1983).
Danesh, et al., "Low grade inflammation and coronary heart disease: prospective study and updated meta-analytes" , BMJ, 321(7255):199-204 (2000).
De Bock and Wang, "Clinical significance of urokinase-type plasminogen activator receptor (uPAR) expression in cancer" , Med. Res. Rev., 24(1):13-39 (2004).
Emanuela, et al., "Inflammation as a Link between Obesity and Metabolic Syndrome" , J Nutr Metab., 2012:47630 (2012).
Flordellis, et al., "New therapeutic options for the metabolic syndrome: What \s next" , Trends Endocrinol Mertabol., 16(6):254-60 (2005).
Frayn, "Calculation of substrate oxidation rates in vivo from gaseous exchange" , J Appl Physiol., 55:628-634 (1983).
Garcia-Monco, "Soluble urokinase receptor (uPAR, CD 87) is present in serum and cerebrospinal fluid in patients with neurologic disreases" , J Neuroimmunology, 129:216-23 (2002).
Grundy, et al.,"Diagnosis and management of the metabolic syndrome: an American Heart Association/National Heart, Lung, and Blood Institute Scientific Statement" , Circulation, 112:2735-2752 (2005).
Haugaard, et al., "Defective glucose and lipid metabolism in human immunodeficiency virus-infected patients with lipodystrophy involve liver, muscle tissue and pancreatic beta-cells", Eur J Endocrinol, 152:103-112 (2005).

(Continued)

*Primary Examiner* — Ilia Ouspenski
(74) *Attorney, Agent, or Firm* — Pabst Patent Group LLP

(57) ABSTRACT

The invention concerns a marker for low-grade inflammation and metabolic syndrome (MS) and MS-related diseases and/or low-grade inflammation-related diseases such as cardiovascular disease, ischemic heart disease and type 2 diabetes. More particularly it concerns the measurement of the concentration of soluble urokinase plasminogen activator receptor (suPAR) in human biological fluids (sputum, cystic fluid, ascites, serum, plasma, urine) as a tool of diagnosing and/or prognosticating low-grade inflammation and metabolic syndrome and the risk of development of the related diseases such as cancer, cardiovascular disease, ischemic heart disease and type 2 diabetes.

7 Claims, 28 Drawing Sheets

(56) References Cited

OTHER PUBLICATIONS

Hother-Nielsen, et al., "Effects of insulin on glucose turnover rates in vivo: isotope dilution versus constant specific activity technique", Metabolism, 45:82-91 (1996).

Huston, et al., "Protein engineering of antibody binding sites: recovery of specific activity in an anti-digoxin single-chain Fv analogue produced in *Escherichia coli*", Proc. Natl. Acad. Sci. USA, 85:5879 (1988).

Kofoed, et al., "Development and validation of a multiplex add-on assay for sepsis biomarkers using xMAP technology", Clinical Chem., 52(7):1284-93 (2006).

Koh, et al., "Inflamatory markers and the metabolic syndrome", J Am. College Cardiol., 46(11):1978-85 (2005).

Kozbor, et al., "Specific immunoglobulin production and enhanced tumorigenicity following ascites growth of human hybridomas", J. Immunol. Methods, 81:31-42 (1985).

Lihn, et al., "Increased expression of TNF-alpha, IL-6, and IL-8 in HALS: implications for reduced adiponectin expression and plasma levels", Am J Physiol Endocrinol Metab, 285:E1072-E1080 (2003).

Mizukami, et al., "Enzyme-linked immunoabsorbent assay detection of a soluble form of urokinase plasminogen activator receptor in vivo", Blood, 86(1):203-11 (1995).

Mustjoki, et al., "Soluble urokinase receptor levels correlate with number of circulating tumor cells in acute myeloid leukemia and decrease rapidly during chemotherapy", Cancer Res, 60:7126-7132 (2000).

Ostrowski, et al., "High Plasma levels of intact and cleaved soluble urokinase receptor reflect immune activation and are independent predictors off mortality in HIV-1-infected patients", J. Acquir. Immune Defic Syndr., 39(1):23-31 (2005).

Ostrowski, et al., "Plasma levels of intact and cleaved urokinase receptor decrease in HIV-1-infected patients initiating highly active antiretroviral therapy", Scand. J Immunol., 63(6):478-86 (2006).

Ostrowski, et al., "Soluble urokinase receptor levels in plasma during 5 years of highly active antiretroviral therapy in HIV-1-infected patients", J. Acquir. Immune Defic Syndr., 35(4):337-42 (2004).

Sier, et al., "Presence of urokinase-type plasminogen activator receptor in urine of cancer patients and its possible clinical relevance", Lab Invest., 79(6):717-22 (1999).

Skerra, et al., "Assembly of a functional immunoglobulin Fv fragment in *Escherichia coli*", Science, 240(4855):1038-41 (1988).

Sloand, et al. "A role for plasma urokinase plasminogen activator receptor (uPAR) in thrombosis in paroxysmal nocturnal hemoglobinuria (PNH)", Blood, 104(11):84A (2004).

Svendsen, et al., "Preoperative concentrations of suPAR and MBL proteins are associated with the development of pneumonia after elective surgery for colorectal cancer", Surgical Infections, 7(5):463-471 (2006).

Vozarova, et al., "High white blood cell count is associated with a worsening of insulin sensitivity and predicts the development of type 2 diabetes", Diabetes, 51:455-461 (2002).

Ward, et al, "Binding activities of a repertoire of single immunoglobulin variable domains secreted from *Escherichia coli*", Nature, 341:544 (1989).

Winter & Milstein, "Man-made antibodies", Nature, 349:293-299 (1991).

Kasperska-Zajac and Rogala, Circulation levels of urokinase-type plasminogen activator (uPA) and its soluble receptor (suPAR) its patients with atopic eczema dermatitis syndrome, Inflammation, 19(2-3):90-3 (2006).

Slot, et al/ Soluble urokinase plasminogen activator receptor in plasma of patients with inflammatory rheumatic disorders: increased concentrations in rheumatoid arthritis, Am Rheum Dis., 58:488-90 (1999).

Siev, et al., Correlation between serum and plasma antibody titers to mycobacterial antigens, Clin Vaccine Immunol., 18(1):173-5 (2011).

* cited by examiner

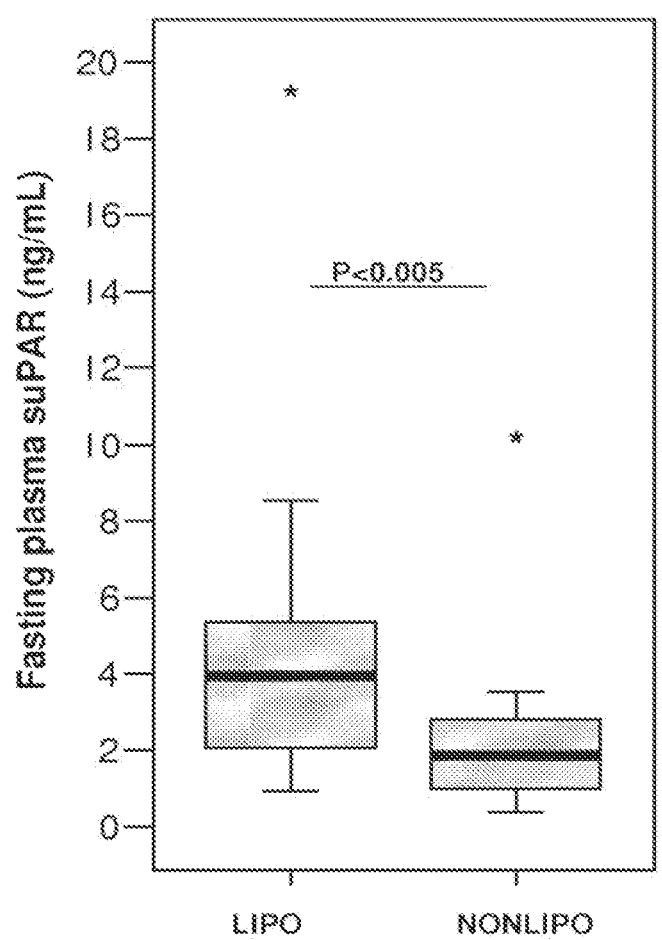

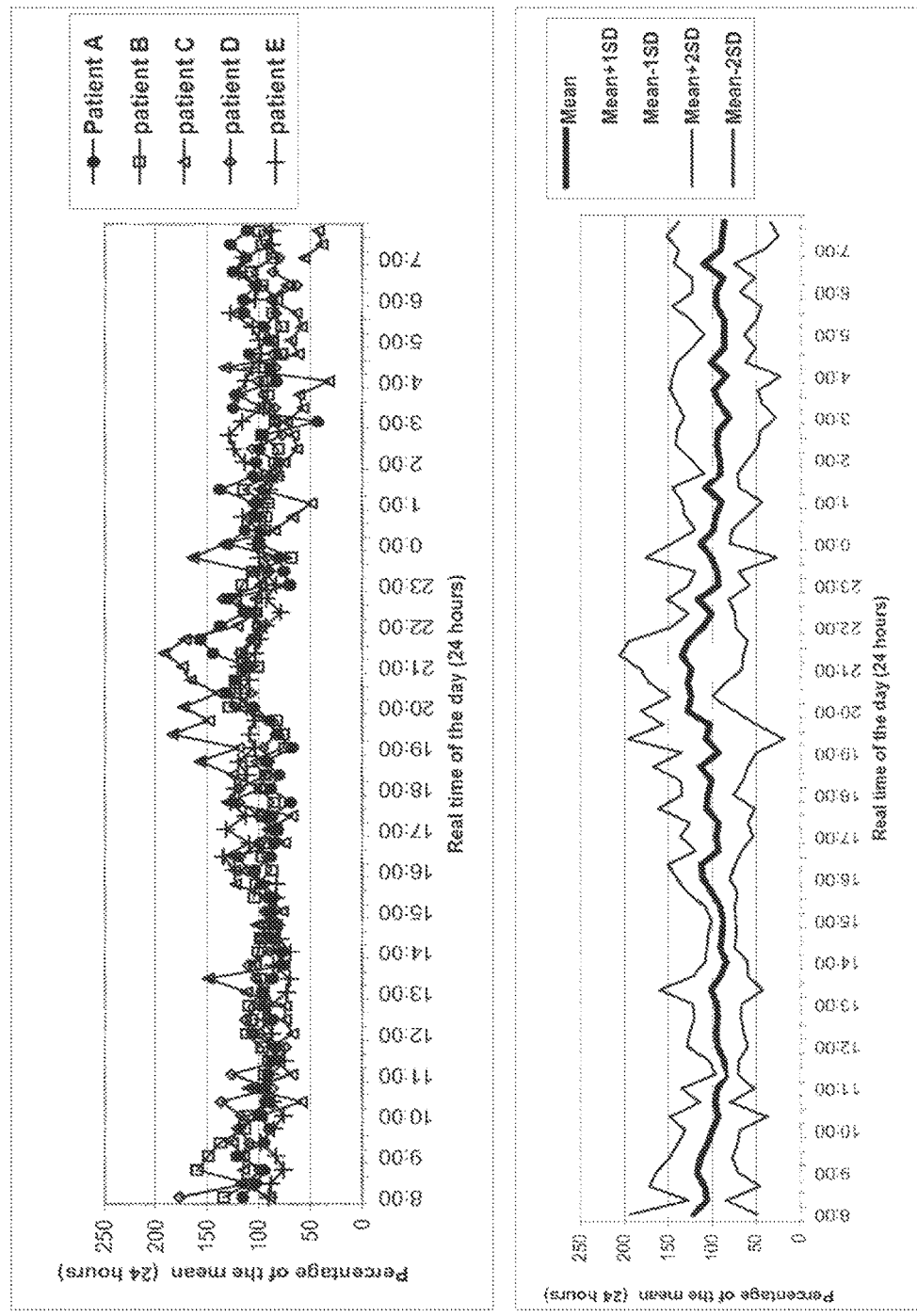
Figure 4. [upper plot and lower plot]

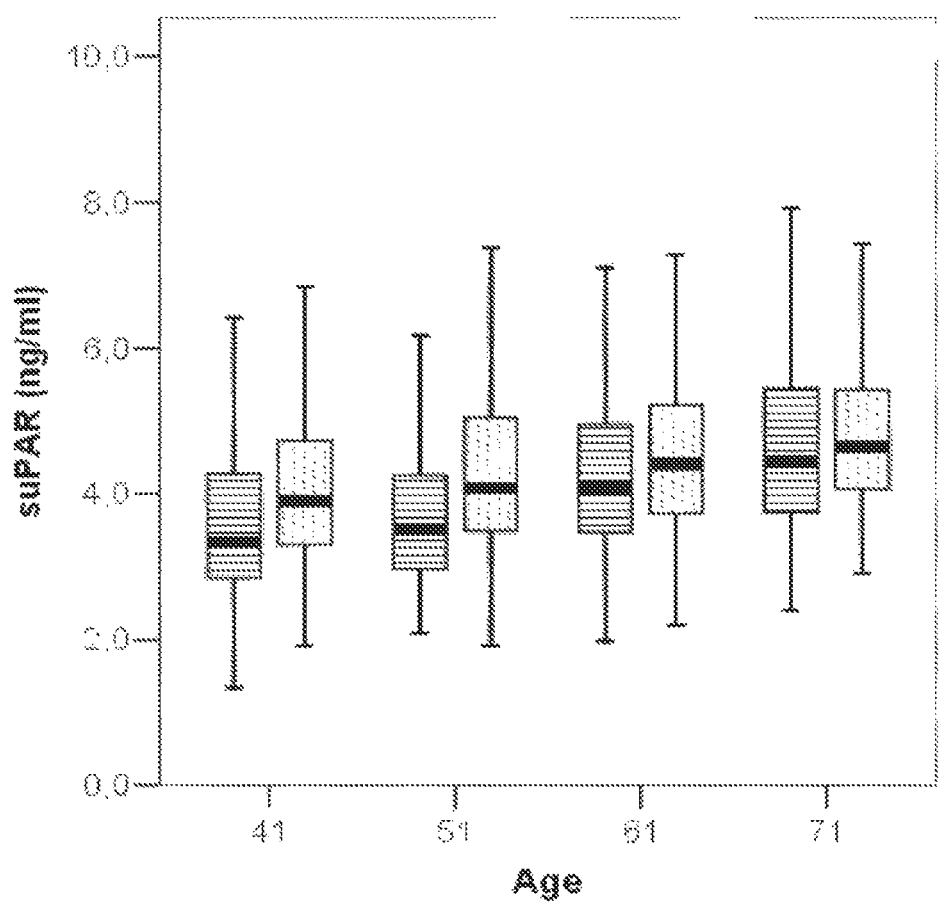

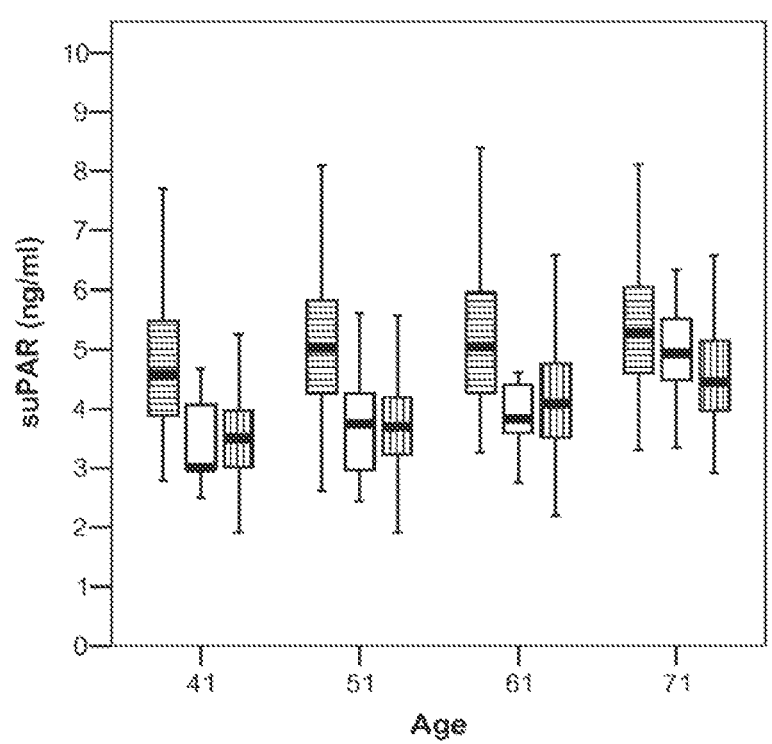

A

B

C

D

E

F

SEQUENCE LISTING

<160> NUMBER OF SEQ ID NOS: 15

<210> SEQ ID NO 1
<211> LENGTH: 301
<212> TYPE: PRT
<213> ORGANISM: homo sapiens

<400> SEQUENCE: 1

Met Gly His Pro Pro Leu Leu Pro Leu Leu Leu Leu His Thr Cys
1               5                   10                  15

Val Pro Ala Ser Trp Gly Leu Arg Cys Met Gln Cys Lys Thr Asn Gly
            20                  25                  30

```
Asp Cys Arg Val Glu Glu Cys Ala Leu Gly Gln Asp Leu Cys Arg Thr
            35                  40                  45

Thr Ile Val Arg Leu Trp Glu Gly Glu Glu Leu Glu Leu Val Glu
 50                  55                  60

Lys Ser Cys Thr His Ser Glu Lys Thr Asn Arg Thr Leu Ser Tyr Arg
 65                  70                  75                  80

Thr Gly Leu Lys Ile Thr Ser Leu Thr Glu Val Val Cys Gly Leu Asp
                 85                  90                  95

Leu Cys Asn Gln Gly Asn Ser Gly Arg Ala Val Thr Tyr Ser Arg Ser
                100                 105                 110

Arg Tyr Leu Glu Cys Ile Ser Cys Gly Ser Ser Asp Met Ser Cys Glu
            115                 120                 125

Arg Gly Arg His Gln Ser Leu Gln Cys Arg Ser Pro Glu Glu Gln Cys
        130                 135                 140

Leu Asp Val Val Thr His Trp Ile Gln Glu Gly Glu Gly Arg Pro
145                 150                 155                 160

Lys Asp Asp Arg Pro Leu Arg Gly Cys Gly Tyr Leu Pro Gly Cys Pro
                165                 170                 175

Gly Ser Asn Gly Phe His Asn Asn Asp Thr Phe His Phe Leu Lys Cys
            180                 185                 190

Cys Asn Thr Thr Lys Cys Asn Glu Gly Pro Ile Leu Glu Leu Glu Asn
        195                 200                 205

Leu Pro Gln Asn Gly Arg Gln Cys Tyr Ser Cys Lys Gly Asn Ser Thr
210                 215                 220

His Gly Cys Ser Ser Glu Glu Thr Phe Leu Ile Asp Cys Arg Gly Pro
225                 230                 235                 240

Met Asn Gln Cys Leu Val Ala Thr Gly Thr His Glu Pro Lys Asn Gln
                245                 250                 255

Ser Tyr Met Val Arg Gly Cys Ala Thr Ala Ser Met Cys Gln His Ala
            260                 265                 270

His Leu Gly Asp Ala Phe Ser Met Asn His Ile Asp Val Ser Cys Cys
        275                 280                 285

Thr Lys Ser Gly Cys Asn His Pro Asp Leu Asp Val Gln
    290                 295                 300

<210> SEQ ID NO 2
<211> LENGTH: 335
<212> TYPE: PRT
<213> ORGANISM: Homo sapiens

<400> SEQUENCE: 2

Met Gly His Pro Pro Leu Leu Pro Leu Leu Leu Leu His Thr Cys
 1               5                  10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
            35                  40                  45

Thr Ile Val Arg Leu Trp Glu Glu Gly Glu Glu Leu Glu Leu Val Glu
 50                  55                  60

Lys Ser Cys Thr His Ser Glu Lys Thr Asn Arg Thr Leu Ser Tyr Arg
 65                  70                  75                  80

Thr Gly Leu Lys Ile Thr Ser Leu Thr Glu Val Val Cys Gly Leu Asp
                 85                  90                  95

Leu Cys Asn Gln Gly Asn Ser Gly Arg Ala Val Thr Tyr Ser Arg Ser
```

```
            100                 105                 110
Arg Tyr Leu Glu Cys Ile Ser Cys Gly Ser Ser Asp Met Ser Cys Glu
            115                 120                 125
Arg Gly Arg His Gln Ser Leu Gln Cys Arg Ser Pro Glu Glu Gln Cys
            130                 135                 140
Leu Asp Val Val Thr His Trp Ile Gln Glu Gly Glu Glu Gly Arg Pro
145                 150                 155                 160
Lys Asp Asp Arg His Leu Arg Gly Cys Gly Tyr Leu Pro Gly Cys Pro
                165                 170                 175
Gly Ser Asn Gly Phe His Asn Asn Asp Thr Phe His Phe Leu Lys Cys
                180                 185                 190
Cys Asn Thr Thr Lys Cys Asn Glu Gly Pro Ile Leu Glu Leu Glu Asn
                195                 200                 205
Leu Pro Gln Asn Gly Arg Gln Cys Tyr Ser Cys Lys Gly Asn Ser Thr
            210                 215                 220
His Gly Cys Ser Ser Glu Glu Thr Phe Leu Ile Asp Cys Arg Gly Pro
225                 230                 235                 240
Met Asn Gln Cys Leu Val Ala Thr Gly Thr His Glu Pro Lys Asn Gln
                245                 250                 255
Ser Tyr Met Val Arg Gly Cys Ala Thr Ala Ser Met Cys Gln His Ala
                260                 265                 270
His Leu Gly Asp Ala Phe Ser Met Asn His Ile Asp Val Ser Cys Cys
                275                 280                 285
Thr Lys Ser Gly Cys Asn His Pro Asp Leu Asp Val Gln Tyr Arg Ser
            290                 295                 300
Gly Ala Ala Pro Gln Pro Gly Pro Ala His Leu Ser Leu Thr Ile Thr
305                 310                 315                 320
Leu Leu Met Thr Ala Arg Leu Trp Gly Gly Thr Leu Leu Trp Thr
                325                 330                 335

<210> SEQ ID NO 3
<211> LENGTH: 335
<212> TYPE: PRT
<213> ORGANISM: Homo sapiens

<400> SEQUENCE: 3

Met Gly His Pro Pro Leu Leu Pro Leu Leu Leu Leu His Thr Cys
1               5                   10                  15
Val Pro Ala Ser Trp Gly Leu Arg Cys Met Gln Cys Lys Thr Asn Gly
            20                  25                  30
Asp Cys Arg Val Glu Glu Cys Ala Leu Gly Gln Asp Leu Cys Arg Thr
            35                  40                  45
Thr Ile Val Arg Leu Trp Glu Glu Gly Glu Leu Glu Leu Val Glu
        50                  55                  60
Lys Ser Cys Thr His Ser Glu Lys Thr Asn Arg Thr Leu Ser Tyr Arg
65                  70                  75                  80
Thr Gly Leu Lys Ile Thr Ser Leu Thr Glu Val Val Cys Gly Leu Asp
                85                  90                  95
Leu Cys Asn Gln Gly Asn Ser Gly Arg Ala Val Thr Tyr Ser Arg Ser
            100                 105                 110
Arg Tyr Leu Glu Cys Ile Ser Cys Gly Ser Ser Asp Met Ser Cys Glu
            115                 120                 125
Arg Gly Arg His Gln Ser Leu Gln Cys Arg Ser Pro Glu Glu Gln Cys
            130                 135                 140
```

```
Leu Asp Val Val Thr His Trp Ile Gln Glu Gly Glu Glu Gly Arg Pro
145                 150                 155                 160

Lys Asp Asp Arg His Leu Arg Gly Cys Gly Tyr Leu Pro Gly Cys Pro
                165                 170                 175

Gly Ser Asn Gly Phe His Asn Asn Asp Thr Phe His Phe Leu Lys Cys
            180                 185                 190

Cys Asn Thr Thr Lys Cys Asn Glu Gly Pro Ile Leu Glu Leu Glu Asn
        195                 200                 205

Leu Pro Gln Asn Gly Arg Gln Cys Tyr Ser Cys Lys Gly Asn Ser Thr
    210                 215                 220

His Gly Cys Ser Ser Glu Glu Thr Phe Leu Ile Asp Cys Arg Gly Pro
225                 230                 235                 240

Met Asn Gln Cys Leu Val Ala Thr Gly Thr His Glu Pro Lys Asn Gln
                245                 250                 255

Ser Tyr Met Val Arg Gly Cys Ala Thr Ala Ser Met Cys Gln His Ala
            260                 265                 270

His Leu Gly Asp Ala Phe Ser Met Asn His Ile Asp Val Ser Cys Cys
        275                 280                 285

Thr Lys Ser Gly Cys Asn His Pro Asp Leu Asp Val Gln Tyr Arg Ser
    290                 295                 300

Gly Ala Ala Pro Gln Pro Gly Pro Ala His Leu Ser Leu Thr Ile Thr
305                 310                 315                 320

Leu Leu Met Thr Ala Arg Leu Trp Gly Gly Thr Leu Leu Trp Thr
                325                 330                 335

<210> SEQ ID NO 4
<211> LENGTH: 281
<212> TYPE: PRT
<213> ORGANISM: Homo sapiens

<400> SEQUENCE: 4

Met Gly His Pro Pro Leu Leu Pro Leu Leu Leu Leu His Thr Cys
1               5                   10                  15

Val Pro Ala Ser Trp Gly Leu Arg Cys Met Gln Cys Lys Thr Asn Gly
            20                  25                  30

Asp Cys Arg Val Glu Glu Cys Ala Leu Gly Gln Asp Leu Cys Arg Thr
        35                  40                  45

Thr Ile Val Arg Leu Trp Glu Glu Gly Glu Glu Leu Glu Leu Val Glu
    50                  55                  60

Lys Ser Cys Thr His Ser Glu Lys Thr Asn Arg Thr Leu Ser Tyr Arg
65                  70                  75                  80

Thr Gly Leu Lys Ile Thr Ser Leu Thr Glu Val Val Cys Gly Leu Asp
                85                  90                  95

Leu Cys Asn Gln Gly Asn Ser Gly Arg Ala Val Thr Tyr Ser Arg Ser
            100                 105                 110

Arg Tyr Leu Glu Cys Ile Ser Cys Gly Ser Ser Asp Met Ser Cys Glu
        115                 120                 125

Arg Gly Arg His Gln Ser Leu Gln Cys Arg Ser Pro Glu Glu Gln Cys
    130                 135                 140

Leu Asp Val Val Thr His Trp Ile Gln Glu Gly Glu Glu Gly Arg Pro
145                 150                 155                 160

Lys Asp Asp Arg His Leu Arg Gly Cys Gly Tyr Leu Pro Gly Cys Pro
                165                 170                 175

Gly Ser Asn Gly Phe His Asn Asn Asp Thr Phe His Phe Leu Lys Cys
            180                 185                 190
```

```
Cys Asn Thr Thr Lys Cys Asn Glu Gly Pro Ile Leu Glu Leu Glu Asn
            195                 200                 205

Leu Pro Gln Asn Gly Arg Gln Cys Tyr Ser Cys Lys Gly Asn Ser Thr
210                 215                 220

His Gly Cys Ser Ser Glu Glu Thr Phe Leu Ile Asp Cys Arg Gly Pro
225                 230                 235                 240

Met Asn Gln Cys Leu Val Ala Thr Gly Thr His Glu Arg Ser Leu Trp
            245                 250                 255

Gly Ser Trp Leu Pro Cys Lys Ser Thr Thr Ala Leu Arg Pro Pro Cys
            260                 265                 270

Cys Glu Glu Ala Gln Ala Thr His Val
            275                 280

<210> SEQ ID NO 5
<211> LENGTH: 279
<212> TYPE: PRT
<213> ORGANISM: Homo sapiens

<400> SEQUENCE: 5

Leu Arg Cys Met Gln Cys Lys Thr Asn Gly Asp Cys Arg Val Glu Glu
1               5                   10                  15

Cys Ala Leu Gly Gln Asp Leu Cys Arg Thr Thr Ile Val Arg Leu Trp
            20                  25                  30

Glu Glu Gly Glu Glu Leu Glu Leu Val Glu Lys Ser Cys Thr His Ser
        35                  40                  45

Glu Lys Thr Asn Arg Thr Leu Ser Tyr Arg Thr Gly Leu Lys Ile Thr
    50                  55                  60

Ser Leu Thr Glu Val Val Cys Gly Leu Asp Leu Cys Asn Gln Gly Asn
65                  70                  75                  80

Ser Gly Arg Ala Val Thr Tyr Ser Arg Ser Arg Tyr Leu Glu Cys Ile
                85                  90                  95

Ser Cys Gly Ser Ser Asp Met Ser Cys Glu Arg Gly Arg His Gln Ser
            100                 105                 110

Leu Gln Cys Arg Ser Pro Glu Glu Gln Cys Leu Asp Val Val Thr His
        115                 120                 125

Trp Ile Gln Glu Gly Glu Glu Gly Arg Pro Lys Asp Asp Arg Pro Leu
130                 135                 140

Arg Gly Cys Gly Tyr Leu Pro Gly Cys Pro Gly Ser Asn Gly Phe His
145                 150                 155                 160

Asn Asn Asp Thr Phe His Phe Leu Lys Cys Cys Asn Thr Thr Lys Cys
                165                 170                 175

Asn Glu Gly Pro Ile Leu Glu Leu Glu Asn Leu Pro Gln Asn Gly Arg
            180                 185                 190

Gln Cys Tyr Ser Cys Lys Gly Asn Ser Thr His Gly Cys Ser Ser Glu
        195                 200                 205

Glu Thr Phe Leu Ile Asp Cys Arg Gly Pro Met Asn Gln Cys Leu Val
    210                 215                 220

Ala Thr Gly Thr His Glu Pro Lys Asn Gln Ser Tyr Met Val Arg Gly
225                 230                 235                 240

Cys Ala Thr Ala Ser Met Cys Gln His Ala His Leu Gly Asp Ala Phe
                245                 250                 255

Ser Met Asn His Ile Asp Val Ser Cys Cys Thr Lys Ser Gly Cys Asn
            260                 265                 270

His Pro Asp Leu Asp Val Gln
```

-continued

275

<210> SEQ ID NO 6
<211> LENGTH: 83
<212> TYPE: PRT
<213> ORGANISM: Homo sapiens

<400> SEQUENCE: 6

Leu Arg Cys Met Gln Cys Lys Thr Asn Gly Asp Cys Arg Val Glu Glu
1               5                   10                  15

Cys Ala Leu Gly Gln Asp Leu Cys Arg Thr Thr Ile Val Arg Leu Trp
            20                  25                  30

Glu Glu Gly Glu Glu Leu Glu Leu Val Glu Lys Ser Cys Thr His Ser
        35                  40                  45

Glu Lys Thr Asn Arg Thr Leu Ser Tyr Arg Thr Gly Leu Lys Ile Thr
    50                  55                  60

Ser Leu Thr Glu Val Val Cys Gly Leu Asp Leu Cys Asn Gln Gly Asn
65                  70                  75                  80

Ser Gly Arg

<210> SEQ ID NO 7
<211> LENGTH: 196
<212> TYPE: PRT
<213> ORGANISM: Homo sapiens

<400> SEQUENCE: 7

Ala Val Thr Tyr Ser Arg Ser Arg Tyr Leu Glu Cys Ile Ser Cys Gly
1               5                   10                  15

Ser Ser Asp Met Ser Cys Glu Arg Gly Arg His Gln Ser Leu Gln Cys
            20                  25                  30

Arg Ser Pro Glu Glu Gln Cys Leu Asp Val Val Thr His Trp Ile Gln
        35                  40                  45

Glu Gly Glu Gly Arg Pro Lys Asp Arg Pro Leu Arg Gly Cys
    50                  55                  60

Gly Tyr Leu Pro Gly Cys Pro Gly Ser Asn Gly Phe His Asn Asn Asp
65                  70                  75                  80

Thr Phe His Phe Leu Lys Cys Cys Asn Thr Thr Lys Cys Asn Glu Gly
            85                  90                  95

Pro Ile Leu Glu Leu Glu Asn Leu Pro Gln Asn Gly Arg Gln Cys Tyr
        100                 105                 110

Ser Cys Lys Gly Asn Ser Thr His Gly Cys Ser Ser Glu Glu Thr Phe
    115                 120                 125

Leu Ile Asp Cys Arg Gly Pro Met Asn Gln Cys Leu Val Ala Thr Gly
130                 135                 140

Thr His Glu Pro Lys Asn Gln Ser Tyr Met Val Arg Gly Cys Ala Thr
145                 150                 155                 160

Ala Ser Met Cys Gln His Ala His Leu Gly Asp Ala Phe Ser Met Asn
            165                 170                 175

His Ile Asp Val Ser Cys Cys Thr Lys Ser Gly Cys Asn His Pro Asp
        180                 185                 190

Leu Asp Val Gln
    195

<210> SEQ ID NO 8
<211> LENGTH: 87
<212> TYPE: PRT
<213> ORGANISM: Homo sapiens

```
<400> SEQUENCE: 8

Leu Arg Cys Met Gln Cys Lys Thr Asn Gly Asp Cys Arg Val Glu Glu
1               5                   10                  15

Cys Ala Leu Gly Gln Asp Leu Cys Arg Thr Thr Ile Val Arg Leu Trp
                20                  25                  30

Glu Glu Gly Glu Glu Leu Val Glu Lys Ser Cys Thr His Ser
            35                  40                  45

Glu Lys Thr Asn Arg Thr Leu Ser Tyr Arg Thr Gly Leu Lys Ile Thr
    50                  55                  60

Ser Leu Thr Glu Val Val Cys Gly Leu Asp Leu Cys Asn Gln Gly Asn
65                  70                  75                  80

Ser Gly Arg Ala Val Thr Tyr
                85

<210> SEQ ID NO 9
<211> LENGTH: 192
<212> TYPE: PRT
<213> ORGANISM: Homo sapiens

<400> SEQUENCE: 9

Ser Arg Ser Arg Tyr Leu Glu Cys Ile Ser Cys Gly Ser Ser Asp Met
1               5                   10                  15

Ser Cys Glu Arg Gly Arg His Gln Ser Leu Gln Cys Arg Ser Pro Glu
                20                  25                  30

Glu Gln Cys Leu Asp Val Val Thr His Trp Ile Gln Glu Gly Glu Glu
            35                  40                  45

Gly Arg Pro Lys Asp Asp Arg Pro Leu Arg Gly Cys Gly Tyr Leu Pro
    50                  55                  60

Gly Cys Pro Gly Ser Asn Gly Phe His Asn Asn Asp Thr Phe His Phe
65                  70                  75                  80

Leu Lys Cys Cys Asn Thr Thr Lys Cys Asn Glu Gly Pro Ile Leu Glu
                85                  90                  95

Leu Glu Asn Leu Pro Gln Asn Gly Arg Gln Cys Tyr Ser Cys Lys Gly
                100                 105                 110

Asn Ser Thr His Gly Cys Ser Ser Glu Glu Thr Phe Leu Ile Asp Cys
            115                 120                 125

Arg Gly Pro Met Asn Gln Cys Leu Val Ala Thr Gly Thr His Glu Pro
    130                 135                 140

Lys Asn Gln Ser Tyr Met Val Arg Gly Cys Ala Thr Ala Ser Met Cys
145                 150                 155                 160

Gln His Ala His Leu Gly Asp Ala Phe Ser Met Asn His Ile Asp Val
                165                 170                 175

Ser Cys Cys Thr Lys Ser Gly Cys Asn His Pro Asp Leu Asp Val Gln
                180                 185                 190

<210> SEQ ID NO 10
<211> LENGTH: 89
<212> TYPE: PRT
<213> ORGANISM: Homo sapiens

<400> SEQUENCE: 10

Leu Arg Cys Met Gln Cys Lys Thr Asn Gly Asp Cys Arg Val Glu Glu
1               5                   10                  15

Cys Ala Leu Gly Gln Asp Leu Cys Arg Thr Thr Ile Val Arg Leu Trp
                20                  25                  30
```

Glu Glu Gly Glu Leu Glu Leu Val Glu Lys Ser Cys Thr His Ser
         35                  40                  45

Glu Lys Thr Asn Arg Thr Leu Ser Tyr Arg Thr Gly Leu Lys Ile Thr
 50                  55                  60

Ser Leu Thr Glu Val Val Cys Gly Leu Asp Leu Cys Asn Gln Gly Asn
 65                  70                  75                  80

Ser Gly Arg Ala Val Thr Tyr Ser Arg
                 85

<210> SEQ ID NO 11
<211> LENGTH: 190
<212> TYPE: PRT
<213> ORGANISM: Homo sapiens

<400> SEQUENCE: 11

Ser Arg Tyr Leu Glu Cys Ile Ser Cys Gly Ser Ser Asp Met Ser Cys
 1               5                  10                  15

Glu Arg Gly Arg His Gln Ser Leu Gln Cys Arg Ser Pro Glu Glu Gln
             20                  25                  30

Cys Leu Asp Val Val Thr His Trp Ile Gln Glu Gly Glu Glu Gly Arg
         35                  40                  45

Pro Lys Asp Asp Arg Pro Leu Arg Gly Cys Gly Tyr Leu Pro Gly Cys
 50                  55                  60

Pro Gly Ser Asn Gly Phe His Asn Asn Asp Thr Phe His Phe Leu Lys
 65                  70                  75                  80

Cys Cys Asn Thr Thr Lys Cys Asn Glu Gly Pro Ile Leu Glu Leu Glu
             85                  90                  95

Asn Leu Pro Gln Asn Gly Arg Gln Cys Tyr Ser Cys Lys Gly Asn Ser
            100                 105                 110

Thr His Gly Cys Ser Ser Glu Gly Thr Phe Leu Ile Asp Cys Arg Gly
            115                 120                 125

Pro Met Asn Gln Cys Leu Val Ala Thr Gly Thr His Glu Pro Lys Asn
130                 135                 140

Gln Ser Tyr Met Val Arg Gly Cys Ala Thr Ala Ser Met Cys Gln His
145                 150                 155                 160

Ala His Leu Gly Asp Ala Phe Ser Met Asn His Ile Asp Val Ser Cys
                165                 170                 175

Cys Thr Lys Ser Gly Cys Asn His Pro Asp Leu Asp Val Gln
            180                 185                 190

<210> SEQ ID NO 12
<211> LENGTH: 91
<212> TYPE: PRT
<213> ORGANISM: Homo sapiens

<400> SEQUENCE: 12

Leu Arg Cys Met Gln Cys Lys Thr Asn Gly Asp Cys Arg Val Glu Glu
 1               5                  10                  15

Cys Ala Leu Gly Gln Asp Leu Cys Arg Thr Thr Ile Val Arg Leu Trp
             20                  25                  30

Glu Glu Gly Glu Glu Leu Glu Leu Val Glu Lys Ser Cys Thr His Ser
         35                  40                  45

Glu Lys Thr Asn Arg Thr Leu Ser Tyr Arg Thr Gly Leu Lys Ile Thr
 50                  55                  60

Ser Leu Thr Glu Val Val Cys Gly Leu Asp Leu Cys Asn Gln Gly Asn
 65                  70                  75                  80

```
Ser Gly Arg Ala Val Thr Tyr Ser Arg Ser Arg
                85                  90

<210> SEQ ID NO 13
<211> LENGTH: 188
<212> TYPE: PRT
<213> ORGANISM: Homo sapiens

<400> SEQUENCE: 13

Tyr Leu Glu Cys Ile Ser Cys Gly Ser Ser Asp Met Ser Cys Glu Arg
1               5                   10                  15

Gly Arg His Gln Ser Leu Gln Cys Arg Ser Pro Glu Glu Gln Cys Leu
            20                  25                  30

Asp Val Val Thr His Trp Ile Gln Glu Gly Glu Glu Gly Arg Pro Lys
        35                  40                  45

Asp Asp Arg Pro Leu Arg Gly Cys Gly Tyr Leu Pro Gly Cys Pro Gly
    50                  55                  60

Ser Asn Gly Phe His Asn Asn Asp Thr Phe His Phe Leu Lys Cys Cys
65                  70                  75                  80

Asn Thr Thr Lys Cys Asn Glu Gly Pro Ile Leu Glu Leu Glu Asn Leu
                85                  90                  95

Pro Gln Asn Gly Arg Gln Cys Tyr Ser Cys Lys Gly Asn Ser Thr His
            100                 105                 110

Gly Cys Ser Ser Glu Glu Thr Phe Leu Ile Asp Cys Arg Gly Pro Met
        115                 120                 125

Asn Gln Cys Leu Val Ala Thr Gly Thr His Glu Pro Lys Asn Gln Ser
    130                 135                 140

Tyr Met Val Arg Gly Cys Ala Thr Ala Ser Met Cys Gln His Ala His
145                 150                 155                 160

Leu Gly Asp Ala Phe Ser Met Asn His Ile Asp Val Ser Cys Cys Thr
                165                 170                 175

Lys Ser Gly Cys Asn His Pro Asp Leu Asp Val Gln
            180                 185

<210> SEQ ID NO 14
<211> LENGTH: 5
<212> TYPE: PRT
<213> ORGANISM: Homo sapiens

<400> SEQUENCE: 14

Ser Arg Ser Arg Tyr
1               5

<210> SEQ ID NO 15
<211> LENGTH: 9
<212> TYPE: PRT
<213> ORGANISM: Homo sapiens

<400> SEQUENCE: 15

Ala Thr Val Tyr Ser Arg Ser Arg Tyr
1               5
```

METHODS OF SELECTING AND TREATING SUBJECTS WITH LOW-GRADE INFLAMMATION AND METABOLIC DISORDERS

CROSS-REFERENCE TO RELATED APPLICATIONS

This application is a divisional of copending application Ser. No. 12/520,718, filed Nov. 17, 2009, which is the National Stage of International Application No. PCT/EP2007/064497, filed Dec. 21, 2007, which claims benefit of Denmark Application No. PA 2007 00956, filed Jun. 29, 2007, U.S. Provisional Application No. 60/947,074, filed Jun. 29, 2007, Denmark Application No. PA 2006 01709, filed Dec. 22, 2006, and U.S. Provisional Application No. 60/876,838, filed Dec. 22, 2006. application Ser. No. 12/520,718, filed Nov. 17, 2009, Application No. PCT/EP2007/064497, filed Dec. 21, 2007, Denmark Application No. PA 2007 00956 filed Jun. 29, 2007, Application No. 60/947,074, filed Jun. 29, 2007, Denmark Application No. PA 2006 01709, filed Dec. 22, 2006, and Application No. 60/876,838, filed Dec. 22, 2006, are hereby incorporated herein by reference in their entirety.

REFERENCE TO SEQUENCE LISTING

The Sequence Listing submitted Jun. 23, 2014 as a text file named "VIRBI_P42672_DIV_ST25.txt," created on Jun. 23, 2014, and having a size of 24,053 bytes is hereby incorporated by reference pursuant to 37 C.F.R. §1.52(e)(5).

FIELD OF THE INVENTION

The invention is directed to methods, computers and computer readable media for detecting and predicting the risk of occurrence of, as well as monitoring the progression of treatment of low-grade inflammation and/or metabolic syndrome. The invention is further directed to methods and compositions for treatment of low-grade inflammation and/or metabolic syndrome. Further, the invention is directed to methods, computers and computer readable media for detecting and predicting the risk of occurrence of cancer and/or mortality within 10 years.

BACKGROUND OF THE INVENTION

Metabolic syndrome is characterized by a combination of high blood pressure, insulin resistance with increased glucose production and decreased glucose utilization, central (abdominal) obesity, dyslipidemia (namely elevated triglycerides and reduced high-density lipoprotein cholesterol), and increased IL-6 and TN-α production.

Metabolic syndrome has emerged as an important cluster of risk factors for development of atherosclerotic diseases, e.g. prevalent and incident atherothrombotic cardiovascular disease (CVD), coronary heart disease, (CHD), stroke, peripheral arterial disease, chronic obstructive lung disease, as well as type 2 diabetes. Stimuli such as over-nutrition, physical inactivity and ageing may result in cytokine hypersecretion and eventually lead to insulin resistance and diabetes in some, but not all, human subjects. According to the clinical criteria developed by the Adult Treatment Panel III (ATP III) Guidelines, it is estimated that 1 out of 4 adults living in the United States merits the diagnosis of metabolic syndrome; however, not all obese individuals develop this syndrome. Cardiovascular disease and Type 2 diabetes are leading causes of death and illness in developed countries, and these chronic diseases are becoming a dominating health problem worldwide. Early diagnosis of metabolic syndrome and prediction of early diagnosis of future cardiovascular events and diabetes would greatly improve the chances of successful prophylactic and therapeutic treatment.

Low-grade inflammation is a triggering factor of metabolic syndrome. Currently, blood levels of pro-inflammatory cytokines, hypersensitive C-reactive protein (hs-CRP), interleukin 6 (IL-6), tumor necrosis factor alpha (TNF-α), serum amyloid A (SAA), fibrinogen and albumin; plasma viscosity; erythrocyte sedimentation rate (ESR); and leukocyte count are used to indicate the presence of low-grade inflammation and thereby predict the risk of developing metabolic syndrome, associated with vascular risk factors and with prevalent and incident atherothrombotic cardiovascular disease (CVD), coronary heart disease (CHD), stroke, peripheral arterial disease, chronic obstructive lung disease and type 2 diabetes.

Although apparently healthy individuals develop metabolic syndrome, it has, in recent years, become evident that HIV-infected individuals on treatment can also develop metabolic syndrome. The widespread implementation of Highly Active Anti-Retroviral Therapy (HAART) in western countries, from 1996 onwards, has increased the prevalence of long-living HIV-infected patients with suppressed HIV RNA and fairly high CD4 counts. However, adverse effects of HAART, in particular the administration of protease inhibitors, lead to a form of Metabolic Syndrome, similar to that observed in non-HIV infected obese individuals, including insulin resistance, fat redistribution, dyslipidemia and other risk factors of cardiovascular disease. There is thus a need to develop early diagnostic and predictive tools to prevent an increase in the morbidity and mortality of HIV-infected patients on HAART who display this cluster of dysmetabolic phenotypes. An individual's immunological status impacts his/her metabolic status, which is reflected in the level of immunological markers, e.g. TNF-α and IL-6. Such immunological markers have been shown to correlate inversely with symptoms of metabolic syndrome in HIV-infected patients as well as in HIV-negative subjects; however, data are not consistent and more stable and stronger predictive markers are needed.

Urokinase-type Plasminogen Activator Receptor (uPAR, CD87) is the cellular receptor for urokinase (uPA), and is expressed by most leukocytes, including monocytes, macrophages, neutrophils and platelets. uPAR is an activation antigen in monocytes and T cells. uPAR may be shed from the cell surface, generating a soluble form of the receptor (suPAR) lacking the GPI-anchor. The shedding mechanism is poorly understood but may occur by cleavage of the GPI-anchor catalyzed by a GPI-specific phospholipase D. Soluble forms of uPAR (suPAR) have been identified in cell culture supernatants and in diverse biological fluids such as tumor ascites, cystic fluid, serum, plasma and urine. The cellular origin of circulating suPAR is not known. Many, if not all, cells which express uPAR also shed soluble forms of the receptor when cultured in vitro.

Svendsen et al (2006) *Surgical Infections* 7, 463-471 disclosed that elevated preoperative concentrations of suPAR were associated with the development of pneumonia following surgery for colorectal cancer.

WO 2005/116077 disclosed the use of a ligand that binds to a binary uPA-uPAR complex, but which does not inhibit uPA-uPAR binding, in the treatment of a large number of diseases, including various cancers and cardiovascular diseases (such as atherosclerosis).

SUMMARY OF THE INVENTION

The invention provides a method for diagnosing low-grade inflammation and/or metabolic syndrome in a mammalian subject, particularly, a human subject, comprising:
   (a) performing an in vitro measurement of the level of a marker in the form of soluble urokinase plasminogen activator receptor (suPAR), and
   (b) using the one or more measurement values obtained as a factor in the diagnosis of low-grade inflammation and/or metabolic syndrome.

The measurement in step (b) may furthermore be compared with a reference value wherein an increase in the level of said marker indicates the grade of low-grade inflammation. In all embodiments of the invention, it is preferable for the mammalian subject not to have been given a blood transfusion in the 24 hours (more preferably, 48 hours or one week) preceding the taking of the sample for the in vitro measurement of suPAR level.

In a particular embodiment, the invention is directed to a method for detecting the level of low-grade inflammation in a mammalian subject comprising:
   (a) isolating a sample from a subject;
   (b) measuring the level of a marker in the form of (i) soluble urokinase plasminogen activator receptor (suPAR), and/or (ii) D2D3 cleavage products of suPAR in said sample of (a);
   (c) comparing the measurement obtained in step (b) with a reference value, wherein an increase in the level of said marker in said sample indicates the degree of low-grade inflammation.

The subject, in a specific embodiment, may be a human subject. The sample from step (a) may undergo processing before step (b) is carried out. For example, it might be frozen and thawed, diluted, concentrated, stabilised, filtered or treated with preservative.

The reference value is a standard of levels of a marker in the form of (i) soluble urokinase plasminogen activator receptor (suPAR), and/or (ii) D2D3 cleavage products of suPAR in a population. Alternatively, the reference value is obtained by measuring the level of a marker in the form of (i) soluble urokinase plasminogen activator receptor (suPAR), and/or (ii) D2D3 cleavage products of suPAR from a sample from a subject with a known level of low-grade inflammation and/or metabolic syndrome. In a particular embodiment, the reference level is <=3.0 ng per ml using the assays known in the art, e.g., the SuPARnostic™ kit sold by Virogates A/S, Denmark. The level of said marker in a subject having low-grade inflammation and/or metabolic syndrome is increased at least about 10% as compared to said reference sample. In more specific embodiments, the level of said marker is increased at least about 25%, 50%, 75% and/or above 100%.

Furthermore, the invention provides a method for predicting the risk of developing a metabolic syndrome-related disease and/or low-grade inflammation-related disease, in particular, cancer and/or the risk of mortality within 1 year, 3 years, 5 years, 10 years, 1-10 years, 1-5 years or 5-10 years in a mammalian subject, particularly, a human subject, comprising:
   (a) performing an in vitro measurement of the level of a marker in the form of (i) soluble urokinase plasminogen activator receptor (suPAR), and/or (ii) D2D3 cleavage products of suPAR in one or more samples comprising a biological fluid derived from said subject, and
   (b) using the measurement values obtained as a factor to predict the risk of developing a metabolic syndrome-related disease and/or low-grade inflammation-related disease, the risk of developing cancer and/or the risk of mortality within e.g., 1, 3, 5, 10 or between 1-10 years, 1-15 years, 5-10 years.

By the 'risk of mortality' we mean the risk of general mortality, rather than the risk of dying from a particular disease.

In another specific embodiment, the method for predicting the risk of developing a metabolic syndrome-related disease and/or low-grade inflammation-related disease in a subject, (e.g., human subject), the risk of developing cancer and/or the risk of mortality within e.g., 1, 3, 5, 10 or between 1-10 years, 1-15 years, 5-10 years comprises
   (a) isolating a sample from a subject;
   (b) measuring the level of a marker in the form of (i) soluble urokinase plasminogen activator receptor (suPAR), (ii) and/or D2D3 cleavage products of suPAR;
   (c) comparing the measurement obtained in step (b) with a reference value, wherein an increase in the levels of said marker indicates increased risk of developing low-grade inflammation-related disease, metabolic syndrome-related disease, cancer and/or mortality.

As above, the reference value is a standard of levels of a marker in the form of (i) soluble urokinase plasminogen activator receptor (suPAR), and/or (ii) D2D3 cleavage products of suPAR in a population. Alternatively, the reference value is obtained by measuring the level of a marker in the form of (i) soluble urokinase plasminogen activator receptor (suPAR), and/or (ii) D2D3 cleavage products of suPAR from a sample from a subject free of low-grade inflammation-related disease and/or metabolic syndrome-related disease.

The level of said marker is increased at least about 10% and/or 1 ng/ml, or between about 1-20 ng/ml in said sample as compared to said reference sample. In specific embodiments, the level of marker may be increased at least about 2 ng/ml, 3 ng/ml, 3.5 ng/ml, 5 ng/ml, 8 ng/ml, 10 ng/ml, 15, ng/ml, 20 ng/ml or in the following ranges: (1-3 ng/ml, 1-5 ng/ml, 3-5 ng/ml, 5-10 ng/ml, 10-15 ng/ml, 15-20 ng/ml). In a particular embodiment, an increased risk of developing any of the said diseases or general mortality within any of the periods defined above is diagnosed if the suPAR level is more than about 3.0 ng/ml (or 4, 5 or 6 ng/ml) in men and more than about 3.5 ng/ml (or 4.5, 5.5 or 6.5) in women.

In a particular embodiment, the method of the present invention is used to measure increased risk of developing diabetes. In such an embodiment, step (b) may further comprise measuring glucose levels. Type 2 diabetes mellitus (T2DM) at baseline is defined as ICD8-code 250 and ICD10-codes E10-E14, or if the individual has a fasting blood glucose level of at least 7.0 mmol/L, or uses oral antidiabetic drugs or insulin.

In another particular embodiment, the method of the present invention is used to measure the increased risk of developing cardiovascular disease (CVD). In such an embodiment, step (b) may further comprise measuring blood pressure, HDL-cholesterol, LDL-cholesterol, total cholesterol, triglycerides, hsCRP or N-terminal fragment of brain-type natriuretic peptide (NT-proBNP). CVD may be defined as including cardiovascular mortality, ischemic heart disease (ICD-8 codes 410 to 414 or ICD-10 codes I20 to I25), and stroke (ICD-8 codes 431, 433, and 434 or ICD-10 codes I61 and I63)

In yet another particular embodiment, if blood glucose levels, lipids or hsCRP or NT-proBNP levels are within the normal range, the method of the present invention is used to measure increased risk of developing cancer, in particular breast cancer, leukemia, prostate cancer and/or lung cancer.

In yet another particular embodiment the method of the present invention is used to measure increased risk of mortality in ten years. In such an embodiment, step (b) may further comprise measuring NT-proBNP concentrations in plasma.

The invention is further directed to a method for monitoring the treatment of low-grade inflammation and/or metabolic syndrome in a mammalian subject comprising:
(a) isolating a sample from a subject undergoing treatment for low-grade inflammation (e.g. anti-inflammatory treatment, cancer) and/or metabolic syndrome;
(b) measuring the level of a marker in the form of (i) soluble urokinase plasminogen activator receptor (suPAR), (ii) and/or D2D3 cleavage products of suPAR, wherein a decrease in the level of said marker used in step (b) is an indication of progression of treatment.

In a particular embodiment, the level of said marker is decreased at least about 10% and/or 1 ng/ml and preferably from about 1.3-3 ng/ml in said sample as compared to said reference sample during the course of said treatment. Alternatively, the level of said marker may be decreased at least about 25%, 50%, 75%, and/or above 100% or between at least about 10% to about 100%.

According to the above methods, said metabolic syndrome-related disease and/or low-grade inflammation-related disease may be either cardiovascular disease, chronic obstructive lung disease or diabetes type 2, Alzheimer's disease, chronic eczema, asthma bronchiale, autoimmune disease. In particular, an inflammation-related disease may be cancer (e.g., lung, breast, leukemia, prostate).

According to the above methods, said biological fluid is preferably one of blood, blood serum, blood plasma or urine.

According to one embodiment of the above methods, said subject is either human immunodeficiency virus-infected and receiving Highly Active Anti-Retroviral Treatment (HAART) or is apparently healthy. If the patient is HIV-infected, then preferably, at least in the context of assessing the risk of mortality, the patient does not have AIDS. By 'healthy' we mean that the patient has not been diagnosed with a life-threatening condition (such as cancer, cardiovascular disease or chronic obstructive lung disease), an autoimmune disease or diabetes type 2.

In the various embodiments of the invention, the patient may be over 40 years of age, for example over 50 or over 60, and may be under 70 years of age, for example under 60 or under 50. The patient may be Caucasian.

According to one embodiment of the above methods, said one of more samples are derived from said subject at one or more points in time. Optionally, said one or more measurements are compared to assess the efficacy of a prophylactic course of action and/or treatment.

According to the above methods, said in vitro measurement is preferably an ELISA assay. Suitable ELISAs for suPAR levels are disclosed in Mizukami et al (1995) *Blood* 86, 203-211.

According to the above methods, in step b) one or more of the following additional measurements derived from the subject selected from the group consisting of: age, gender, ethnicity, smoker, non-smoker, systolic/diastolic blood pressure, cholesterol, triglycerides and waist circumference measurement, may be used to diagnose low-grade inflammation and/or metabolic syndrome.

The method may further comprise conducting a glucose tolerance test, assaying TNF-alpha, IL-6, leukocyte count, hsCRP, fasting plasma (Blood-) glucose, blood pressure, cholesterol, C-reactive protein and/or triglyceride levels.

The invention is further directed to methods and compositions for treatment of metabolic syndrome and/or low-grade inflammation. Specifically, the invention is directed to a method comprising administering to a subject in need thereof an amount of a substance that decreases the level of suPAR sufficiently to treat said low-grade inflammation and/or metabolic syndrome. Preferably, the plasma level is reduced to below 6 ng/ml, more preferably to below 5, 4 or 3 ng/ml. The substance that is administered may be an anti-suPAR antibody (e.g., a monoclonal or polyclonal antibody). The substance may alternatively be a suPAR analog or derivative capable of binding uPA or a suPAR cleavage product such as one or more of the D2D3 isoforms. The composition of the present invention may be a pharmaceutical composition for use in treatment or prevention of low-grade inflammation and/or metabolic syndrome comprising a substance that lowers the level of suPAR in a mammalian subject.

In a related aspect, the invention is directed to the use of a substance for preparing a therapeutic composition for the treatment or prevention of low-grade inflammation and/or metabolic syndrome, wherein said substance lowers the level of suPAR in a mammalian subject.

In a specific embodiment, the invention is directed to a computer readable medium having computer logic stored therein configured to cause, when executed on a data processing system, the data processing system to compute risk and/or change in risk of a low-grade inflammation-related disease, a metabolic syndrome-related disease, cancer and/or mortality within e.g., 1, 3, 5, 10 or between 1-10 years, 1-5 years, 5-10 years comprising:
(a) logic for receiving one or more measurements derived from a mammalian subject wherein at least one measurement is an in vitro measurement of the level of a marker in the form of (i) soluble urokinase plasminogen activator receptor (suPAR), and/or (ii) D2D3 cleavage products of suPAR in one or more samples derived from said subject;
(b) logic for analysis of one or more of said measurements of step (a); and
(c) logic for computing risk and/or change in risk of said low-grade inflammation-related disease and/or said metabolic syndrome-related disease (e.g., cardiovascular disease, chronic obstructive lung disease and diabetes type 2), cancer (e.g., breast cancer or lung cancer), and/or mortality in e.g., 1 year, 3 years, 5 years, 10 years, 1-10 years, 1-5 years, 5-10 years based on analysis in step (b) of said measurements.

In a particular embodiment, the logic in (a) comprises a logic for receiving two or more measurement derived from a human subject wherein at least one measurement is an in vitro measurement of the level of marker in the form of (i) soluble urokinase plasminogen activator receptor (suPAR), and/or (ii) D2D3 cleavage products of suPAR in one or more samples derived from said subject. If the data processing system is used to compute risk of developing diabetes, the logic may further receive measurements of blood glucose levels derived from a mammalian subject; if the data processing system is used to compute risk of developing cardiovascular disease, the logic may further receive measurements of blood pressure, HDL-cholesterol, LDL-cholesterol, total cholesterol, hsCRP, and/or triglycerides; if the data processing system is used to compute risk of mortality in a mammalian subject in e.g., 1 year, 3 years, 5 years, 10 years, 1-5 years, 1-10 years or 5-10 years the logic may further receive measurements of brain natriuretic peptide concentrations.

The data processing system in said computer readable medium may be further caused to monitor progression of treatment of low-grade inflammation-related disease and/or metabolic syndrome-related disease from said change in risk.

The invention further encompasses a computer program product, comprising the computer readable medium of the present invention. A "computer program product" is used to generally refer to media such as a hard drive and removable storage drive and storage unit. In one embodiment where the invention is implemented in whole or in part, the software can be stored in a computer program product and loaded into the computer using a removable storage drive, hard drive and communications interface.

The invention is further directed to a computer for determining the risk and/or change in risk of developing a metabolic syndrome-related disease, low-grade inflammation-related disease, cancer and/or mortality within e.g., 1 year, 3 years, 5 years, 10 years or between 1 and 10 years, 1 and 5 years, or 5 and 10 years comprising
  (a) a computer-readable data storage medium configured to store a data storage material encoded with computer-readable data, wherein said data comprises one or more measurements derived from one of more samples from a mammalian subject, wherein at least one measurement is an in vitro measurement of the level of a marker in the form of (i) soluble urokinase plasminogen activator receptor (suPAR), and/or (ii) D2D3 cleavage products of suPAR;
  (b) a storage medium having stored therein instructions for processing said computer-readable data;
  (c) a central-processing unit responsive to said instructions coupled to said storage medium and to said computer-readable data storage medium for processing said computer-machine readable data into risk measurement and treatment progression values; and
  (d) an output device coupled to said central-processing unit of (c) for outputting said risk and/or change in risk values.

In a particular embodiment, the computer-readable data storage medium (a) of the computer of the present invention comprises data comprising two or more measurements derived from a human subject wherein at least one measurement is an in vitro measurement of the level of marker in the form of (i) soluble urokinase plasminogen activator receptor (suPAR), and/or (ii) D2D3 cleavage products of suPAR in one or more samples derived from said subject. If the computer is used to compute risk of developing diabetes, the data may further comprise measurements of blood glucose levels from a mammalian subject; if the computer is used to compute risk of developing cardiovascular disease, the data may further comprise measurements of blood pressure, HDL-cholesterol, LDL-cholesterol, total cholesterol and/or triglycerides; if the computer is used to compute risk of mortality in a mammalian subject within e.g., 1 year, 3 years, 5 years, 10 years or 1-10 years, 1-5 years, or 5-10 years, the data may further comprise measurements of brain natriuretic peptide concentrations.

In a specific embodiment, the invention is directed to a client computer for providing access to a risk computation system for determining the risk and/or change in risk of developing a metabolic syndrome-related disease, low-grade inflammation-related disease (e.g., cancer) and/or risk of mortality in a mammalian subject within, e.g., 1 year, 3 years, 5 years, 10 years or between 1-10 years, 1-5 years, 5-10 years, the client computer comprising:
  (a) an input device for receiving one or more measurements derived from a mammalian subject wherein at least one measurement is an in vitro measurement of the level of a marker in the form of (i) soluble urokinase plasminogen activator receptor (suPAR), and/or (ii) D2D3 cleavage products of suPAR in one or more samples derived from said subject;
  (b) a communication interface for communicating the received one or more measurements to a server computer configured to analyse said one or more measurements of step (a); and compute a risk value; and
  (c) a communications interface for receiving, from the server computer a computed risk value.

In a particular embodiment, the input device (a) of the client computer of the present invention receives two or more measurements derived from a human subject wherein at least one measurement is an in vitro measurement of the level of marker in the form of (i) soluble urokinase plasminogen activator receptor (suPAR), and/or (ii) D2D3 cleavage products of suPAR in one or more samples derived from said subject. If the client computer is used to compute risk of developing diabetes, the input device (a) may further receive measurements of blood glucose levels from a mammalian subject; if the client computer is used to compute risk of developing cardiovascular disease, the input device (a) may further receive measurements of blood pressure, HDL-cholesterol, LDL-cholesterol, total cholesterol and/or triglycerides; if the client computer is used to compute risk of developing cancer (e.g., breast cancer or lung cancer); if the client computer is used to compute risk of mortality in a mammalian subject within e.g., 1 year, 3 years, 5 years, 10 years or between 1-10 years, 1-5 years, 5-10 years, the input device (a) may further receive measurements of NT-proBNP.

In yet another particular embodiment, the invention is directed to a computer based method for determining the risk of developing a metabolic syndrome-related disease, low-grade inflammation-related disease (e.g., cancer) and/or risk of mortality in a mammalian subject, e.g., within 1 year, 3 years, 5 years, 10 years or between 1-10 years, 1-5 years or 5-10 years comprising:
  (a) receiving under computer control in vitro measurement of the level of a marker in the form of (i) soluble urokinase plasminogen activator receptor (suPAR), and/or (ii) D2D3 cleavage products of suPAR in one or more samples derived from said subject;
  (b) analyzing under computer control said in vitro measurement received in (a)
  (c) calculating under computer control a risk value for developing a metabolic syndrome-related disease, low-grade inflammation-related disease (e.g., cancer) and/ or risk of mortality in a mammalian subject within 5 years, 10 years or between 5-10 years using analyzed measurements obtained in (b).

BRIEF DESCRIPTION OF THE DRAWINGS

FIG. 1 shows box-plots showing fasting serum suPAR concentration in HIV infected patients receiving HAART with lipodystrophy (LIPO) and without lipodystrophy (NONLIPO). Box and whisker plots show the $10^{th}$, $25^{th}$, $50^{th}$ (median), $75^{th}$ and $90^{th}$ percentiles. Extreme cases of individual variables are indicated by asterisks.

FIG. 2A shows correlation between suPAR and insulin stimulated nonoxidative glucose metabolism (NOGM). ●, lipodystrophic HIV-infected patients; Δ, nonlipodystrophic HIV-infected patients. Linear correlation line, correlation coefficient and significance level are indicated. FIG. 2B shows correlations between plasma suPAR level versus HOMA-IR (homeostasis model assessment insulin resistance index; Matthews et al. 1985) in HIV-infected patients on HAART (highly active antiretroviral therapy), who either displayed lipodystrophy (LIPO, n=18) [O]; or was free of lipodystrophy (NONLIPO, n=18) [Δ]. Further, a group of HIV-infected patients naïve to HAART (NAÏVE, n=7) [□], was included in the analysis. Linear regression lines including all patients in analysis are presented. LIPO and NONLIPO (n=36) p-suPAR vs. HOMA-IR r=0.58, p<0.001 (age corrected r=0.49, p=0.003). All (n=43) p-suPAR vs. HOMA-IR r=0.49, p<0.001 (age corrected r=0.45, p=0.003). FIG. 2C shows correlations between suPAR versus 2 hours plasma glucose after a standard oral glucose (75 gram) challenge in HIV-infected patients on HAART. ●, lipodystrophic HIV-infected patients; Δ, nonlipodystrophic HIV-infected patients. Linear correlation line, correlation coefficient and significance level are indicated. FIG. 2D shows correlations between suPAR versus a composite measure of insulin sensitivity (ISI composite) obtained during an oral glucose tolerance test in HIV-infected patients on HAART. ●, lipodystrophic HIV-infected patients; Δ, nonlipodystrophic HIV-infected patients. Linear correlation line, correlation coefficient and significance level are indicated.

FIG. 4 shows circadian concentrations of suPAR in intervals of 20 min as percentage of the mean (100%) from n=5 HIV-infected patients receiving HAART, who had suppressed HIVRNA. Upper plot shows individual diurnal profiles. Lower plot shows mean+/−SD of the same patients.

FIGS. 5A and 5B show the correlation of suPAR levels with overall survival. FIG. 5A shows correlations between suPAR, age and sex. Boxplot with lines correspond to women, and dots with men. FIG. 5B shows survival according to suPAR quartiles. Thin line represents low suPAR (N=650, suPAR below 3,620 ng/ml), medium thin line N=651, suPAR between 3.622-4.266), medium thick line, N=651, suPAR between 4,269-4,912. Thickest line represents 650 individuals with highest suPAR (>4.915). Difference between groups significant (Log Rank, p<0.001).

FIGS. 6A, 6B, and 6C show the correlation of suPAR levels with smoking status and exercise. FIG. 6A shows suPAR levels among men according to smoking status. Boxes with horizontal lines represent smokers, white boxes occasional-smokers and boxes with vertical lines represent non-smokers. Mean suPAR levels were significantly higher among male smokers (4.57 (sd1.45) ng/ml, N=580) compared to occasional smokers (3.64 (sd 0.86), N=56), P<0.001, Mann-Whitney U-test for all age groups. The suPAR level among male non-smokers was mean 3.72 (std 1.22), N=674) which was significantly lower than smokers (Mann-Whitney p<0.001) but not different compared to occasional-smokers (p=0.8). Black line indicates median suPAR and boxes 25% quartiles above and below median. FIG. 6B shows suPAR levels among women according to smoking status and age. Boxes with horizontal lines represent smokers; white boxes represent occasional-smokers; and boxes with vertical lines represent non-smokers. Female smokers (N=511) had significantly higher suPAR levels compared to occasional smokers (N=50) and non-smokers (N=731), p<0.001. No difference between occasional-smokers and non-smokers. Black line indicates median suPAR and boxes 25% quartiles above- and below-median. FIG. 6C shows the relationship between suPAR and exercise in the different age-groups. Age-group 1 consisted of individuals that did not exercise regularly (N=539), age-group 2 of individuals did low-to moderate exercise (taking walk etc) (N=1454), age-group 3 of individuals exercised on a regularly basis (e.g. jogging) (N=546) and age-group 4 consisted of professional sportsmen (N=17).

DETAILED DESCRIPTION OF THE INVENTION

Figure 2A:
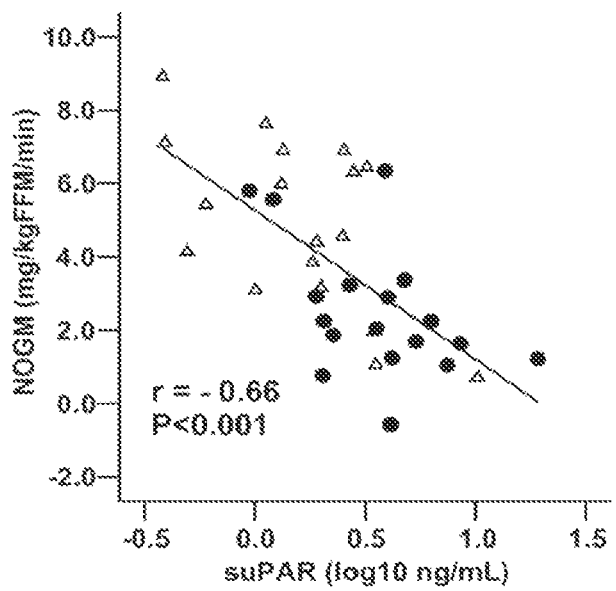
FIGS. 2A, 2B, 2C, and 2D show correlation between suPAR and measures of glucose metabolism and insulin sensitivity.

The terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

The invention is based on the unexpected observation that soluble uPAR (suPAR) is present in elevated levels in serum, plasma and urine of individuals with low-grade inflammation and in individuals with metabolic disorders. The level of suPAR is shown to vary independently of body mass index (BMI), and thus provides a more useful marker of low-grade inflammation and metabolic syndrome than currently available markers. Furthermore suPAR levels measured in a biological fluid derived from an individual are shown to be a strong predictive marker for risk of development of diseases that can originate from low-grade inflammation and metabolic disorders, including cardiovascular disease, chronic obstructive lung disease, diabetes type 2, and developing cancer (e.g. lung cancer, leukemia, prostate and breast cancer and/or the risk of mortality within e.g., 1 year, 3 years, 5 years, 10 years or between 1-years, 5 years-10 years, 1-10 years.

As defined herein, "low grade inflammation" is characterized by (1) elevated levels of one or more of a pro-inflammatory cytokine (e.g., IL-6, TNF alpha, IFN gamma), serum amyloid A (SAA), orosomucoid, fibrinogen, gamma-globulin; and/or (2) increased plasma viscosity, erythrocyte sedimentation rate (ESR) and/or leukocyte count; and/or (3) decreased levels of serum albumin as compared to a reference value (see, for example, Kolb et al., 2005, Diabetologia 48:1038-1050); and/or (4) increased acute phase response as measured for example by hypersensitive C-reactive protein (hs-CRP) (e.g. an hs-CRP level of 1.5-3.5 times, preferably about twice, the normal level); all in the absence of observable inflammation. In a particular embodiment, low grade inflammation is characterized by elevation of one or more of the mentioned markers, in the absence of observable inflammation. In particular, low-grade inflammation can be characterised as an hs-CRP level of higher than 1 mg/l (particularly more than 3 mg/l), for example as measured using the particle enhanced immunoturbidimetry assay (Roche Diagnostics) described below.

As defined herein, "metabolic syndrome" is characterized by a combination of high blood pressure, insulin resistance with increased glucose production and decreased glucose utilization, central (abdominal) obesity, dyslipidemia namely elevated triglycerides, LDL-cholesterol and total cholesterol, and reduced high-density lipoprotein cholesterol, and "low grade inflammation" as stated above. The broadly accepted criteria for diagnosis of metabolic syndrome, provided by the National Cholesterol Education Program (NCEP) Adult Treatment Panel III (ATP 111) with minor modifications, are as follows:

Elevated waist circumference: Men—Equal to or greater than 40 inches (102 cm) and Women—Equal to or greater than 35 inches (88 cm);

Elevated triglycerides: Equal to or greater than 150 mg/dL;

Reduced HDL ("good") cholesterol: Men—Less than 40 mg/dL, Women—Less than 50 mg/dL;

Elevated blood pressure: Equal to or greater than 130/85 mm Hg;

Elevated fasting glucose: Equal to or greater than 100 mg/dL. Accordingly, in a particular embodiment of the invention, a subject is diagnosed with metabolic syndrome if the subject exhibits 3 or more of the above listed 5 components.

In a more particular embodiment, metabolic syndrome is defined according to the International Diabetes Federation definition as central obesity (waist men/women >94/80 cm) together with at least two of the following: elevated serum triglycerides >1.7 mmol/l (150 mg/dl), reduced serum high-density lipoprotein cholesterol (<1.03 mmol/l (40 mg/dl), elevated plasma glucose (>5.6 mmol/l (100 mg/dl) or elevated BP (systolic BP>130 mm Hg or diastolic BP>85 mm Hg).

Decreasing the suPAR level may be achieved by decreasing the rate of suPAR production or by decreasing the stability of suPAR produced, e.g. by clearing it from the body with an anti-suPAR anti-body.

1. suPAR and/or its Cleavage Products for Use as a Marker:

The protein suPAR (NCBI Accession no. AAK31795 and isoforms of the receptor, NP_002650, Q03405, NP_002650, NP_001005376) is the soluble portion of Urokinase-type Plasminogen Activator Receptor (uPAR), which is released by cleavage of the GPI anchor of membrane-bound uPAR. suPAR is a family of glycosylated proteins consisting of full length suPAR (277 amino acids (1-277)) and suPAR fragments D1 (1-83), and D2D3 (84-277) generated by urokinase cleavage or human airway trypsin-like protease, D1 (1-87) and D2D3 (88-277) generated by MMP cleavage, D1 (1-89) and D2D3 (90-277) also generated by urokinase cleavage or human airway trypsin-like protease, D1 (1-91) and D2D3 (92-277) generated by cleavage by plasmin. Continuous and discontinuous epitopes present in the protein suPAR and its cleavage products may be used to monitor their presence and abundance in a biological fluid by immunodetection with mono- or poly-clonal antibodies. Thus, antibodies directed to accessible epitopes common to suPAR and its cleavage products (e.g. D2D3) can be used to detect both suPAR and its cleavage products in a biological fluid.

The use of suPAR as a marker has the advantage that it is more stable than other markers of the immune response, e.g. TNF-α and IL-6. For example, suPAR levels in healthy individuals are known to be stable throughout the day (Sier C F, et al., 1999, Lab Invest 79:717-722). Similarly, circadian changes in plasma concentration of suPAR in HIV-infected patients on stable HAART are shown to be very limited (Example 1). Thus, suPAR measurements based on a biological fluid derived from a subject will be valid, independent of whether the subject is fasting or not, and largely independent of the time schedule for sampling. This is not the case for alternative markers such as TNF-α and IL-6, which show substantial circadian fluctuations. A flexible sampling schedule and the stability of suPAR molecules in stored samples of biological fluid is a great advantage for its use as a marker in the clinical setting.

2. Biological Samples Suitable for Detection of suPAR or its Cleavage Products as a Marker suPAR, or its cleavage products (e.g., D2D3), can be used as a marker for diagnostic, prognostic and predictive purposes by measuring the level of suPAR or its cleavage products in a biological fluid derived from a mammalian subject, particularly, a human subject or patient, as illustrated in the examples herein. suPAR and its cleavage products are present in all biological fluids derived from a mammalian subject, particularly, a human subject, including cerebrospinal fluid, plasma, serum, blood, urine, semen, saliva and sputum.

Where the biological sample is urine, the measurements may be based on the urine suPAR/creatinine value from a subject, since this value is known to be highly correlated to the concentration of suPAR in a serum (plasma) sample derived from the same subject. Similarly the urine suPAR/creatinine values of an HIV patient on HAART is highly correlated to the concentration of suPAR in serum (plasma) samples derived from the same subject (Example 1). Thus, urine samples may also be employed for the measurement of suPAR, or its cleavage products, in a subject (including an HIV patient on HAART), where the measured level in urine is normalized for protein content (e.g. using creatinine). These normalized values may be employed as a marker for the diagnostic, prognostic or predictive purposes of the present invention.

3. Detection and Quantitation of suPAR and its Cleavage Products

Accurate methods for measuring the level of suPAR and/or its cleavage products in a biological fluid derived from a subject, include immunodetection methods e.g. Enzyme-Linked ImmunoSorbent Assay (ELISA), which are particularly suitable as such methods are relatively cheap and simple to perform in the clinical setting. ELISAs can be adapted to analyze both small and large numbers of samples, and include both an ELISA plate format with wells coated with suPAR specific antibodies, or adapted to a dipstick format incorporating all components of the ELISA assay. Additionally, suPAR levels can be measured by proteomic approaches such as western blot, Luminex, MALDI-TOF, HPLC and automated immune analyzer platforms such as Bayer Centaur, Abbott Architect, Abbott AxSym, Roche COBAS and the Axis Shield Afinion.

4. suPAR as a Marker for Diagnosis of Low-Grade Inflammation and Metabolic Syndrome in A) HIV-Infected Patients on HAART Treatment, and B) Apparently Healthy Subjects Low-grade inflammation, as defined above, is a subclinical state in an apparently healthy subject, who exhibits no observable inflammation, yet in whom immune activation is detectable, although at a level far below that seen in acute infections. hsCRP (C-reactive protein), measured using available sensitive tests, is currently used as a marker for low-grade inflammation in a subject.

Markers for the diagnosis of low-grade inflammation in a subject have particular importance, since this sub-clinical condition seems to be linked to subsequent development of low-grade inflammation-related diseases including type-2 diabetes and CVD. Diagnosis of low-grade inflammation in a population would identify those members whose risk of developing low-grade inflammation related-diseases should be monitored further.

A) HIV-infected patients on HAART, who display a cluster of dysmetabolic features, have elevated levels of suPAR compared to treatment-matched, non-lipodystrophic HIV-infected patients (Example 1). Levels of suPAR in these HIV patient groups was positively correlated with leukocyte, lymphocyte, and monocyte numbers, all of which are blood cells of particular importance for the immune activation and inflammatory status of a patient. These data, and the observed strong positive-correlation between suPAR and TNF-α, identify suPAR as a novel strong diagnostic marker of low-grade inflammation in HIV-infected patients.

suPAR levels in these HIV patient groups was also strongly correlated with respectively, fat distribution, insulin sensitivity and lipidemia, identifying suPAR as a marker of metabolic syndrome in these patients. Use of SuPAR as a marker is also shown to provide a stronger prediction of metabolic syndrome than the alternative markers, TNF-α and IL-6.

B) White blood cell (WBC, i.e. leukocyte) count is a marker for immune activation and low-grade inflammation in the general population. In the general human population, comprising the Monica10 cohort, the suPAR level and the WBC count was highly correlated, and shown to be independent of age and gender (Example 4, Table 9; Example 5). These data establish suPAR as a novel marker of low-grade inflammation in the general population that includes apparently healthy individuals. Furthermore suPAR provides a valuable marker for the purpose of staging the progress of low-grade inflammation in a subject. suPAR has application as a marker to monitor the risk of on-set of low-grade inflammation-related diseases, since suPAR is shown to be a marker for the diseases Type 2 Diabetes and CVD. Cancer is an additional low-grade inflammation-related disease for which suPAR is a useful marker. This is consistent with the observation that leucocytes (white blood cell count), are a well established marker of inflammation, linked to cancer development.

The metabolic syndrome is defined by the following 5 components: waist circumference, fasting glucose level, low HDL-cholesterol, high plasma triglyceride, increased diastolic and/or systolic blood pressure; according to the NCEP ATPIII 2001 definition with the 2004 glucose modification; (Grundy S M et al., 2005, Circulation 112:2735-2752).

In the general human population, comprising the Monica10 cohort, suPAR levels were positively correlated with the number of components of metabolic syndrome detected in an individual (Example 6). This was the case for both men and women in the tested population, and the association was independent of the subject's age. These data establish suPAR as a novel marker of metabolic syndrome in the general population that includes apparently healthy individuals.

4. suPAR as a Marker for Predicting the Risk for an Apparently Healthy Subject of Developing Diabetes Type 2.

suPAR is shown to be an independent predictor of the risk of developing diabetes (Example 5). In both univariate and multivariate analysis, high suPAR, age (older), sex (being male) and having the metabolic syndrome were significantly associated with an increased risk of developing diabetes. Independent of age, sex and the metabolic syndrome, a 1 ng/mL increase in suPAR was associated with a 28% increased risk of developing diabetes. The use of suPAR as a marker for predicting the risk of developing diabetes will allow individuals at risk to improve their health chances by initiating a prophylactic course of action at a sufficiently early time point.

suPAR was also shown to correlate significantly with an increasing fasting glucose (Table 9). Example 5 demonstrates that suPAR strongly predicts type 2 diabetes. From these observations, it is deduced that suPAR most likely is a strong marker of insulin resistance, which is an underlying cause of the metabolic syndrome and type 2 diabetes mellitus (Grundy S M et al 2005, Circulation 112:2735-2752).

Figure 2B:
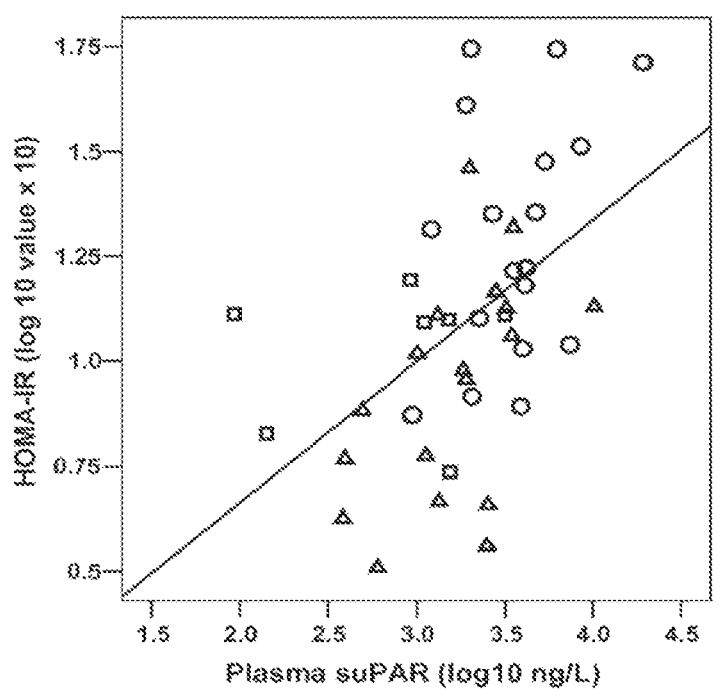
Figure 2:
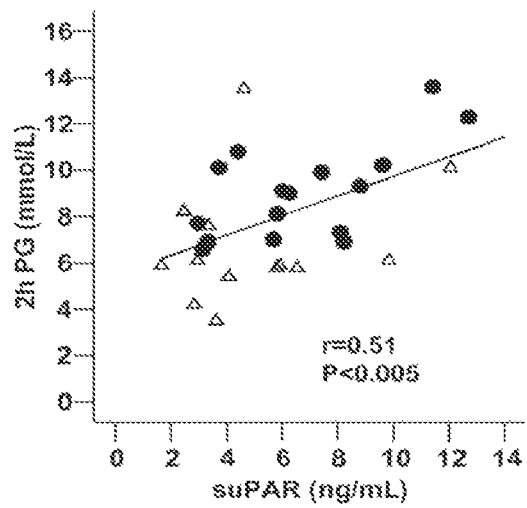
Figure 2:
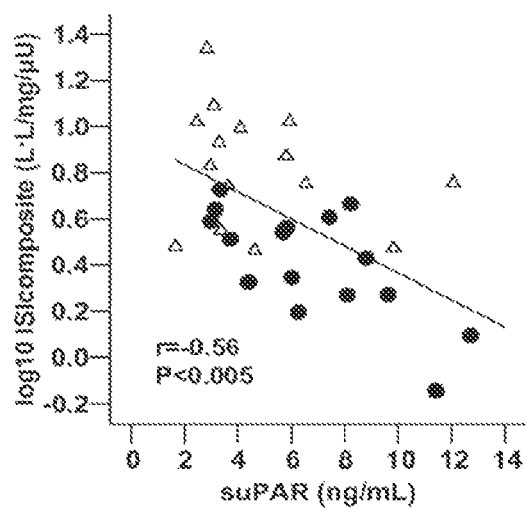

As prediabetes, in the form of e.g. impaired glucose tolerance, precedes type 2 diabetes and is more prevalent in individuals exhibiting the metabolic syndrome than individuals not having this syndrome, it is most likely that suPAR is both a strong marker and strong predictor of prediabetes and impaired glucose tolerance in the general population. In support of suPAR being a strong marker of insulin resistance is that this particular association has been demonstrated in HIV-infected individuals on a stable HAART regime using gold standard measurement of insulin sensitivity (Example 1, FIG. 2A). Also a more simple measure of insulin sensitivity namely HOMA-IR was associated with suPAR (FIG. 2B). Moreover, the observed correlation between plasma suPAR level and the 2-hour plasma glucose during an oral glucose tolerance test in HIV-infected individuals on a stable HAART regime (FIG. 2C) confirms suPAR as a strong marker of impaired glucose tolerance.

5. suPAR as a Marker for Predicting the Risk for an Apparently Healthy Subjects of Developing Cardiovascular Disease (CVD) and Ischemic Heart Disease (IHD).

suPAR is shown to be a strong, independent risk marker of development of a CVD event in apparently healthy individuals, that is not, or only weakly, correlated to classical predictors of CVD development (Example 4). Independent of sex, age, smoking status and metabolic syndrome, a 1 ng increase in suPAR was associated with a 15.4% increased risk of developing a CVD.

suPAR level is a significant predictor of the risk of developing an IHD in individuals who have not previously experienced an Acute Myocardial Infarct (Example 7). SuPAR predicted the risk of IHD independently of other classical markers of IHD. In an age-adjusted analysis, a 1 ng/ml increase in suPAR was associated with an increased risk of IHD of 21%.

suPAR as a marker for prediction of the risk of developing both CVC and IHD also gives an individual at risk the chance to initiate a prophylactic course of action at a time point that is sufficiently early as to lower their risk.

6. suPAR as a Marker for Predicting the Risk for an Apparently Healthy Subjects of Developing Cancer.

suPAR is shown to be a strong, independent risk marker of development of cancer in apparently healthy individuals (Example 10). Independent of sex and age, a 1 ng increase in suPAR is associated with a hazard ratio of 1.34 increased risk of developing overall cancer: Significant associations were found within the following cancer subgroups breast cancer, leukemia, prostate cancer and lung cancer.

suPAR as a marker for prediction of the risk of developing cancer also gives an individual at risk the chance to initiate a prophylactic course of action at a time point that is sufficiently early as to lower their risk. The effect of the risk intervention can be monitored using suPAR levels. An effective intervention will lower the suPAR level.

7. suPAR as a Predictor of Survival and Efficacy of Life Style Intervention suPAR levels in apparently healthy individuals are demonstrated to be strongly associated with mortality, independent of other markers (Example 3). In multivariate analysis, suPAR was the second strongest marker of mortality, after age.

The life style of an apparently healthy individual is shown to impact their suPAR levels significantly. In the case of smoking habit, smokers significantly impact their suPAR level and their survival prospects. Similarly, exercise habit has a significant impact on suPAR levels in an individual, where the level of exercise is associated with lower suPAR levels. It is thus apparent that regular suPAR measurements on a biological fluid derived from a mammalian subject, particularly, a human subject, would allow the physician to guide his subject with respect to his life expectancy based on current life style, and the efficacy of life-style changes taken in the course of prophylactic course of action, e.g. a physical exercise program may be proposed by a physician. Similarly, regular suPAR measurements would allow the physician to monitor the efficacy of medication; to monitor patient compliance in taking the prescribed medication, and to monitor the efficacy of a course of treatment to prevent or treat Metabolic Syndrome related diseases, including IHD, CVD and Type 2 Diabetes.

8. suPAR as a Marker for Monitoring Progression of Treatment of Metabolic Syndrome and/or Low-Grade Inflammation suPAR levels may also be used to monitor treatment of metabolic syndrome and/or low-grade inflammatory disease. A suPAR measurement may be made before treatment begins. During treatment, suPAR measurements may be taken at various time points. A decrease of at least about 10% and/or 1 ng/ml would be indicative of the effectiveness of a treatment protocol. suPAR levels may further be measured at various time points post-treatment.

9. Treatment of Metabolic Syndrome and/or Low-Grade Inflammation

Substances that decrease the level of suPAR in a mammalian subject may be used to treat metabolic syndrome and/or low-grade inflammation. In a particular embodiment, the substance may be an anti suPAR monoclonal or polyclonal antibody. Such antibodies may be obtained using methods known in the art. Various hosts may be used and include but are not limited to goats, rabbits, rats, mice, humans, and others. These hosts may be immunized by injection with suPAR or peptide fragments having a minimum length of 5-10 amino acids with immunogenic properties (see e.g., WO90/12091). Various adjuvants may be used to increase immunological response. Such adjuvants include, but are not limited to, Freund's, mineral gels such as aluminum hydroxide, and surface active substances such as lysolecithin, Pluronic polyols, polyanions, peptides, oil emulsions, keyhole limpet hemocyanin, and dinitrophenol. BCG (bacilli Calmette-Guerin) and *Corynebacterium parvum* are especially preferable in humans. The following steps may be used to obtain said antibody: (a) optionally conjugating uPAR or an immunogenic part thereof to a carrier protein; (b) immunizing a host animal with said polypeptide or polypeptide-carrier protein conjugate of step (a) with an adjuvant and (c) obtaining antibody from said immunized host animal. Preferably, any antibody that is used in the context of this invention binds to full length suPAR, not just to fragments thereof, such as the D2D3 fragment.

Monoclonal antibodies to the said receptor or receptor peptides used in the method of the present invention may be prepared using any technique which provides for the production of antibody molecules by continuous cell lines in culture. These include, but are not limited to, the hybridoma technique, the human B-cell hybridoma technique, and the EBV-hybridoma technique. See, e.g., Kohler, et al., 1975, Nature 256: 495-497; Kozbor et al., 1985, J. Immunol. Methods 81: 31-42; Cote et al., 1983, Proc. Natl. Acad. Sci. USA 80: 2026-2030; Cole et al., 1984, Mol. Cell Biol. 62: 109-120. Specifically, the method comprises the following steps: (a) immunizing an animal with an immunogenic receptor peptide; (b) isolating the antibody producing cells from the animal; (c) fusing the antibody producing cells with immortalized cells in culture to form monoclonal antibody-producing hybridoma cells; (d) culturing the hybridoma cells; and (e) isolating from the culture monoclonal antibodies which bind to said polypeptide.

Antigenic specificity is conferred by variable domains and is independent of the constant domains, as is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) *Science* 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299. By "ScFv molecules" we mean molecules wherein the $V_H$ and $V_L$ partner domains are linked via a flexible oligopeptide. These molecules may be used in the present invention.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the polypeptide(s) of the present invention and its specific antibody.

Other substances that may be used to obtain agents that decrease suPAR levels include but are not limited to a D2D3 cleavage product and/or another suPAR fragment. The substance may also include but is not limited to a suPAR analog or derivative capable of binding uPA. In a specific embodiment, such substances include but are not limited to 1) uPAR having an amino acid sequence containing a substitution, a deletion, a truncation and/or an addition, 2) chemically modified uPAR such as different degrees of glycosylation and 3) synthetic peptides containing part of the uPAR sequence. The suPAR analogues or fragments are large enough to generate antibodies that recognize human suPAR, uPAR and/or suPAR/uPAR fragments. Such analogues will generally have at least 60%, preferably at least 70%, 80%, 90%, 95% or 99% sequence identity with the most similar region of human suPAR.

Formulations of the substances of the present invention into pharmaceutical compositions is well known in the art, and is further described in Gennaro (ed.), 2000, Remington: The Science and Practice of Pharmacy, 20th ed., Lippincott, Williams & Wilkins (2000); and Ansel et al., 1999, Pharmaceutical Dosage Forms and Drug Delivery Systems, 7th ed., Lippincott Williams & Wilkins Publishers.

Such a composition typically contains from about 0.1 to 90% by weight (such as about 1 to 20% or about 1 to 10%) of the polypeptide or antibody of the invention in a pharmaceutically accepted carrier.

Various liquid and powder formulations can be prepared by conventional methods for inhalation into the lungs of the mammal to be treated.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds can be administered by the drip method, whereby a pharmaceutical formulation containing the antifungal agent and a physiologically acceptable excipient is infused. Physiologically acceptable excipients can include, for example, 5% dextrose, 0.9% saline, Ringer's solution or other suitable excipients. Intramuscular preparations, e.g., a sterile formulation of a suitable soluble salt form of the compounds, can be dissolved and administered in a pharmaceutical excipient such as Water-for-Injection, 0.9% saline, or 5% glucose solution. A suitable insoluble form of the compound can be prepared and administered as a suspension in an aqueous base or a pharmaceutically acceptable oil base, such as an ester of a long chain fatty acid (e.g., ethyl oleate).

The optimal percentage of the therapeutic agent in each pharmaceutical formulation varies according to the formulation itself and the therapeutic effect desired in the specific pathologies and correlated therapeutic regimens.

Conventional methods, known to those of ordinary skill in the art of medicine, can be used to administer compositions to the patient. These include but are not limited to subcutaneous, intrapulmonary, transmucosal, intraperitoneal, intrauterine, sublingual, intrathecal, or intramuscular routes) by using standard methods. In addition, the pharmaceutical formulations can be administered to the patient via injectable depot routes of administration such as by using 1-, 3-, or 6-month depot injectable or biodegradable materials and methods.

Regardless of the route of administration, the substance of the present invention is typically is administered at a daily dosage of about 0.01 mg to about 30 mg/kg of body weight of the patient (e.g., 1 mg/kg to 5 mg/kg). The pharmaceutical formulation can be administered in multiple doses per day, if desired, to achieve the total desired daily dose.

Conventional methods, known to those of ordinary skill in the art of medicine, can be used to administer the pharmaceutical formulation(s) of the present invention to the patient. The pharmaceutical compositions of the present invention can be administered alone, or in combination with other therapeutic agents or interventions. Specifically, the compositions of the present invention may further comprise a plurality of agents of the present invention.

10. suPAR Based Tools for Predicting Metabolic Syndrome-Related Diseases, Low-Grade Inflammatory-Related Diseases, Cancer and/or Mortality within 10 Years.

A combination of factors, one of which being suPAR, are predictive of the risk of developing CVD (including IHD and AMI), Diabetes type 2, cancer and/or mortality within 10 years. For example, stepwise backward logistic regression identifies those factors that have the highest statistical significance in determining the outcome of a large human population, and their risk of developing any one of these diseases. The combination of prediction factors, or criteria, comprises a model that may be employed in the form of an algorithm for predicting the individual health risks of a subject, as set out in Examples 8 and 9. Other algorithms can be implemented for calculating the risk of mortality or development of the diseases. For example, in an alternative embodiment, a risk analysis algorithm can include suPAR and age, or suPAR, age and gender, or suPAR, age and smoking. Using these factors as the input values of the algorithm, the output score may then be the different risk percentages over the next 5 years, 10 years or 5 years-10 years for the different diseases. Each disease may thus obtain a specific risk percentage, e.g. such as:

| Diabetes type 2 | risk 22% |
| CVD | risk 19% |
| Cancer | risk 36% |
| Mortality | risk 33% |

To further estimate the specific risk for a person, the following parameters could e.g. be measured and used as input values in a further calculation of risk:

| For Diabetes type 2 | fasting blood glucose |
| For CVD | blood pressure, HDL-cholesterol, LDL-cholesterol, total cholesterol, triglycerides |
| For cancer | smoking, age |
| For mortality | NT-proBNP concentrations |
| N-terminal fragment of brain-type natriuretic peptide | |

In the context of diagnosing the risk of developing cancer, the invention may have particular utility in relation to women who belong to a family with hereditary breast cancer and/or who have been shown to have a genetic marker associated with cancer, such as the BRCA1 and BRCA2 mutations.

The described combination of prediction factors may be used in the manufacture of a computer readable medium for entering determined prediction factor measurements and means for calculating and providing the risk of developing a Metabolic Syndrome-related diseases and/or low-grade inflammatory-related diseases e.g. CVD (including IHD and AMI), Diabetes type 2, developing cancer and/or mortality within one year, three years, five years, 10 years or 1-5 years, 1-10 years, five years-ten years.

In order to reach a prediction for a given patient, the physician performs a number of measurements, including the measurement of suPAR in a sample, e.g. biological fluid, derived from the patient, and enters the determined values into an computer logic for receiving test information comprising the level or relative amount of a protein that is suPAR and/or a D2D3 cleavage products thereof in a biological fluid derived from a mammalian subject, particularly, a human subject, and one or more further prediction factor parameters obtained from said mammalian subject, particularly, a human subject, executing computer logic for analysis of the level or relative amount of said protein in said biological fluid, and said one or more parameter, wherein the computer logic analyses the entered determined values and computes the risk of developing a Metabolic Syndrome-related disease, low-grade inflammatory-related disease, developing cancer and/or mortality within one year, three years, five years, 10 years or one-five years, one-ten years, five years-ten years.

Use of a computer comprising said computer readable medium would allow the physician to predict the risk of developing CVD (including IHD and AMI) and/or Diabetes type 2 in a mammalian subject, particularly, a human subject; as well as monitor the efficacy of medication, and patient compliance in taking the prescribed medication, in the course of treatment to prevent or treat Metabolic syndrome-related diseases, including CVD (including IHD and AMI), Diabetes type 2.

The use of a computer comprising said computer readable medium may also allow the physician to predict the risk of developing cancer and/or mortality within one year, three years, five years, 10 years or one-five years, one-ten years, five years-ten years in a mammalian, particularly, a human subject.

One such computer that may be used is a client computer e.g. in a doctor's surgery for providing access to a risk computation system for determining the risk and/or change in risk of developing a metabolic syndrome-related disease, low-grade inflammation-related disease, cancer and/or mortality within e.g., one year, five years, ten years, 1-5 years, 1-10 years or five years-ten years comprising:
  (a) a computer-readable data storage medium configured to store a data storage material encoded with computer-readable data, wherein said data comprises measurements derived from one or more samples from a mammalian subject, wherein at least one measurement is an in vitro measurement of the level of a marker in the form of (i) soluble urokinase plasminogen activator receptor (suPAR), and/or (ii) D2D3 cleavage products of suPAR;
  (b) a storage medium having stored therein instructions for processing said computer-readable data;
  (c) a central-processing unit responsive to said instructions coupled to said storage medium and to said computer-readable data storage medium for processing said computer-machine readable data into risk measurement and treatment progression values; and
  (d) an output device coupled to said central-processing unit of (c) for outputting said risk and/or change in risk values.

Alternatively, the client computer comprises: an input device for receiving one or more measurements derived from a mammalian subject wherein at least one measurement is an in vitro measurement of the level of a marker in the form of (i) soluble urokinase plasminogen activator receptor (suPAR), and/or (ii) D2D3 cleavage products of suPAR in one or more samples derived from said subject; a communication interface for communicating the received one or more measurements to a server computer configured to analyse said one or more measurements of step (a); and compute a risk value; and a communications interface for receiving, from the server computer a computed risk value.

The output device may include any device or circuitry suitable for outputting data. Examples of such output devices include devices for presenting data in a user-readable way, such as a display, a printer, and/or the like. Alternatively or additionally, the output device may include a communications interface for communicating the data to one or more other devices, e.g., computers. For example, the communications interface may include a serial port, a USB port, a parallel port, a short-range wireless communications interface, e.g., an infrared (e.g. IrDa) port, a Bluetooth transceiver, or the like. Further examples of interface circuits include a network card, a DSL modem, a gateway computer, a wireless communications circuit for cellular telecommunications, or the like. Yet further examples of output devices include devices or circuitry for writing the data on a computer-readable medium, such as a disk drive, a memory card interface, and/or the like.

For example, the data processing system to process computer-readable data may comprise a server computer or other data processing system having access to the communications interface. In some embodiments, the functionality of the risk computation system described herein may be distributed among a plurality of computers, e.g., computers connected via a computer network, e.g. a local area network, a wide area network, an Internet, or the like.

The input device may include any device or circuitry suitable for receiving data, such as a user interface, e.g. a keyboard, a graphical user interface, a pointing device, and/or the like. Other examples of input devices include communications interfaces as described herein and devices or circuitry for reading data from a storage medium, such as a disk drive, a memory card reader, and/or the like.

EXAMPLES

Example 1

SuPAR is a Marker of Low-Grade Inflammation and Metabolic Syndrome (Dysmetabolism) in HIV Infected Patients HIV infected individuals on HAART have recently been found to develop dysmetabolism, which is a form of metabolic syndrome similar to that seen in uninfected individuals, but within a shorter timeframe. The following study on HIV patients demonstrates the utility of suPAR as a marker for metabolic syndrome, and shows this marker to have a stronger predictive power than the markers, IL-6 and TNF-α for metabolic syndrome in this patient group.

Patient groups. A cohort of 36 HIV-infected male patients on HAART had estimated overnight fasting suPAR (Andersen et al., 2003, Metabolism 52:1343-1353). This cohort comprises 18 patients with lipodystrophy (LIPO), a marker of the metabolic syndrome in HIV patients, and 18 without any manifestations of metabolic syndrome (NONLIPO) as judged by a clinical investigation and a questionnaire, both of which have been described by (Andersen et al., 2003, Metabolism 52:1343-1353). All patients had received HAART for at least 12 months prior to examination, had a stable weight, and were free of any acute infection episode within three months of examination. All participants were Caucasians except two NONLIPO (Black Africans). Subjects gave their written informed consent and the protocol was approved by the Ethical Committee in Copenhagen, Denmark, and performed in accordance with the Helsinki Declaration II.

Protocol: Data obtained from hyperinsulinemic (40 mU·m$^{-2}$·min$^{-1}$) euglycemic (5.0 mM) clamps including glucose tracer technique and indirect calorimetry provided estimates of insulin sensitivity (Rd) and nonoxidative glucose disposal rate (NOGM) from the 18 LIPO and the 18 NONLIPO patients, as described by (Haugaard et al. 2005, Eur J. Endocrinol. 152:103-112). Five HIV-infected male patients on HAART had determined circadian plasma suPAR by collecting venous blood continuously during 20 min periods (6 ml/h) for 24 hours starting at 0800 in the morning after an overnight fast (Constant blood withdrawal pump type 3003, SWEMED LAB, International AB, V. Frolunda, Sweden). The samples were drawn from a catheter (inserted in the left antecubital vein) into unpreserved test tubes, and allowed to coagulate for 1 hour at 25° C., and thereafter centrifuged at 4° C. Serum was stored at −80° C. for later analysis. These 5 patients had meals served at 0900, 1230, and 1800. A snack was provided at 1500 and at 2100. They were not allowed to sleep before bedtime at 2230. They were allowed to walk around within the hospital area, however, exercise, as such, was prohibited.

To test whether plasma suPAR in HIV-infected patients on stable HAART may correlate with urine suPAR, as has been demonstrated previously in HIV negative individuals (Sier et al., 1999, Lab Invest 79:717-722), a sub-sample of 24 of the 36 patients had given overnight fasting urine. The effect of differences in dilution of the urine on suPAR levels was corrected with the amount of creatinine, as described previously (Sier et al., 1999, Lab Invest 79:717-722). Urine creatinine was measured as described (Mustjoki et al., 2000, Cancer Res 60:7126-7132).

suPAR measurement: suPAR levels were determined by ELISA assay as follows: Nunc maxisorp ELISA-plates (Nunc, Roskilde, Denmark) were coated overnight at 4° C. with a monoclonal rat anti-suPAR antibody (VG-1, Viro-Gates A/S, Copenhagen, Denmark, 3 μg/ml, 100 μl/well). Plates were blocked with PBS buffer+1% BSA and 0.1% Tween20, 1 hour at RT, and washed 3 times with PBS buffer containing 0.1% Tween20. 85 μl dilution buffer (100 mm phosphate, 97.5 mm NaCl, 10 g $L^{-1}$ bovine serum albumin (BSA, Fraction V, Boehringer Mannheim, Penzberg, Germany), 50 U $mL^{-1}$ heparin sodium salt (Sigma Chemical Co., St. Louis, Mo.), 0.1% (v/v) Tween-20, pH 7.4) containing 1.5 μg/ml mouse-anti suPAR-HRP labeled antibody (VG-2-HRP, ViroGates) and 15 μl plasma (or urine) sample was added in duplicates to the ELISA plate. After 1 hour of incubation at 37° C., plates were washed 10 times with PBS buffer+0.1% Tween20 and 100 μl/well HRP substrate added (Substrate reagent pack, R&D Systems Minneapolis, Minn.). The color reaction was stopped after 30 min using 50 μl/well 1M $H_2SO_4$ and measured at 450 nm. The intra-assay variation was 9.6% and the inter-assay variation 12.4%. Fasting plasma suPAR was measured in all 36 HIV-infected patients on HAART.

Other assays: Measurement of plasma glucose, insulin, C-peptide, free fatty acids, cholesterols, triglyceride including immunological and hematological parameters were performed as described by (Andersen et al., 2003, Metabolism 52:1343-1353; Haugaard et al., 2005, Eur J Endocrinol 152:103-112; Lihn et al., 2003, Am J Physiol Endocrinol Metab 285:E1072-E1080). Body composition was estimated by dual energy x-ray absorptiometry (DEXA) scanning (XR-36; Norland Medical System, Fort Atkinson, Wis.) and regional fat distribution was determined as previously described (Andersen et al., 2003, Metabolism 52:1343-1353).

Calculations: Total glucose disposal rate (Rd) was calculated using Steele's non-steady-state equations adapted for labeled glucose infusates (Hother-Nielsen et al., 1996, Metabolism 45:82-91). Distribution volume of glucose was taken as 200-ml/kg body wt and pool fraction as 0.65. Rate of glucose oxidation (GOX) was calculated from validated equations (Frayn, 1983, J Appl Physiol 55:628-634). NOGM was calculated as the difference between Rd and GOX.

Statistical analysis: Data are presented as means±SEM, and as medians and interquartile ranges when distributions were skewed. Analysis of variance (ANOVA) was performed to compare distribution of data between LIPO and NONLIPO. As age was slightly increased in LIPO compared with NONLIPO age was adjusted for by calculation of partial correlations. If data distribution was skewed, data were log transformed before applying ANOVA. Pearson correlation coefficient (r) and Spearman correlation coefficient (p) were applied to estimate associations between variables, when appropriate. A linear stepwise multiple regression model was used to test robustness of suPAR as an explanatory variable for dysmetabolic parameters. Calculations were performed by SPSS (SPSS ver. 12.0; SPSS Inc., Chicago, Ill., USA). Two-sided P values less than 0.05 were defined as statistically significant. A trend was noted if P was greater or equal to 0.05 but less than 0.2.

Results:

A. suPAR levels are tightly correlated with low-grade inflammation and metabolic syndrome in HIV patients:

suPAR was measurable in all 36 patients, with a median plasma suPAR level of 2.52 ng/ml (range 0.38-19.25). As suPAR showed a significant positive correlation with age (r=0.60, P<0.001), comparisons between study groups and correlation analysis were corrected for age (Table 1 and Table 2). The median plasma suPAR was increased 2-fold in LIPO compared to NONLIPO (P<0.005), although the difference attenuated after adjustment for age (FIG. 1, Table 1).

TABLE 1

Anthropometry, lipidemia, insulin sensitivity, and immunology of study groups

|  | LIPO | NONLIPO | P |
|---|---|---|---|
| Number | 18 | 18 |  |
| Age (yr) | 50 (2) | 43 (2) | <0.05 |
| BMI (kg/m$^2$) | 24.7 (0.6) | 22.6 (0.8) | <0.05 |
| Total fat mass (kg) | 16 (1) | 13 (2) | 0.13 |
| Total lean mass (kg) | 61 (2) | 54 (2) | <0.05[a] |
| Limb fat (%) | 36 (1) | 46 (2) | <0.0001[c] |
| Rd$_{clamp}$ (mg min$^{-1}$ kg$_{FFM}^{-1}$) | 5.9 (0.5) | 8.9 (0.6) | <0.001[b] |
| NOGM$_{clamp}$ (mg min$^{-1}$ kg$_{FFM}^{-1}$) | 2.5 (0.4) | 4.9 (0.5) | <0.005[a] |
| GOX$_{clamp}$ (mg min$^{-1}$ kg$_{FFM}^{-1}$) | 3.3 (0.2) | 4.0 (0.3) | 0.056[a] |
| fP-insulin (mmol/L) | 77 (11) | 32 (4) | <0.001[b] |
| fP-glucose (mmol/L) | 4.9 (0.1) | 4.8 (0.1) | ns |
| fP-total cholesterol (mmol/L) | 6.2 (0.4) | 4.8 (0.2) | <0.01[a] |
| fP-nonHDL cholesterol (mmol/L) | 5.2 (0.4) | 3.8 (0.2) | <0.01[a] |
| fP-TG (log10 mmol/L) | 0.47 (0.08) | 0.30 (0.06) | 0.09 |
| fP-suPAR (log10 ng/mL) | 0.56 (0.07) | 0.20 (0.09) | <0.005[#] |
| fP-TNF-α (log10 pg/mL) | 0.42 (0.06) | 0.32 (0.07) | ns |
| fP-IL-6 (log 10 pg/mL) | 0.54 (0.06) | 0.46 (0.06) | ns |
| Hemoglobin (mmol/L) | 8.8 (0.2) | 8.6 (0.2) | ns |
| Leukocytes (10$^9$/L) | 7.2 (6.0-9.0) | 5.6 (4.6-6.5) | <0.05 |
| Neutrophils (10$^9$/L) | 3.4 (2.5-4.8) | 3.1 (2.1-4.3) | ns |
| Lymphocytes (10$^9$/L) | 2.1 (0.2) | 1.6 (0.1) | <0.05[a] |
| Monocytes (10$^9$/L) | 0.57 (0.06) | 0.43 (0.06) | 0.14 |
| CD4 (cells/μL) | 427 (45) | 352 (46) | ns |
| HIV-RNA (copies/mL) | <20 (<20, 70) | <20 (<20, <20) | ns |
| CD4 nadir (cells/μL) | 130 (25) | 123 (32) | ns |
| HIV-RNA peak (log copies/mL) | 4.85 (0.33) | 5.05 (0.15) | ns |
| Duration of HIV-infection (mo) | 99 (14) | 72 (11) | 0.16 |
| Duration of NRTI therapy (mo) | 47 (7) | 42 (6) | ns |
| Duration of PI therapy (mo) | 32 (4) | 25 (4) | 0.16 |
| CDC classification: number A/B/C | 6/6/6 | 4/5/9 | ns |

Mean (SEM) or median (interquartile range);
[a] P < 0.05;
[b] P < 0.01;
[c] P < 0.001, following adjustment for age (yr);
[#] P = 0.06 after adjustment for age;
Limb fat (%), (limb fat mass + trunk fat mass)/trunk fat mass;
Rd is glucose disposal as estimated by a hyperinsulinemic euglycemic clamp using glucose tracer technique,
Rd minus GOX (glucose oxidation rate) is non-oxidative glucose metabolism rate (NOGM).
fP, fasting plasma;
CDC classification: categorized according to the Centers for Disease Control and Prevention (CDC) system of classification clinical stages A, B, and C, where C indicates AIDS diagnosis.

LIPO patients were slightly older on average than NON-LIPO and had slightly higher BMI, attributable to an increased lean body mass, whereas total fat mass did not differ significantly between study groups (Table 1). The percentage of limb fat was significantly reduced in LIPO patients compared to NONLIPO, consistent with lipodystrophy in LIPO patients. Several dysmetabolic features were apparent in LIPO patients, despite their fasting glucose being normal. LIPO patients displayed lower insulin stimulated glucose disposal both in the oxidative and non-oxidative pathway compared to NONLIPO. Fasting insulin, non-HDL-cholesterol, total leukocyte, lymphocyte and monocytes counts were increased in LIPO patients. Plasma TNF-α and plasma IL-6 were increased in LIPO patients, although the differences were not statistically significant. Duration of HIV infection, duration of HAART and CD4 cell number did not differ significantly between study groups. HIV-RNA was fully suppressed in both study groups (Table 1). Categorizing patients according to the Centers for Disease Control and Prevention (CDC) system of classification clinical stages A, B, and C, where C indicates AIDS diagnosis, did not reveal significant differences between LIPO and NONLIPO patients (Table 1).

All LIPO and NONLIPO patients were treated with nucleoside reverse transcriptase inhibitors (NRTIs) as part of HAART; which were respectively: lamivudine (83%, 83%), zidovudine (39%, 50%), stavudine (56%, 39%), and didanosine (6%, 11%). HIV-1 protease inhibitors (PIs) were used by 89% of LIPO and NONLIPO patients, that is indinavir (44%, 22%), ritonavir (22%, 39%), nelfinavir (22%, 22%), and saquinavir (17%, 11%), respectively.

Univariate correlation analyses revealed that suPAR correlated with the following parameters related to dysmetabolism:
1) suPAR correlated highly significantly with measures of fat distribution, insulin sensitivity and lipidemia independently of age in all patients (n=36, FIGS. 2A, 2B, 2C, and 2D, and Table 2)
2) suPAR correlated strongly and positively with TNF-α linking suPAR to a key mediator of inflammation. suPAR was surprisingly found to be a stronger predictor than TNF-α of fat distribution, insulin sensitivity and total cholesterol (Table 2 and Table 3)
3) suPAR correlated positively with leukocytes, lymphocytes, and monocytes establishing association to blood cells of importance for the immune activation and inflammatory status of the patient (Table 4).

TABLE 2

Linear correlation coefficients between suPAR and parameters of fat distribution, insulin sensitivity, lipidemia and immunology

| n = 36 | suPAR r-value | P |
|---|---|---|
| Limb fat (%) | −0.48 | <0.005 [b] |
| Body mass index | 0.19 | ns |
| Total fat mass (% of BW) | 0.11 | ns |
| $Rd_{clamp}$ | −0.58 | <0.001 [a] |
| $NOGM_{clamp}$ | −0.66 | <0.001 [b] |
| $GOX_{clamp}$ | 0.03 | ns |
| fP-Insulin | 0.58 | <0.001 [b] |
| fP-glucose | −0.11 | ns |
| Total cholesterol | 0.54 | <0.001 [a] |
| Non-HDL cholesterol | 0.51 | <0.005 [a] |
| Triglyceride | 0.22 | 0.19 |
| TNF-α | 0.54 | <0.001 [b] |
| IL-6 | 0.26 | 0.13 |
| CD4 | 0.06 | ns |
| Duration of HIV-infection | 0.20 | ns |
| Duration of NRTI therapy | 0.07 | ns |
| Duration of PI therapy | 0.14 | ns |
| Nadir CD4 | −0.20 | ns |
| HIV-RNA peak | −0.24 | 0.17 |

Abbreviations are given in Table 1;
[a] $P < 0.05$;
[b] $P < 0.01$ following adjustment for age (yr);
suPAR, triglyceride, TNF-α, IL-6 and HIV-RNA peak were log-transformed to obtain a normal distribution of these parameters

TABLE 3

Linear correlation coefficients between TNF-α and IL-6 versus parameters of fat distribution, insulin sensitivity, lipidemia and immunology

| n = 36 | TNF-α r-value | P | IL-6 | P r-value |
|---|---|---|---|---|
| Limb fat (%) | −0.34 | <0.05 | 0.08 | ns |
| $Rd_{clamp}$ | −0.25 | 0.15 | −0.13 | ns |
| $NOGM_{clamp}$ | −0.17 | ns | −0.33 | <0.05 |
| Total cholesterol | 0.44 | <0.01 [a] | 0.14 | ns |
| Non-HDL cholesterol | 0.49 | <0.005 [a] | 0.07 | ns |
| Triglyceride | 0.53 | <0.001 [c] | −0.03 | ns |

Abbreviations are given in Table 1;
[a] $P < 0.05$;
[c] $P < 0.001$, following adjustment for age (yr);
TNF-α, IL-6, triglyceride and relative increase in CD4 were log-transformed to obtain a normal distribution of these parameters

TABLE 4

Univariate correlations (Spearman ρ) between suPAR and blood cells, which are activators of immune and inflammatory response

| n = 36 | ρ |
|---|---|
| Correlations between suPAR and: | |
| Leukocytes | 0.48** |
| Neutrophils | 0.18 |
| Lymphocytes | 0.51** |
| Monocytes | 0.34* |

*$P < 0.05$;
**$P < 0.01$

Multiple regression analyses were undertaken to demonstrate that suPAR is a robust marker of key parameters of dysmetabolism. Non-oxidative glucose metabolism remained strongly correlated to suPAR ($R^2=0.43$, $P<0.001$) in a model where suPAR, age, TNF-α, IL-6, fasting triglyceride and non-HDL cholesterol were included. Most of the variation of non-HDL-cholesterol could be explained by fasting triglyceride and suPAR ($R^2=0.69$, $P<0.0001$) in a model where also age, TNF-α, and IL-6 were included as explanatory variables. Moreover, suPAR remained a significant marker of Rd ($R^2=0.33$, $P<0.001$) in a model, which included suPAR, age, TNF-α and IL-6.

Figure 3:
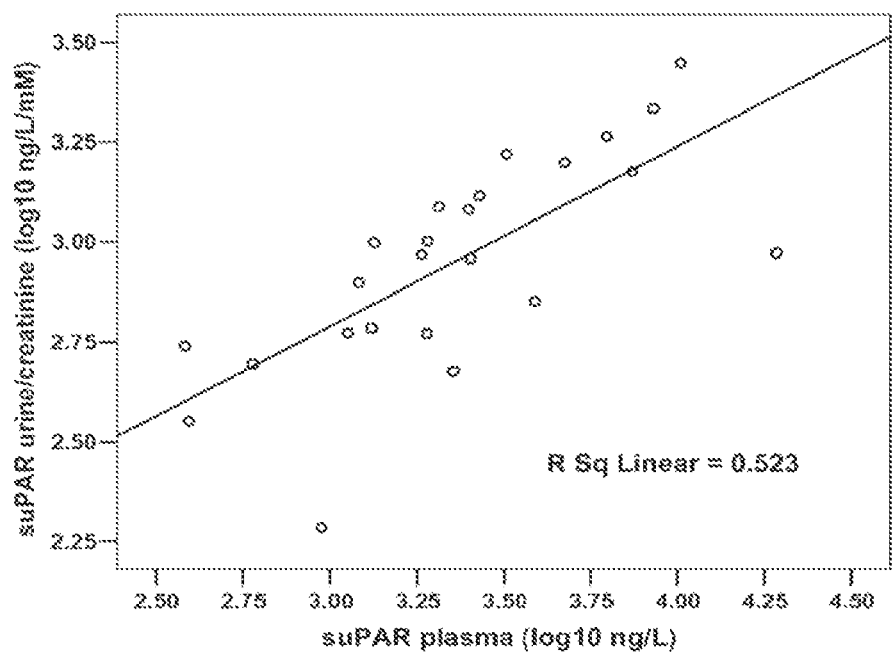
FIG. 3 shows linear correlation between fasting plasma suPAR versus overnight fasting urine suPAR corrected for urine creatinine in a sub-sample of 24 HIV-infected patients, where both scales are log transformed. The strength of the correlation is given as $R^2$.

FIG. 3 shows that fasting plasma suPAR and urine suPAR are highly correlated in HIV-infected patients on stable HAART. Since urine suPAR is shown to be a robust estimate of plasma suPAR, the level of suPAR can be performed on urine as well as plasma samples from such individuals. Urine suPAR corrected for urine creatinine has previously been shown to correlate positively and strongly with plasma suPAR in healthy individuals, and that diurnal changes in urine suPAR are small (Sier et al. 1999, Lab Invest 79:717-722).

The present data indicate that the circadian changes in plasma concentration of suPAR in HIV-infected patients on stable HAART are limited (FIG. 4).

Conclusion: The data shows that HIV-infected patients on HAART, who display a cluster of dysmetabolic features, are those with relatively high suPAR compared to treatment matched non-lipodystrophic HIV-infected patients. The fact that suPAR levels are strongly correlated with, respectively, the number of white blood cells, TNF-α, fat distribution, insulin sensitivity and lipidemia, emphasizes that suPAR is a significant link between immune constitution and metabolism in these patients. The present data show that suPAR is a stronger marker of metabolic syndrome in this patient group than TNF-α and IL-6.

The strong positive correlation between suPAR and TNF-α, which was observed in the present example, show that suPAR is a novel marker of a low-grade inflammatory state in HIV-infected patients on stable HAART regime, and hence diagnostic for this condition. Moreover, it was observed in the present study that suPAR correlated positively with leukocytes, lymphocytes and monocytes, which are themselves markers and effectors of low-grade inflammation. The density of uPAR at the cell surface of these blood cells is high, and much of plasma suPAR is thought to originate from these cells, which would be consistent with the present data.

Previous epidemiology studies have shown total leukocyte count and lymphocyte count to be inversely correlated with insulin resistance, and to be associated with an increased risk of developing diabetes type 2. It is suggested that chronic activation of the immune system may play a role in the pathogenesis of type 2 diabetes. The data in the present LIPO/NONLIPO HIV study show that suPAR is a novel marker of both low-grade inflammation and metabolic syndrome, supporting the conclusion that low-grade inflammation is a driving factor in the development of metabolic syndrome and thereby of diseases associated the metabolic syndrome, including type 2 diabetes and cardiovascular diseases in HIV patients.

Example 2 suPAR Carries Prediction Value in Healthy Individuals suPAR levels are shown to be a predictor of overall life expectancy.

Population group: The MONICA 10 cohort: In 1982 to 1984, 4807 individuals aged 30, 40, 50 or 60 years of age selected randomly from the population living in the vicinity of Glostrup University Hospital, Denmark, were invited to participate in a population survey. In 1993 to 1994, 4444 were re-invited and 2656 came and participated in subsequent investigations and gave blood. 2605 plasma samples from 1993/94 were available for the study.

SuPAR measurement: SuPAR was measured using the SuPARnostic™ kit (ViroGates, Copenhagen, Denmark), as described in Example 1. Briefly, the kit comprises an ELISA plate pre-coated with capture monoclonal antibody. According to the protocol, an HRP-labelled detection monoclonal antibody was added to the sample dilution buffer. Then 25 µl of plasma sample was mixed with 225 µl of dilution buffer and 100 µl aliquots (in duplicate) were aliquots into the wells of the ELISA plate and incubated for one hour. The ELISA plate was then washed, and then 50 µl substrate was added for 20 minutes and reaction stopped with 50 µl 0.5M $H_2SO_4$. Plates were measured at 450 nM. The kit intra-assay variation was 2.75% and inter-assay variation was 9.17%. 2605 samples were measured. The kit standard curve was validated to measure suPAR levels between 0.6 to 22.0 ng/ml. Three samples gave suPAR levels below (2) or above (1) the validated range and were excluded from the results.

Statistical analysis: Survival was analysed using univariate and multivariate Cox regression and Kaplan-Meier analysis. Differences between groups was analysed using the Mann-Whitney test. The statistical software SPSS version 13 was used for analysis. A p-value <0.05 was considered significant.

Results:

suPAR levels as a predictor of overall survival: Median suPAR in the 2602 individuals was 4.03 ng/ml plasma (range 1.3-19.9). SuPAR levels increased with age and were higher among women (N=1292, median suPAR 4.26, range 1.9-19.9) compared to men (N=1310, median suPAR 3.84, range 1.3-17.8), p<0.001 (FIG. 5A).

Overall survival: during the >10 year follow-up, 391 individuals died and 13 were lost to follow-up. Using cox-regression analysis, high suPAR was significantly associated with increased risk of mortality during follow-up (N=2602, RH=1.30 per ng suPAR increase, 95% Cl: 1.25-1.34). suPAR was associated with survival in both men (N=1310, RH=1.41, 95% Cl: 1.35-1.47) and women (1292, RH=1.23, 95% Cl: 1.16-1.31).

Univariate and multivariate analysis: Other markers that were associated with survival was age (RH per year older=1.10, 95% Cl: 1.09-1.14), LDL cholesterol (RH=1.002 per unit increase, 95% Cl: 1.001-1.002), non-smoking (RH=0.79, 95% Cl: 0.72-0.88) and sex (RH=0.613 for women compared to men, 95% Cl: 0.50-0.75). When all markers significant in univariate analysis were included in multivariate analysis, suPAR remained a significant and independent predictor of mortality (Table 5, RH per ng suPAR increase 1.22, 95% Cl: 1.67-1.28).

TABLE 5

Age-adjusted multivariate analysis

| | Variables in the Equation | | | | |
|---|---|---|---|---|---|
| | | | | 95.0% CI for Exp(B) | |
| | Wald | Sig. | Exp(B) | Lower | Upper |
| SuPAR (per ng/ml increase) | 73.5 | .000 | 1.219 | 1.165 | 1.275 |
| Sex | 28.7 | .000 | 1.780 | 1.441 | 2.197 |
| Age (per year older) | 248.1 | .000 | 1.102 | 1.088 | 1.115 |
| Smoking regularly | 36.3 | .000 | 1.884 | 1.534 | 2.315 |
| LDL-cholesterol (mmol/l) | 0.75 | .385 | .955 | .861 | 1.060 |

Figure 5B:
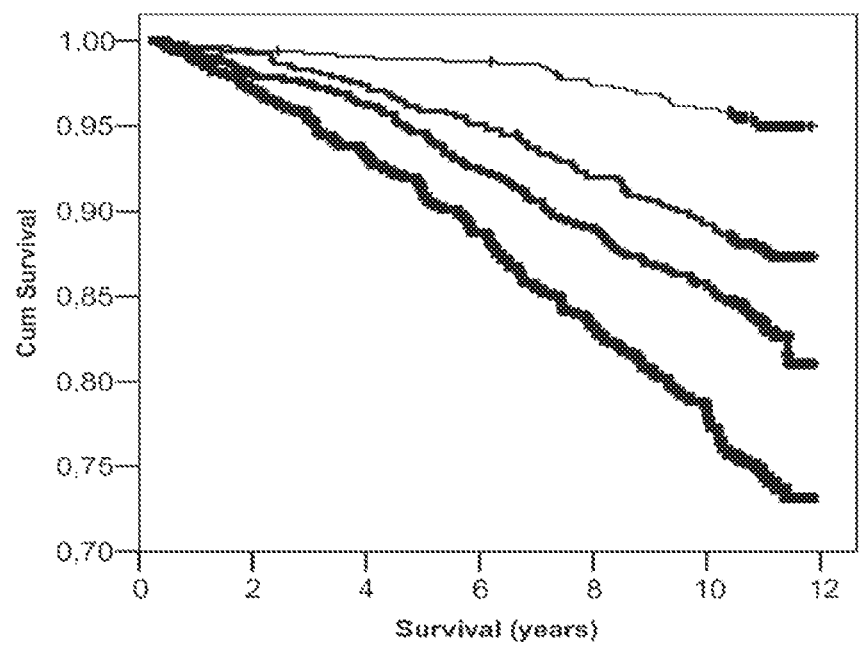

Kaplan-Meier analysis: In order to visualize the impact of suPAR on survival, suPAR values were divided into 3 equally sized groups; a low suPAR group (N=867, suPAR range 1.34-3.590 ng/ml), a medium suPAR group (N=868, range 3.591-4.56) and a high suPAR group (N=867, range 4.57-19.4). Kaplan-Meier analysis showed significant differences in survival between the 3 groups, with increasing mortality with increasing suPAR levels (p<0.001). Similarly, this was the case when dividing into 4 groups (FIGS. 5A and 5B).

Conclusion: suPAR levels in apparently healthy individuals are demonstrated to be strongly associated with mortality, independent of other markers. According to the Wald value obtained in multivariate analysis (Table 5) suPAR was the second strongest marker of mortality, after age. Thus, for a given age, sex and smoking status, suPAR significantly predicts the risk of mortality.

Example 3

SuPAR as a Marker for the Efficacy of Intervention

This example demonstrates the influence of life-style intervention on suPAR levels and thereby predicted disease risk of an individual.

Population group: MONICA 10 cohort as defined above in Example 2.

Methods: SuPAR was measured as described in Example 2.

Statistics: Comparison between groups was made using the Mann-Whitney test. Survival was analyzed using Cox regression analysis.

Results:

SuPAR is significantly associated an individuals smoking habit and with survival in both smokers and non-smokers: Of the 2602 individuals, 1091 were smokers, 1405 non-smokers and 106 occasional-smokers. Smokers had significantly higher suPAR levels compared to non-smokers and occasional-smokers (both p>0.001). There was no difference in suPAR levels between non-smokers and occasional-smokers (p=0.7).

Figure 6A:
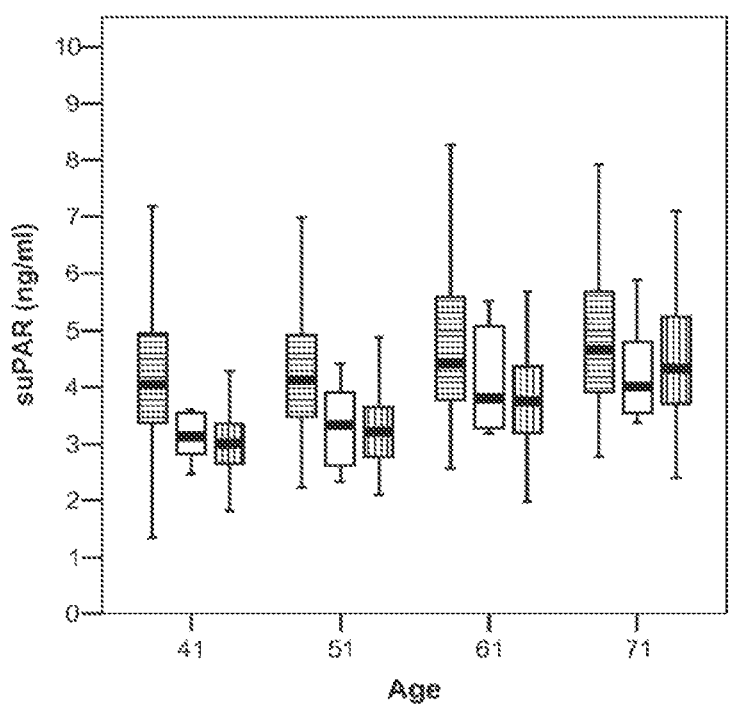

Smoking and suPAR levels among men: Male smokers had higher suPAR levels compared to non-smokers for all age groups (p<0.001, FIG. 6A). Among male smokers (N=580), 133 died during follow-up. suPAR was significantly associated with survival (Cox regression RH=1.32, 95% Cl: 1.24-1.41). Among male non-smokers men (N=674), 100 died during follow-up. SuPAR was significantly associated with survival (RH=1.73, 95% Cl: 1.57-1.90). 56 men were occasional-smokers and 6 died during follow-up. RH was 2.16, 95% Cl: 0.88-5.30).

Smoking and suPAR levels among women: Female smokers had higher suPAR levels compared to non-smokers for all age groups (p<0.001, FIG. 6B). Female smokers (N=511) had significantly higher suPAR than female occasional-smokers (N=56) (p<0.001), Mann-Whitney. Mean suPAR among female smokers was 5.11 (std 1.38) compared to female occasional-smokers (mean 3.99 ng/ml), std 0.93).

No difference in suPAR levels was observed between occasional-smokers (N=50) and non-smokers (N=731), Mann-Whitney p=0.79. Female smokers had higher suPAR (mean 5.11 ng/ml, std 1.38) compared to non-smokers (N=731, mean 4.07 std 1.14), p<0.001. Cox regression for female smokers showed that suPAR was significantly associated with survival. Among the 511 women, 72 died during follow-up. High suPAR was associated with decreased survival, RH=1.26, 95% Cl 1.10-1.45.

Among 731 female non-smokers, 73 died during follow-up. High suPAR was associated with decreased survival, RH=1.21, 95% Cl 1.11-1.31. 50 women were occasional-smokers and 5 died during follow-up, RH=2.91, 95% Cl 1.10-7.69.

Figure 6C:
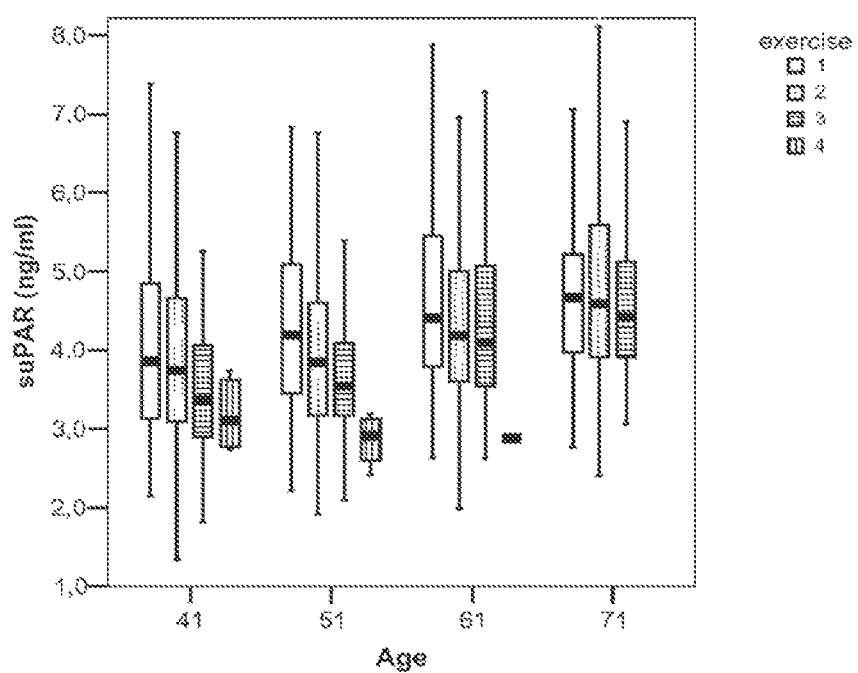

Exercise and suPAR: All individuals in the MONICA cohort were asked about their exercise habits. Individuals were grouped into four groups; Group 1 consisted of individuals reporting they did not exercise regularly (N=539), group 2 of individuals doing low-to moderate exercise (taking walk etc) (N=1454), group 3 of individuals exercising on a regularly basis (e.g. jogging) (N=546) and group 4 consisted of professional sportsmen (N=17). As exercise is age dependent, FIG. 6C shows suPAR levels among the different exercise groups according to age. In all age groups, except for 71-year old individuals, significantly lower suPAR levels were observed for individuals who exercised regularly compared to individuals who did not exercise (p<0.004 for all analysis). Correlation analysis adjusted for age and sex showed a significant negative correlation between exercise and suPAR (p<0.001, r=−012).

Conclusion: suPAR is shown to be a marker that changes with a change of lifestyle, namely individuals that do not smoke or have stopped smoking have significantly lower suPAR levels than individuals that continue to smoke. suPAR is elevated by a number of diverse diseases, which induce immune activation and, a high suPAR level is shown here to predict increased mortality.

suPAR is also shown to be a dynamic marker of life-style changes associated with exercise and physical fitness. Individuals that have high suPAR can lower their suPAR levels by exercise, an observation that was significant for all age individuals below 71 years of age, which in turn extends their life expectancy.

Example 4

SuPAR is a Risk Marker for Development of Cardiovascular Disease (CVD)

CVD is the most common cause of disease in the world. For example, in Sweden, non-communicable conditions account for 83% of all deaths; 41% of total deaths are due to cardiovascular diseases (CVD), 26% to cancer and about 7% to external causes (intentional and unintentional injuries).

Population group: Monica10 cohort as defined in Example 2.

Methods: suPAR measurement as in Example 2.

Statistics: One minus the Kaplan Meier estimator is shown for time until death. The cumulative incidence (probability of experiencing an event) is shown for time CVD. The cumulative incidence of CVD is estimated in a competing risks model with CVD, censoring due to death and censoring due to other reasons as the three competing causes. All analyses are stratified according to the quartiles of the distribution of suPAR. The quartile cut-offs were generated in the original 2602 patients and is 3.361 ng/ml (25%), 4.029 ng/ml (50%) and 4.910 ng/ml (75%). Follow-up on CVD event was available for analysis until $31^{st}$ of December 2001.

Figure 7:
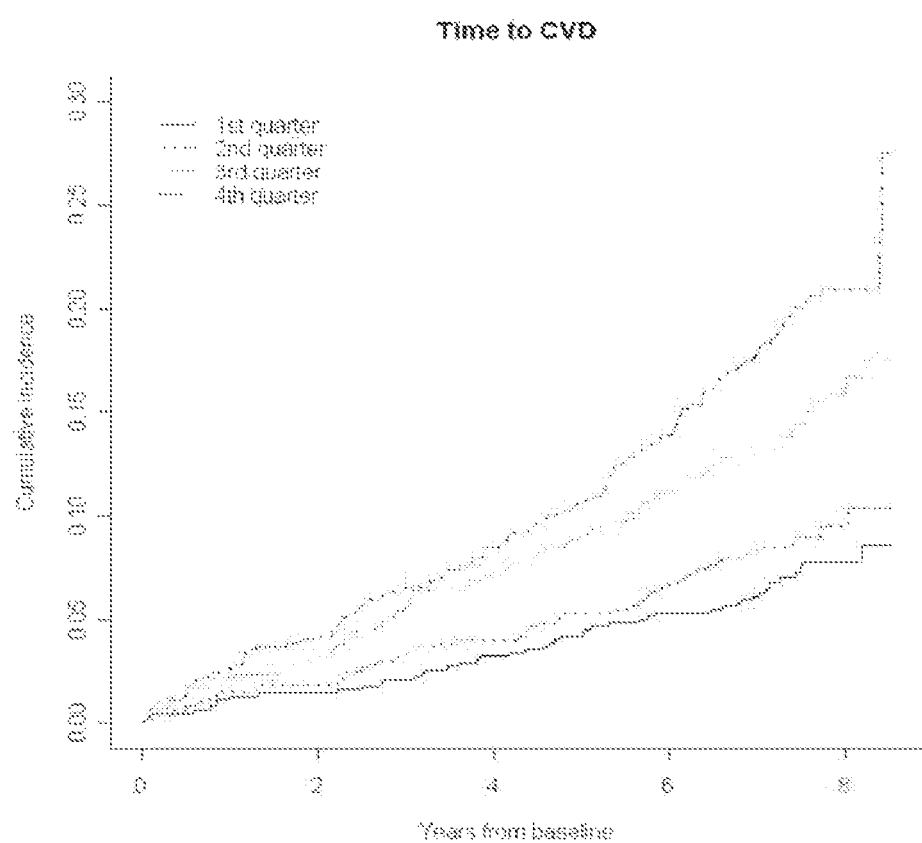
FIG. 7 shows the risk of developing a CVD as a competing risk model. Each line represents a suPAR quartile, with the first quartile being the lowest suPAR.

Results:

At the time of blood sampling, 208 individuals had already experienced a CDV, and were excluded from the analysis of risk of development of CVD. Those who had experienced a CVD before blood sampling had higher suPAR levels compared to those who had not experienced a CVD at time of blood sampling (Mann-Whitney, p<0.001). During the follow-up, 318 developed a CVD event, of which 70 events were an acute myocardial infarct. The risk of developing a CVD according to suPAR quartiles is shown as a competing risk model in FIG. 7.

suPAR is an independent predictor of risk of CVD: In multivariate analysis, data was available for analysis for a total of 2394 individuals, of whom 316 developed a CVD event. Using continuous suPAR values, suPAR remained a significant predictor of risk of CVD, when age, sex, smoking status and waist circumference are known (Table 6).

TABLE 6

Multivariate analysis of risk of developing CVD

| | Variables in the Equation | | | | |
| --- | --- | --- | --- | --- | --- |
| | | | | 95.0% CI for Exp(B) | |
| | Wald | Sig. | Exp(B) | Lower | Upper |
| SuPAR (ng/ml) | 19.290 | .000 | 1.153 | 1.082 | 1.229 |
| Sex | 6.623 | .010 | 1.400 | 1.083 | 1.808 |
| Age | 162.778 | .000 | 1.082 | 1.069 | 1.095 |
| Waist (cm) | 13.207 | .000 | 1.018 | 1.008 | 1.028 |
| Smoking regularly | 17.102 | .000 | 1.629 | 1.293 | 2.053 |

LDL-cholesterol was significantly associated with a risk of development of a CVD event in univariate Cox analysis, however it is not a significant predictor of CVD in multivariate analysis (Table 7).

TABLE 7

Multivariate analysis including LDL-cholesterol (mmol/l)

|  | Wald | Sig. | Exp(B) | 95.0% CI for Exp(B) Lower | Upper |
|---|---|---|---|---|---|
| suPAR_ng_ml | 20.950 | .000 | 1.158 | 1.088 | 1.233 |
| Sex | 6.510 | .011 | 1.397 | 1.081 | 1.807 |
| Age (per year older) | 146.721 | .000 | 1.079 | 1.066 | 1.093 |
| Waist (cm) | 14.740 | .000 | 1.020 | 1.010 | 1.030 |
| smoking | 16.466 | .000 | 1.619 | 1.283 | 2.044 |
| LDI-cholesterol (mmol/l) | 1.564 | .211 | 1.073 | .961 | 1.198 |

The metabolic syndrome was also independently associated with the development of CVD. When including the metabolic syndrome in the model, suPAR still remained a highly significant and independent predictor of other CVD events (multivariate analysis in Table 8).

TABLE 8

Multivariate analysis including the metabolic syndrome, defined according to the NCEP ATPIII 2001 definition with the 2004 glucose modification.

|  | Wald | Sig. | Exp(B) | 95.0% CI for Exp(B) Lower | Upper |
|---|---|---|---|---|---|
| suPAR_ng_ml | 19.542 | .000 | 1.154 | 1.083 | 1.229 |
| sex | 21.346 | .000 | 1.719 | 1.366 | 2.164 |
| Age (per year older) | 169.495 | .000 | 1.083 | 1.070 | 1.096 |
| Smoking regularly | 14.865 | .000 | 1.574 | 1.250 | 1.981 |
| Metabolic syndrome | 7.212 | .007 | 1.438 | 1.103 | 1.875 |

In a partial correlation analysis, controlling for sex and age, suPAR showed little or no correlation to other known markers of risk of CVD, including body mass index (BMI), LDL-cholesterol and triglycerides (Table 9).

TABLE 9

Partial correlation between suPAR and known risk markers of CVD adjusted for sex and age.

| Control Variables | | | |
|---|---|---|---|
| SEX & AGE | SuPAR (ng/ml) | Correlation | 1.000 |
| | | Significance (2-tailed) | .0 |
| | | df | |
| | Regular Smoker (yes or no) | Correlation | −.383 |
| | | Significance (2-tailed) | .000 |
| | | df | 2550 |
| | White blood cells | Correlation | .355 |
| | | Significance (2-tailed) | .000 |
| | | df | 2550 |
| | LDL-cholesterol | Correlation | −.003 |
| | | Significance (2-tailed) | .896 |
| | | df | 2550 |
| | Triglyceride | Correlation | .097 |
| | | Significance (2-tailed) | .000 |
| | | df | 2550 |
| | Waist circumference | Correlation | .027 |
| | | Significance (2-tailed) | .172 |
| | | df | 2550 |

TABLE 9-continued

Partial correlation between suPAR and known risk markers of CVD adjusted for sex and age.

| Control Variables | | | |
|---|---|---|---|
| | Systolic blood pressure | Correlation | .042 |
| | | Significance (2-tailed) | .032 |
| | | df | 2550 |
| | Fasting glucose | Correlation | .081 |
| | | Significance (2-tailed) | .000 |
| | | df | 2550 |

Conclusion. suPAR is shown to be a surprisingly strong and independent risk marker of development of a CVD event in apparently healthy individuals. Independent of sex, age, smoking status and the metabolic syndrome, a 1 ng/ml increase in suPAR levels was associated with a 15.4% increased risk (CI95: 8.4 to 22.8%, P<0.001) of developing a CVD during the follow-up. Interestingly, suPAR is not, or only weakly, correlated to classical predictors of CVD development, strengthening the strong and independent role of suPAR as a risk marker for CVD.

Example 5

The Plasma suPAR Level is Diagnostic of Low-Grade Inflammation and a Independent Predictor of Development of Diabetes Type 2

The number of individuals that develop diabetes (type 2 diabetes) has increased in the last decades. There is a higher prevalence of diabetes in overweight individuals. However, not all overweight individuals develop diabetes. Thus, there is a need for markers to predict the risk of an individual developing diabetes independently of BMI.

Population group: Monica10 cohort as defined in Example 2.

Methods: suPAR determination as in Example 2; Metabolic syndrome was defined according to the NCEP ATPIII 2001 with the glucose modification of 2004. At baseline, 425 (16.3%) had the metabolic syndrome.

Results: At the time of blood sampling of the Monica10 cohort, 34 individuals had been diagnosed with diabetes according to ICD-8 and -10 codes. These individuals had significantly higher suPAR levels compared to those who did not have diabetes at time of inclusion (Mann-Whitney, p<0.001). During the follow-up period, 65 out of 2568 individuals, who had not previously been diagnosed with diabetes I or II, went on to develop diabetes.

Figure 8:
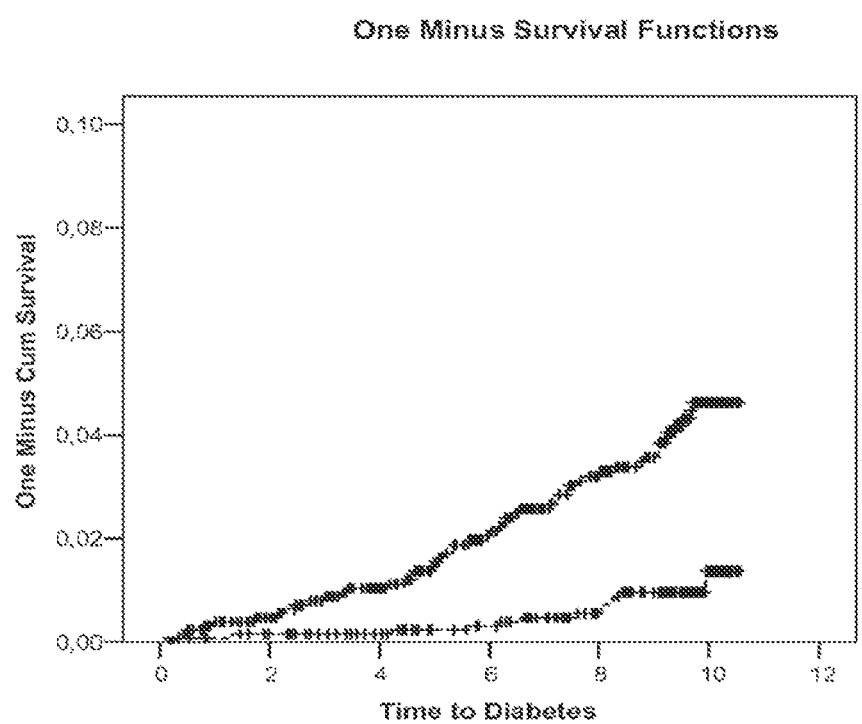
FIG. 8 shows a risk analysis of diabetes according to median suPAR at inclusion. Upper continuous line (with high risk) represents individuals with suPAR above-median, while lower line (dotted line) individuals with suPAR below-median.

When the original cohort (2602 individuals) was divided into 2 groups, based on median suPAR, significantly more individuals having suPAR levels above the median went on to develop diabetes (log rank test, p<0.001, inverse Kaplan Meier plot, FIG. 8).

Multivariate analysis of risk of diabetes: Smoking was not associated with a risk of developing diabetes. In univariate analysis, high suPAR, age (older), sex (being a man) and having a high BMI were significantly associated with an increased risk of developing diabetes. In multivariate analysis (Table 10), these latter factors all remained significantly associated with the risk of developing diabetes.

TABLE 10

Multivariate analysis of univariate significant predictors of development of diabetes

| Variables in the Equation | | | | 95.0% CI for Exp(B) | |
|---|---|---|---|---|---|
| | Wald | Sig. | Exp(B) | Lower | Upper |
| Systolic blood pressure | 6.895 | .009 | 1.019 | 1.005 | 1.034 |
| SuPAR (ng/ml) | 19.551 | .000 | 1.247 | 1.131 | 1.376 |
| sex | 9.547 | .002 | 2.326 | 1.362 | 3.974 |
| Age (per year older) | 6.510 | .011 | 1.037 | 1.008 | 1.066 |
| BMI | 26.968 | .000 | 1.138 | 1.084 | 1.195 |

Leukocyte Count as Predictor of Development of Diabetes Mellitus—the Strength of SuPAR: Number of White blood cells (WBC), i.e. leukocytes, which is accepted as a marker for immune activation and low-grade inflammation in the general population, has been shown to significantly predict development of diabetes mellitus (Vozarova B et al., 2002, Diabetes 51:455-461). WBC count showed a strong positive correlation to suPAR level both univariate (r=0.34, P<0.0001) and after correction for gender and age (partial correlation r=0.35, P<0.0001) in the MONICA 10 cohort. Thus, suPAR may be regarded as a marker for immune activation and low-grade inflammation in the general population. Substituting suPAR by WBC count in Table 10, WBC was associated with an increased risk of developing diabetes mellitus independent of age, sex and metabolic syndrome of 13% per $10^9$ WBC per Liter (95% Cl: 0% to 26%, P<0.05). However, taking both suPAR and WBC values, WBC was not-significant (P=0.), whereas suPAR remained strongly associated with an increased risk of developing diabetes (27% per 1 ng/mL increase in plasma suPAR, 95% Cl: 13% to 43%, P<0.0001). Thus, suPAR is a stronger predictor of diabetes than WBC.

Conclusion. These data show that suPAR is an independent predictor of the risk of developing diabetes. When age, sex and the metabolic syndrome is known, a 1 ng/ml increase in suPAR was associated with a 28% increased risk of developing diabetes (95% Cl 15-43%). In addition, these data provide evidence that suPAR correlate strongly with WBC count independently of age and gender, thus establishing suPAR as a marker of immune activation and low-grade inflammation in the general population. Excluding individuals who had baseline blood sugar levels above 6.9 mM or used insulin did not change the significance of suPAR in relation to development of diabetes Example 6

SuPAR is a Marker of the Metabolic Syndrome

Population group: Monica 10 cohort as defined in Example 2.

Methods: suPAR determination as in Example 2. The metabolic syndrome was defined according to the NCEP ATPIII 2001 definition with the 2004 glucose modification (Grundy S M et al., 2005, Circulation 112: 2735-2752). The distribution of the 2602 individuals into 5 metabolic classes, identified as having none or 1-5 components of the metabolic syndrome is shown in Table 11. The 5 components are: Elevated waist circumference: Men—Equal to or greater than 40 inches (102 cm) and Women—Equal to or greater than 35 inches (88 cm); Elevated triglycerides: Equal to or greater than 150 mg/dL; Reduced HDL ("good") cholesterol: Men—Less than 40 mg/dL, Women—Less than 50 mg/dL; Elevated blood pressure: Equal to or greater than 130/85 mm Hg; Elevated fasting glucose: Equal to or greater than 100 mg/dL, (based on the definition provided by (NCEP) Adult Treatment Panel III (ATP III), with minor modifications comprising).

TABLE 11

Distribution of metabolic syndrome and suPAR values among 2602 individuals

| Number of Metabolic syndrome components | Frequency | Percent | Mean suPAR (ng/ml) |
|---|---|---|---|
| 0 | 748 | 29.2 | 3.97 |
| 1 | 816 | 32.7 | 4.27 |
| 2 | 548 | 21.8 | 4.47 |
| 3 | 315 | 11.4 | 4.52 |
| 4 | 136 | 4.6 | 4.65 |
| 5 | 39 | 0.4 | 4.80 |
| Total | 2602 | 100.0 | |

Figure 9:
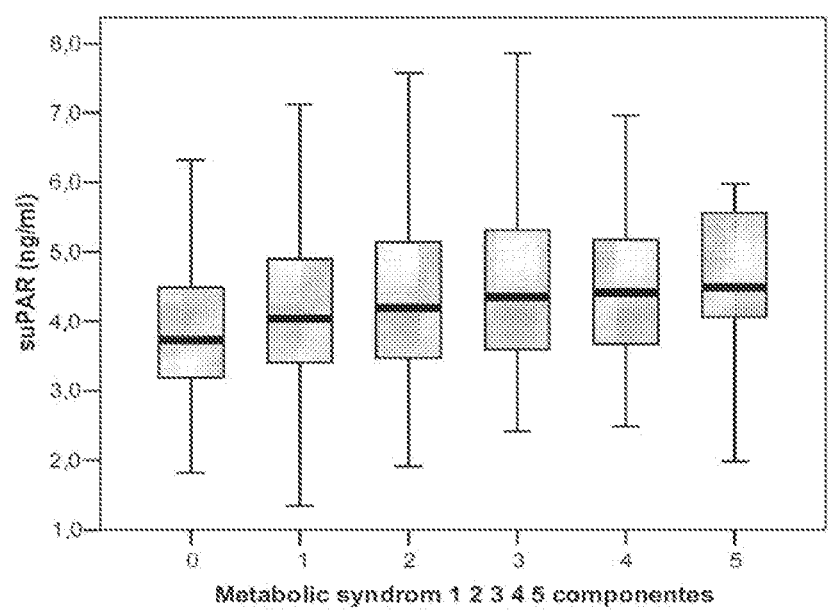
FIG. 9 shows the relationship of suPAR levels to a number of components of metabolic syndrome in a subject, the components being one or more of: Elevated waist circumference: Men—Equal to or greater than 40 inches (102 cm) and Women—Equal to or greater than 35 inches (88 cm); Elevated triglycerides: Equal to or greater than 150 mg/dL; Reduced HDL ("good") cholesterol: Men—Less than 40 mg/dL, Women—Less than 50 mg/dL; Elevated blood pressure: Equal to or greater than 130/85 mm Hg; Elevated fasting glucose: Equal to or greater than 100 mg/dL
Figure 10:
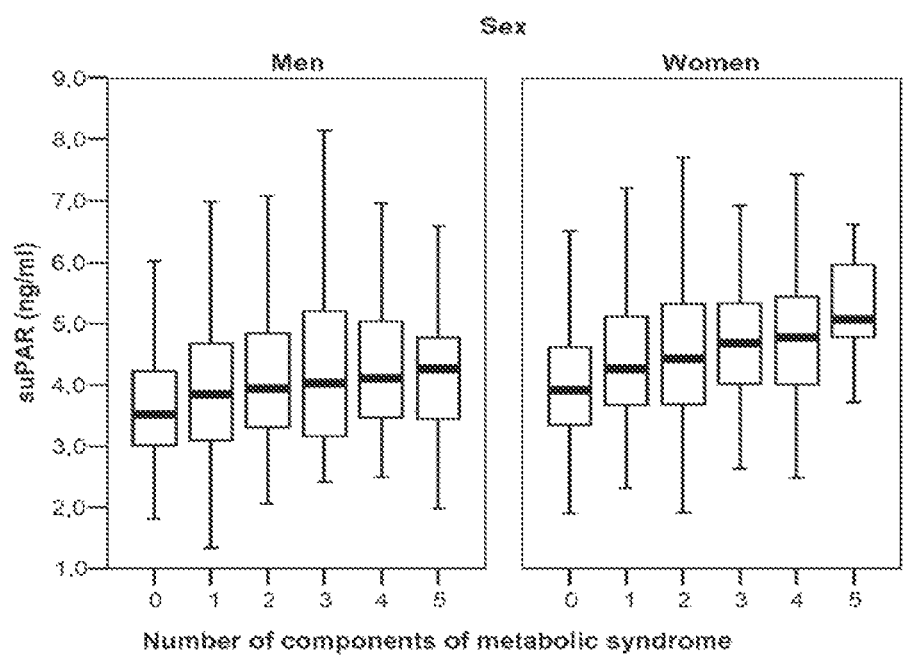
FIG. 10 shows the relationship of suPAR levels and number of components (as in FIG. 9) of metabolic syndrome of a subject according to sex.

Results: SuPAR levels increased as the number of components of metabolic syndrome in an individual increased. Individuals with no components of the metabolic syndrome (O) had significantly lower suPAR levels compared to individuals that had one or more components (Table 11 and FIG. 9), p<0.001 Mann Whitney u test. This was the case for both men and women (FIG. 10). In univariate Pearson correlation suPAR (log transformed) correlated positively with an increasing number of metabolic components (r=0.17, P<0.0001), a correlation, which remained highly significant after correction for age and gender (partial correlation r=0.13, P<0.0001).

Conclusion: SuPAR is a strong marker of the metabolic syndrome independent of age and gender. suPAR was also shown to correlate significantly with an increasing fasting glucose (Table 9). In Example 5 it was demonstrated that suPAR strongly predicts diabetes type 2. From these observations it is deduced that suPAR is a strong marker of insulin resistance, which is an underlying cause of the metabolic syndrome and type 2 diabetes mellitus.

Example 7

SuPAR as a Marker of Ischemic Heart Disease as a Component of CVD

SuPAR is shown to be a predictive marker of the future development of Ischemic Heart Disease (IHD), classified as a component of CVD.

Population group: Monica 10 cohort as defined in Example 2

Methods: suPAR determination as in Example 2.

Results: Of the 2534 individuals without a previous IHD, 115 developed IHD during the follow-up. Multivariate cox regression analysis showed that a 1 ng/ml suPAR increase, independent of sex, age, smoking status and presence of the metabolic syndrome, was associated with a 16.7% (Cl95: 4.8 to 29.9%, P=0.005) increased risk for developing IHD. Of the 115 individuals that developed an IHD, 9 had previously developed diabetes. When these 9 individuals were excluded from the analysis, suPAR still remained significantly and independently associated with risk of IHD.

Age-Adjusted Multivariate Cox Regression Analysis for Risk of IHD: In an age adjusted Cox regression analysis, a 1 ng/ml increase in suPAR was associated with an increased risk of IHD of 21% (RH=1.21, 95% CI: 1.09-1.35), having the metabolic syndrome increased risk with 61% (RH=1.61, 95% CI 1.00-2.80), being female compared to male decreased risk with 61% (RH=0.39, 95% CI 0.25-0.60), being a non-smoker compared to smoker decreased risk with 33% (RH=0.67, 95% CI 0.54-0.84), and an increase in LDL cholesterol (per 10 mM increase) with a 3.5% increase in risk (RH=1.035, 95% CI: 1.02-1.05).

Figure 11:
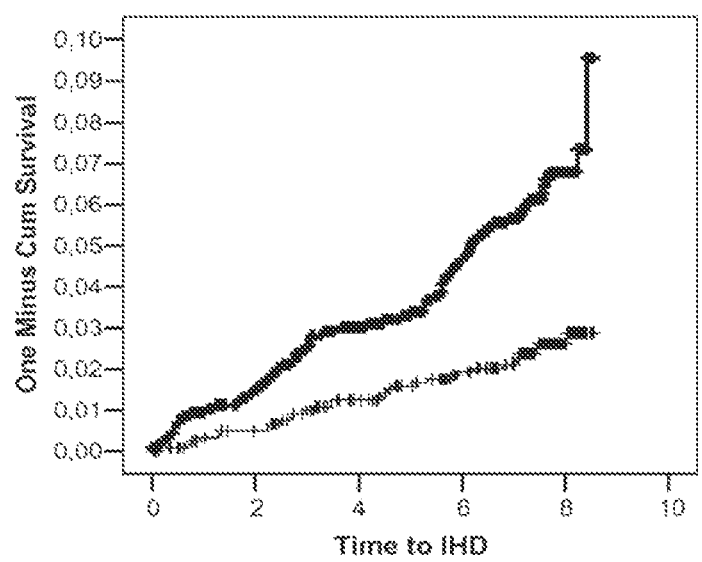
FIG. 11 shows the risk of developing an IHD during follow-up. Fat line indicates individuals with suPAR above-median (4.03 ng/ml). Thin line indicates individuals with suPAR below-median. The difference was statistically significantly (p<0.001, log-rank test).

Kaplan Meier Analysis: In order to carry out Kaplan-Meier analysis, individuals were divided into 2 groups based on the median suPAR value of the 2602 individuals included in study (4.03 ng) (FIG. 11).

Conclusion: The results indicate that the suPAR level is a significant predictor of the risk of developing an IHD, as a component of CVD, in individuals who have not previously experienced an AMI. SuPAR predicted the risk of IHD independently of other classical markers of IHD.

Example 8

Algorithm for the Prediction of the Risk of Developing CVD or Diabetes Mellitus Type II A combination of factors, one of which being suPAR, are predictive of the risk of developing CVD or Type II Diabetes. In one embodiment stepwise backward logistic regression was employed to identify those factors that have the highest statistical significance in predicting the outcome of a large number of human subjects, and the risk of developing each of these diseases. The combination of predictive factors or criteria provides a model employed in the form of an algorithm for predicting the health risks of an individual subject.

Stepwise, Backwards Regression Analysis

The following univariate parameters were significantly associated with the future development of a CVD: suPAR (RH (RH=Hazard ratio) per ng increase 1.23 (95% CI: 1.18-1.29)), Hypertension (RH=2.45 (95% CI: 1.93-3.10)), Asthma (RH=1.60 (95% CI: 1.12-2.30)), Diabetes (RH=3.19 (95% CI: 2.01-5.08)), snaps drinking (RH per glass increase 1.03 (95% CI: 1.01-1.04)), smoking (RH=1.19 (95% CI: 1.08-1.34)), red blood cell count (RH=1.05 (95% CI: 1.02-1.08)), Presence of the metabolic syndrome (RH=1.73 (95% CI: 1.33-2.25)), Total cholesterol (RH per mmol/l increase=1.002 (95% CI: 1.001-1.003)), LDL-cholesterol (RH per mmol/l increase 1.003 (95% CI: 1.001-1.004)), Triglycerides (RH per mmol/l increase 1.001 (95% CI: 1.000-1.002)), Diastolic blood pressure (RH per si (Si pressure unit) increase 1.04 (95% CI: 1.03-1.06)), Systolic blood pressure (RH per si increase 1.036 (95% CI: 1.030-1.041)), Age (RH per year increase 1.08 (95% CI: 1.07-1.10)), Fasting glucose level (RH=1.02 (95% CI: 1.015-1.026)), Receiving asthma treatment (RH=1.56 (95% CI: 1.07-2.29)), Sex (men vs women, RH=1.62 (95% CI: 1.30-2.03)).

Figure 12:
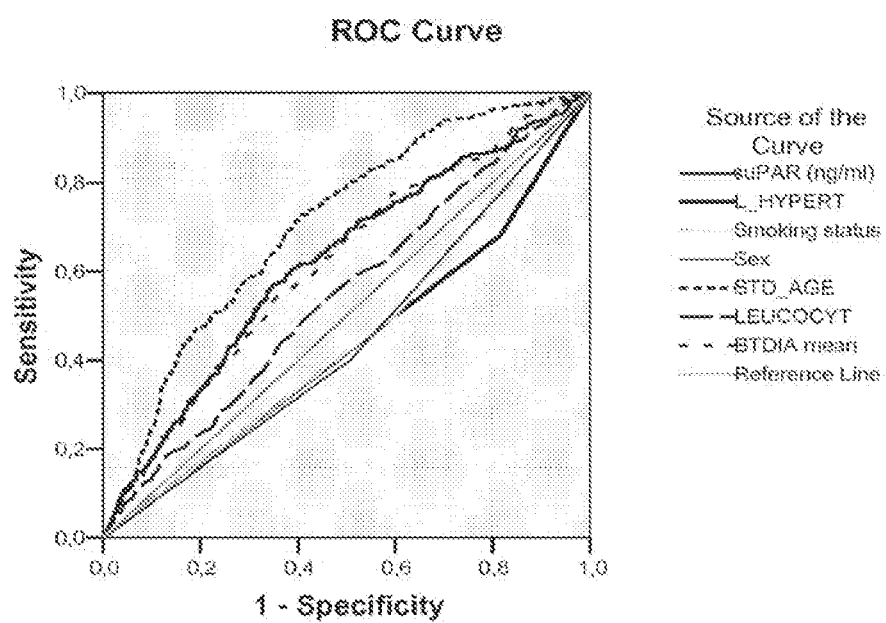
FIG. 12 shows ROC analysis of variables significant for development of CVD in multivariate analysis.
Figure 13:
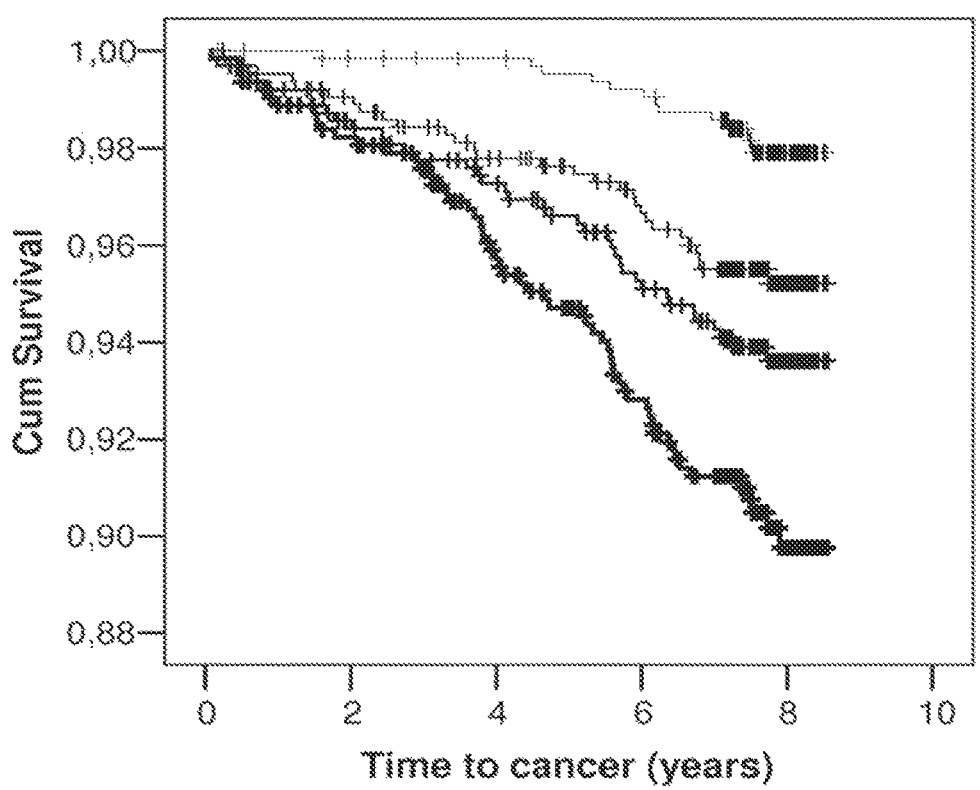
FIG. 13 shows Kaplan Meier analysis of time to cancer diagnosis. The thin upper line represents the lowest suPAR quartile, the one below (median thin line) represents the second lowest suPAR quartile, the medium thick line represents the second highest suPAR quartile and the fattest (bottom line) represents the highest suPAR quartile. P<0.001, log rank test.

Multivariate analysis: All the univariate significant data were then entered into a multivariate analysis. The multivariate analysis is shown in Table 12. Those factors significant in Table 12 were then entered into a new multivariate analysis (Table 13). The different parameter's ability to predict the event of CVD within 8 years from blood sampling were analysed using receiver operating characteristic curves (ROC), as shown in FIG. 12. According to the area under curve (AUC), age, followed by suPAR were the best predictors of the future development of CVD (Table 14). Combining information from all the parameters that were significant in multivariate analysis will improve the predictive accuracy for development of a future CVD. Identifying the linear combination of the parameters yielding the highest AUC can be carried out using the method by Xiong et al., 2004, Med. Decision Making; 24:659-69 based on Fisher's Z-transformation. This way, additional data can be added to the algorithm, also parameters not yet discovered or included in the current model to increase the combined AUC. Furthermore, data can also be omitted from the model if not available. For example, if fasting glucose data are not available, the model can be used with the available data. The result of the model is a risk output, which can be in % risk or as a calculated age (which can then be compared to the age of the patient). If the risk is higher than normal, the calculated age will be higher then the individual's age.

TABLE 12

Multivariate analysis per 1 unit change of parameters significantly associated with risk of development of CVD in univariate analysis.

|  |  |  |  | 95.0% CI for Exp(B) | |
| --- | --- | --- | --- | --- | --- |
|  | Wald | Sig. | Exp(B) | Lower | Upper |
| Diastolic blood pressure | 7.539 | .006 | 1.027 | 1.008 | 1.047 |
| SuPAR (ng/ml) | 11.342 | .001 | 1.135 | 1.054 | 1.221 |
| Sex | 12.078 | .001 | 1.629 | 1.238 | 2.146 |
| Age | 89.715 | .000 | 1.074 | 1.059 | 1.091 |
| Asthma | .114 | .735 | 1.129 | .559 | 2.278 |
| Alcohol consumption | 1.146 | .284 | 1.014 | .989 | 1.039 |
| Treatment for asthma | .683 | .409 | 1.368 | .650 | 2.882 |
| Smoking | 17.159 | .000 | 1.340 | 1.167 | 1.541 |
| LDL-cholesterol | .080 | .778 | 1.000 | .997 | 1.004 |
| Triglycerides | .538 | .463 | 1.001 | .999 | 1.002 |
| Total cholesterol | .067 | .796 | 1.000 | .997 | 1.004 |
| Leucocytes | 5.288 | .021 | 1.008 | 1.001 | 1.015 |
| Red blood cell count | .014 | .906 | 1.002 | .968 | 1.037 |
| Diabetes | 1.585 | .208 | 1.501 | .797 | 2.833 |
| Hypertension | 4.096 | .043 | 1.340 | 1.009 | 1.779 |
| Systolic blood pressure | 1.255 | .263 | 1.006 | .995 | 1.017 |
| Fasting glucose level | 3.039 | .081 | 1.009 | .999 | 1.019 |

TABLE 13

Multivariate analysis of parameters significantly associated with CVD from Table 12.

|  |  |  |  |  | 95.0% CI for Exp(B) | |
| --- | --- | --- | --- | --- | --- | --- |
|  | Wald | df | Sig. | Exp(B) | Lower | Upper |
| Diastolic blood pressure | 26.545 | 1 | .000 | 1.033 | 1.020 | 1.045 |
| SuPAR (ng/ml) | 15.132 | 1 | .000 | 1.145 | 1.070 | 1.227 |
| Sex | 16.752 | 1 | .000 | "1.629 | 1.289 | 2.053 |
| Age | 160.881 | 1 | .000 | 1.082 | 1.069 | 1.096 |
| Smoking | 17.426 | 1 | .000 | 1.290 | 1.601 | 1.516 |
| Leucocytes | 4.131 | 1 | .042 | 1.007 | 1.000 | 1.013 |
| Hypertension | 9.908 | 1 | .002 | 1.536 | 1.176 | 2.008 |

TABLE 14

Area under curve for the data corresponding to FIG. 12
Area Under the Curve

| Test Result Variable(s) | Area | Std. Error(a) | Asymptotic Sig.(b) | Asymptotic 95% Confidence Interval | |
|---|---|---|---|---|---|
| | | | | Lower Bound | Upper Bound |
| suPAR (ng/ml) | .620 | .017 | .000 | .587 | .653 |
| Hypertension | .432 | .018 | .000 | .397 | .467 |
| Smoking status | .451 | .017 | .005 | .417 | .485 |
| Sex | .446 | .017 | .002 | .413 | .480 |
| Age | .705 | .015 | .000 | .677 | .734 |
| Leucocytes | .546 | .017 | .008 | .512 | .580 |
| Diastolic blood pressure | .616 | .017 | .000 | .583 | .648 |

Example 9

Computer Implemented Assessment of the Risk of Mortality and/or Development of CVD, Diabetes Type 2, and/or Cancer Development of a statistical algorithm for assessment of a patient's risk of mortality and/or developing CVD, cancer or type 2 diabetes within a specified time in which suPAR is a parameter is set out below. The calculation can be executed in a standard computer program like a Microsoft Excel spreadsheet.

In the present example, the algorithm is based on the data set of covariates determined for subjects in the MONICO10 cohort as set out in Examples 2 and 10, and it has been applied separately for the four different endpoints, time until CVD, cancer, diabetes and death. The algorithm builds on a so-called Proportional Hazards Model, which is a statistical model developed in the statistical field of Survival Analysis. The Baseline Hazard Function is chosen to be a power function, and it yields Weibull distributed event times. The underlying time scale is age, and the event times are left-truncated and right-censored.

The algorithm produces separate estimates of the risk of acquiring CVD, cancer or diabetes or of dying within a specified time, as a function of an individual's characteristics (from hereon termed "covariates"). These risk estimates are obtained by inserting estimated effects of the covariates obtained from the model in the following expression:

$$P = 1 - \exp(-(\exp(a^* \log(age+t)) - \exp(a^* \log(age)))^* \exp(z^* beta - a^* \log(b)))$$

where a, b and beta are estimates of the shape and scale parameters and the effect of the covariates, respectively, obtained from fitting the data to the model, e.g. by using Maximum Likelihood Estimation.

The variables "age", t and z contain the covariates from a (possibly fictitious) individual for whom the risk of acquiring CVD, cancer or diabetes or of dying can be estimated. P is the probability of the individual acquiring CVD, cancer or diabetes or of dying within t years, "age" is the current age of the individual, and z is a vector containing all other covariates included in the model to calculate the probability.

The risk estimates depend on which covariates are included in the model, on the endpoint and on the estimates of a, b and beta. The core covariates for each risk assessment are as follows:

Time until CVD: Age, sex, suPAR, smoker/occasional or non-smoker, systemic/diastolic blood pressure, waist circumference, HDL-cholesterol, LDL-cholesterol;

Time until cancer: Age, sex, smoker/occasional or non-smoker, suPAR;

Time until diabetes: Age, sex, fasting blood glucose, suPAR;

Time until death: Age, sex, smoker/occasional or non-smoker, suPAR, systemic/diastolic blood pressure, waist circumference.

Furthermore, in addition to the covariates shown above, the model allows for further covariates to be added e.g. (total-cholesterol, triglyceride, hs-CRP, NTproBNP, BMI, physical activity, alcohol intake and genetic polymorphisms associated with risk of disease). Interactions between the covariates may be included in the model as well.

In the following, four examples are given, one for each endpoint. Algorithms with fewer covariates are easily included in the model by omitting z's and betas, and interactions are included by introducing more z's and betas. In all examples, the individual considered is a 58 year old man with a suPAR measurement of 3.0 ng/ml. The risk that is assessed is the risk of experiencing an event within 10 years. The working range for each parameter is given by the 95% confidence interval, which is the interval from the estimate minus twice its standard error to the estimate plus twice its standard error ([est.−2*s.e.;est.+2*s.e.]). In the examples, a standard error (s.e.) provided (in parenthesis) each time an estimate is shown.

Time until CVD: The estimates are as follows: beta1=0.13 (0.03) (one unit increase of suPAR concentration), beta2=0.38 (0.14) (male vs. female), beta3=−0.14 (0.33) (occasional vs. no smoking), beta4=0.66 (0.12) (regular vs. no smoking), beta5=0.007 (0.005) (one mm Hg increase in systolic blood pressure), beta6=0.029 (0.009) (one mm Hg increase in diastolic blood pressure), beta7=0.009 (0.006) (one cm increase in waist measurement), beta8=0.64 (1.58) (one unit increase of HDL-cholesterol) and beta9=0.50 (0.58) (one unit increase of LDL-cholesterol). The logarithm of the shape parameter is log(a)=1.75 (0.08), and the logarithm of the scale parameter is log(b)=5.34 (0.17).

According to the formula, if the man is a non-smoker with a blood pressure of 160/120, a waist circumference of 100 cm, an HDL measurement of 0.14 and an LDL measurement of 0.4, he has a risk of P=45.3% of getting CVD within 10 years. Had he been 48 years of age, his risk would have been 23.4%. His risk of getting CVD within 5 years is P=21.8%. The corresponding risk of a female is 33.8% within 10 years. Had the man had a suPAR measurement of 2.0 ng/ml then he would have had a probability of 41.1% of getting CVD within 10 years, and if it was 4.0 ng/ml it would have been 49.8%. If the man would start smoking regularly, he would increase his risk of getting CVD within 10 years to 68.9%. If the man would bring his blood pressure down to 120/80, he would lower his risk of getting CVD within 10 years to 13.4%. If he could decrease his waist by 5 cm, he would lower his risk to 43.9%. If he could increase his HDL measurement to 0.15, he would obtain a risk of 45.5%, and if he could lower his LDL measurement to 0.3 he would obtain a risk of 43.7%.

Time until cancer: The estimates are as follows: beta1=0.25 (0.05) (one unit increase of suPAR concentration), beta2=0.08 (0.17) (male vs. female), beta3=0.04 (0.52) (occasional vs. no smoking) and beta4=0.62 (0.19) (regular vs. no smoking). The logarithm of the shape parameter is log(a)=4.83 (0.07), and the logarithm of the scale parameter is log(b)=1.73 (0.10).

According to the formula, if the man is a non-smoker, he has a risk of P=4.2% of getting cancer within 10 years. Had he been 48 years of age, his risk would have been 1.9%. His risk of getting cancer within 5 years is P=1.7%. The corresponding risk of a female is 3.9% within 10 years. Had the man had a suPAR measurement of 2.0 ng/ml then he would have had a probability of 3.3% of getting cancer within 10 years, and if it was 4.0 ng/ml it would have been 5.3%. If the man would start smoking regularly, he would increase his risk of getting cancer within 10 years to 7.6%.

Time until diabetes: The estimates are as follows: beta1=0.22 (0.06) (one unit increase of suPAR concentration), beta2=0.79 (0.27) (male vs. female) and beta3=0.45 (0.03) (one unit increase of fasting glucose. The logarithm of the shape parameter is log(a)=5.81 (0.32), and the logarithm of the scale parameter is log(b)=1.45 (0.20).

According to the formula, if the man has a fasting glucose of 5, he has a risk of P=2.3% of getting diabetes within 10 years. Had he been 48 years of age, his risk would have been 1.3%. His risk of getting diabetes within 5 years is P=1.0%. The corresponding risk of a female is 1.0% within 10 years. Had the man had a suPAR measurement of 2.0 ng/ml then he would have had a probability of 1.8% of getting diabetes within 10 years, and if it was 4.0 ng/ml it would have been 2.8%. If the man were able to lower his fasting glucose level to 4, his risk of getting diabetes would decrease to 1.5%.

Time until death. The estimates are as follows: beta1=0.20 (0.03) (one unit increase of suPAR concentration), beta2=0.49 (0.12) (male vs. female), beta3=-0.12 (0.33) (occasional vs. no smoking), beta4=0.72 (0.11) (regular vs. no smoking), beta5=-0.001 (0.004) (one mmHg increase in systolic blood pressure), beta6=0.021 (0.007) (one mm Hg increase in diastolic blood pressure) and beta7=0.002 (0.005) (one cm increase in waist measurement). The logarithm of the shape parameter is log(a)=2.01 (0.06), and the logarithm of the scale parameter is log(b)=4.89 (0.08).

According to the formula, if the man is a non-smoker with a blood pressure of 160/120 and a waist circumference of 100 cm, he has a risk of P=16.9% of dying within 10 years. Had he been 48 years of age, his risk would have been 5.9%. His risk of dying within 5 years is P=6.7%. The corresponding risk of a female is 10.7% of dying within 10 years. Had the man had a suPAR measurement of 2.0 ng/ml then he would have had a probability of 14.1% of dying within 10 years, and if it was 4.0 ng/ml it would have been 20.1%. If the man would start smoking regularly, he would increase his risk of dying within 10 years to 31.5%. If the man would bring his blood pressure down to 120/80, he would lower his risk of dying within 10 years to 7.7%. If he could decrease his waist by 5 cm, he would lower his risk to 16.7%.

Example 10

SuPAR Levels is a Risk Marker of Future Cancer Development

Aim of Study. Previous studies have shown that suPAR levels are predictive of prognosis in certain types of cancer patients. However, it has never been investigated if suPAR levels are predictive of future development of cancer in apparently healthy individuals without cancer. Thus, we have investigated whether suPAR predicts the development of cancer.

Subjects and methods:

The MONICA 10 cohort: In 1982 to 1984, 4807 individuals aged 30, 40, 50 or 60 years of age selected randomly from the population living in the vicinity of Glostrup University Hospital, Denmark, were invited to participate in a population survey. In 1993 to 1994, 3785 were re-invited and 2656 came and participated in subsequent investigations and gave blood. 2605 plasma samples obtained from June 1993 to December 94 were available for the study. The 2605 participants completed a self-administrative questionnaire. Based on self-reported physical activity, participants were divided into 3 groups: subjects without physical activity (20%), subjects with light physical activity (daily walking, bicycling or less than half an hour sport activity each day (55%), and subjects exercising more than half an hour every day (21%). 4% did not fill out questionnaire concerning exercise. 1091 participants were daily smokers (42%), 106 (4%) reported occasional smoking and 1405 (54%) were non-smokers. Alcohol intake was grouped into two groups based on whether the participants drank more or less than the Danish Health Ministries recommendation (21 alcohol units (1 unit=12 g alcohol) per week for men and 14 for women). Information of cancer was obtained through the Danish National Health Register. BMI was calculated as the weight divided by the squared height ($kg/m^2$). The metabolic syndrome was defined according to the International Diabetes Federation definition as central obesity (waist men/women >94/80 cm) together with at least two of following: elevated serum triglycerides >1.7 mmol/l (150 mg/dl), reduced serum high-density lipoprotein cholesterol (<1.03 mmol/l (40 mg/dl), elevated plasma glucose (>5.6 mmol/1 (100 mg/dl) or elevated BP (systolic BP>130 mmHg or diastolic BP>85 mmHg).

Exercise: Based on self-reported physical activity, the subjects were divided into four groups: 1), subjects without physical activity, 2), subjects with light physical activity (daily walking, frequently bicycling or less than half an hour of sport activity each day), 3), subjects participating in sport activities for more than half an hour each day and 4), professional athletes.

High sensitive CRP determinations (hsCRP): Plasma concentrations was determined using the particle enhanced immunoturbidimetry assay (Roche/Hitachi; Roche Diagnostics, Basel, Switzerland) with a range of 0.1-20 mg/l and lowest detection limit 0.03 mg/l. hsCRP was measured in 2510 samples and the median hsCRP was 1.81 (range 0.12-98.45 mg/ml).

SuPAR measurements: SuPAR was measured using the SuPARnostic™ kit (ViroGates, Copenhagen, Denmark). The kit was developed to measure disease progression in HIV-1 infected individuals. Briefly, the kit comes with catching monoclonal antibody pre-coated plates and a HRP-labelled detection monoclonal antibody which is added to the sample dilution buffer. Then 25 μl of plasma sample is mixed with 225 μl of dilution buffer and 100 μl in duplicates are added to the pre-coated plate and incubated for one hour. Following wash, 50 μl substrate was added for 20 minutes and the reaction stopped with 50 μl 0.5 M $H_2SO_4$. Plates were measured at 450 nM with reference 630 nM. 8 plates per working day (312 samples) were measured. The samples were labelled with a number and the technician was unaware of identity of patient sample. The intra-assay variation was 2.75% and inter-assay variation was 9.17%. 2605 samples were measured. The kit standard curve is validated to measure suPAR levels between 0.6 to 22.0 ng/ml. Three samples gave suPAR levels below (2) or above (1) the validated range of the assay and were excluded from the analysis. Cancer data were obtained from the National Health register by a statistician with no knowledge of the individuals suPAR levels. Cancer was diagnosed using the International Classification of Diseases (ICD)-8 and 10 codes. If ICD code was C500:C509, the diagnosis was set as breast cancer. C340:C349 was set to lung cancer. During the follow-up, 28 developed colorectal, 5 developed neoplasms, 37 developed lung cancer, 4 melanoma, 23 breast cancer, one cervix, 3 endometrium, six ovary, 12 prostate, 9 bladder, 9 leukemia. The MONICA study was approved by the local ethical committee.

Statistics: Kaplan Meier survival analysis was carried out on suPAR quartiles and tested for difference between quartiles using the log rank test. Cox regression analysis was used to determine hazard ratios and independence of suPAR. A p<0.05 was considered significant.

Results: 66 individuals had a cancer diagnosis before blood sampling and were excluded from analysis. During the follow-up, 136 developed cancer.

Figure 14:
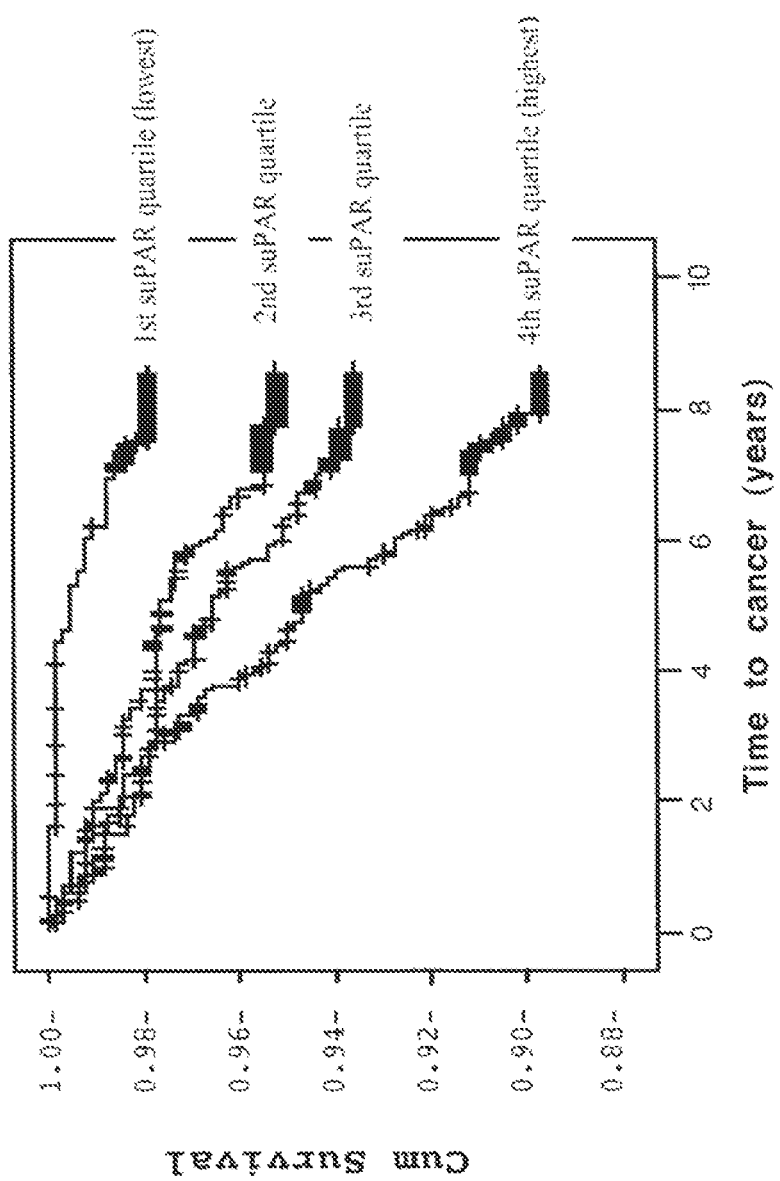
FIG. 14 shows Kaplan Meier analysis of risk of developing cancer over time. The thin upper line represents the lowest suPAR quartile, the one below (median thin line) represents the second lowest suPAR quartile, the medium thick line represents the second highest suPAR quartile and the fattest (bottom line) represents the highest suPAR quartile.

Kaplan Meier analysis on time to cancer diagnosis. The cohort was divided into 4 equally sized groups based on suPAR levels; a low suPAR group (N=650, suPAR range 1.34-3.4 ng/ml), a medium low suPAR group (N=651, range 3.4-4.0), a medium high suPAR group (N=651, range 4.0-4.9) and a high suPAR group (N=650, range 4.9-19.9). Individuals that had a cancer diagnosis were censored from the analysis and a Kaplan Meier analysis on time to cancer diagnosis is shown in FIG. 14 (log rank p<0.001).

Age adjusted Cox regression analysis on time to cancer diagnosis: In order to address whether suPAR was an independent predictor of cancer, multivariate analysis was carried out. In age- and sex adjusted Cox regression analysis, a 1 ng suPAR increase (suPAR ranged between 1.3 and 19.9 ng/ml) was associated with an increased Hazard ratio (HR) of developing cancer of 1.34 (95% Cl: 1.32-1.44%). Univariate (Age adjusted) Cox analysis was carried out for a number of possible predictors of risk of cancer, including sex (P=0.8), diastolic and systolic blood pressure (p=0.5 and 0.3, respectively), metabolic syndrome (p=0.3), diabetes (p=0.9), exercise (p=0.02), smoking (p<0.001), haemoglobin (p=0.9), LDL cholesterol (p=0.14), HDL cholesterol (P=0.4), total cholesterol (P=0.06), triglycerides (P=0.5), fasting glucose level (P=0.5), hsCRP (P=0.4) and BMI (P=0.04). In age-adjusted cox regression multivariate analysis, predictors that were significant or carried a trend in age-adjusted univariate analysis were included. Including suPAR, BMI, Exercise, total cholesterol and smoking, only suPAR and smoking predicted the development of Cancer (Table 15).

Figure 15:
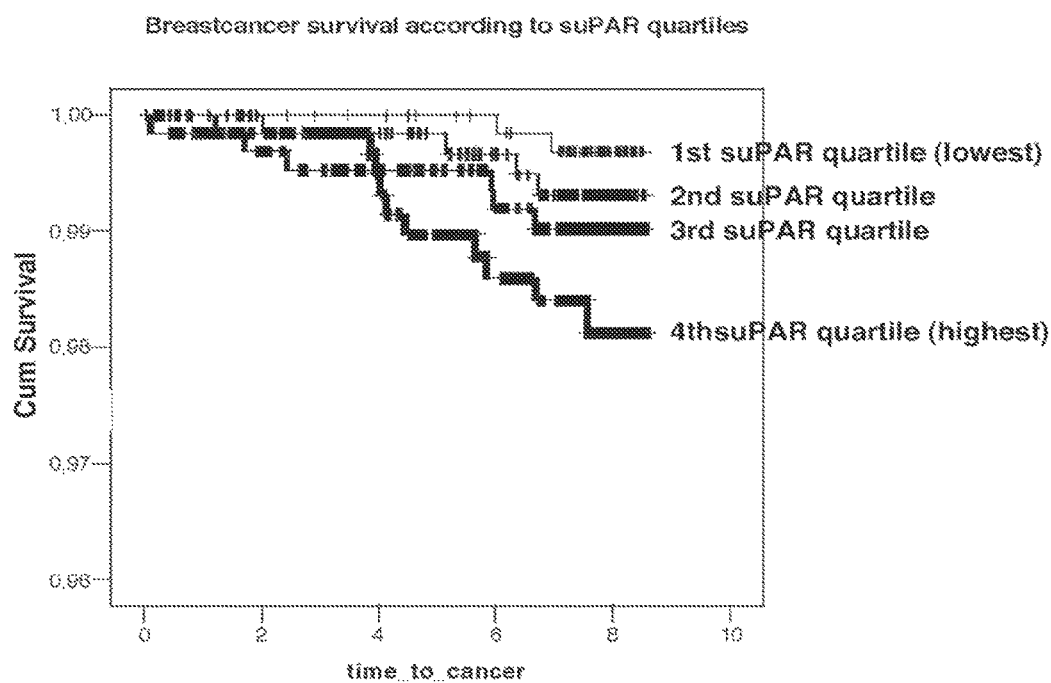
FIG. 15 shows Kaplan Meier analysis of risk of developing breast cancer over time. The thin upper line represents the lowest $1^{st}$ suPAR quartile, the one below (median thin line) represents the second lowest $2^{nd}$ suPAR quartile, the medium thick line represents the second highest $3^{rd}$ suPAR quartile and the fattest (bottom line) represents the highest $4^{th}$ suPAR quartile.

Breast cancer (subgroup analysis). During the follow-up, 22 women developed breast cancer. In univariate analysis, a 1 ng/ml suPAR increase was associated with a RH of 1.37 (95% Cl: 1.15-1.62), p<0.001). Adjusting for age did not alter this increased risk (age adjusted RH=1.35, 95% Cl: 1.13-1.61) for developing breast cancer. Smoking, exercise or lipids were not significantly associated with the future risk of developing breast cancer. Only women developed breast cancer. Kaplan Meier analysis on suPAR quartiles (based on the 2602 individuals and excluding individuals with any form of cancer at baseline) showed that individuals with lowest suPAR (thin line FIG. 15) had significantly less risk of developing breast cancer compared to individuals in the highest suPAR quartile (fattest line FIG. 15).

TABLE 15

| suPAR0123 | Total N | N of Events | Censored | |
| --- | --- | --- | --- | --- |
| | | | N | Percent |
| 0.00 | 642 | 2 | 640 | 99.7% |
| 1.00 | 638 | 6 | 632 | 99.1% |
| 2.00 | 631 | 4 | 627 | 99.4% |

TABLE 15-continued

| suPAR0123 | Total N | N of Events | Censored | |
| --- | --- | --- | --- | --- |
| | | | N | Percent |
| 3.00 | 625 | 10 | 615 | 98.4% |
| Overall | 2536 | 22 | 2514 | 99.1% |

TABLE 16

Overall Comparisons

| | Chi-Square | df | Sig. |
| --- | --- | --- | --- |
| Log Rank (Mantel-Cox) | 5.389 | 1 | 0.020 |

Lung Cancer: During the follow-up, 36 individuals developed lung cancer. In age-adjusted multivariate cox regression analysis, suPAR (RH=1.49, 95% Cl: 1.32-1.69 per ng/ml increase), sex (men had an increased risk of 3.1 (95% Cl: 1.45-6.56) and smoking (daily smokers had an increased risk of 5.16 (95% Cl 2.21-12.04) were significantly associated with the risk of developing lung cancer. When looking at the wald value (Table 17), suPAR was the best variable to explain future development of lung cancer.

Figure 16:
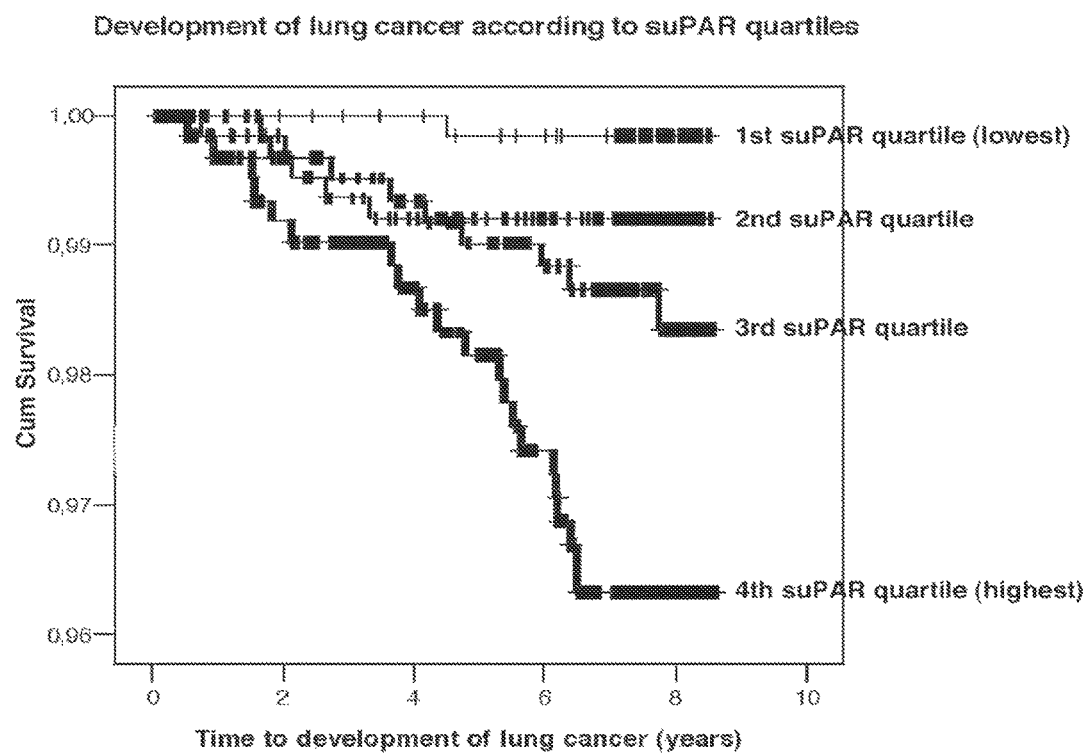
FIG. 16 shows Kaplan Meier analysis of risk of developing lung cancer over time. The thin upper line represents the $1^{st}$ suPAR quartile (lowest), the one below (median thin line) represents the 2nd suPAR quartile (second lowest), the medium thick line represents the $3^{rd}$ suPAR quartile (second highest) and the fattest (bottom line) represents the $4^{th}$ suPAR quartile (highest).

Kaplan Meier analysis on suPAR quartiles (based on the 2602 individuals and excluding individuals with any form of cancer at baseline) showed that individuals with lowest suPAR (thin line FIG. 16 below), median low suPAR (second-thinnest line), median high suPAR (second fattest line) and highest suPAR (fattest line) had significantly different risk of developing lung cancer (p<0.001, log rank test) compared to individuals in the highest suPAR quartile.

TABLE 17

Case Processing Summary

| suPAR0123 | Total N | N of Events | Censored | |
| --- | --- | --- | --- | --- |
| | | | N | Percent |
| .00 | 642 | 1 | 641 | 99.8% |
| 1.00 | 638 | 5 | 633 | 99.2% |
| 2.00 | 631 | 9 | 622 | 98.6% |
| 3.00 | 625 | 21 | 604 | 96.6% |
| Overall | 2536 | 36 | 2500 | 98.6% |

TABLE 18

Overall Comparisons

| | Chi-Square | df | Sig. |
| --- | --- | --- | --- |
| Log Rank (Mantel-Cox) | 25.167 | 1 | .000 |

Figure 17:
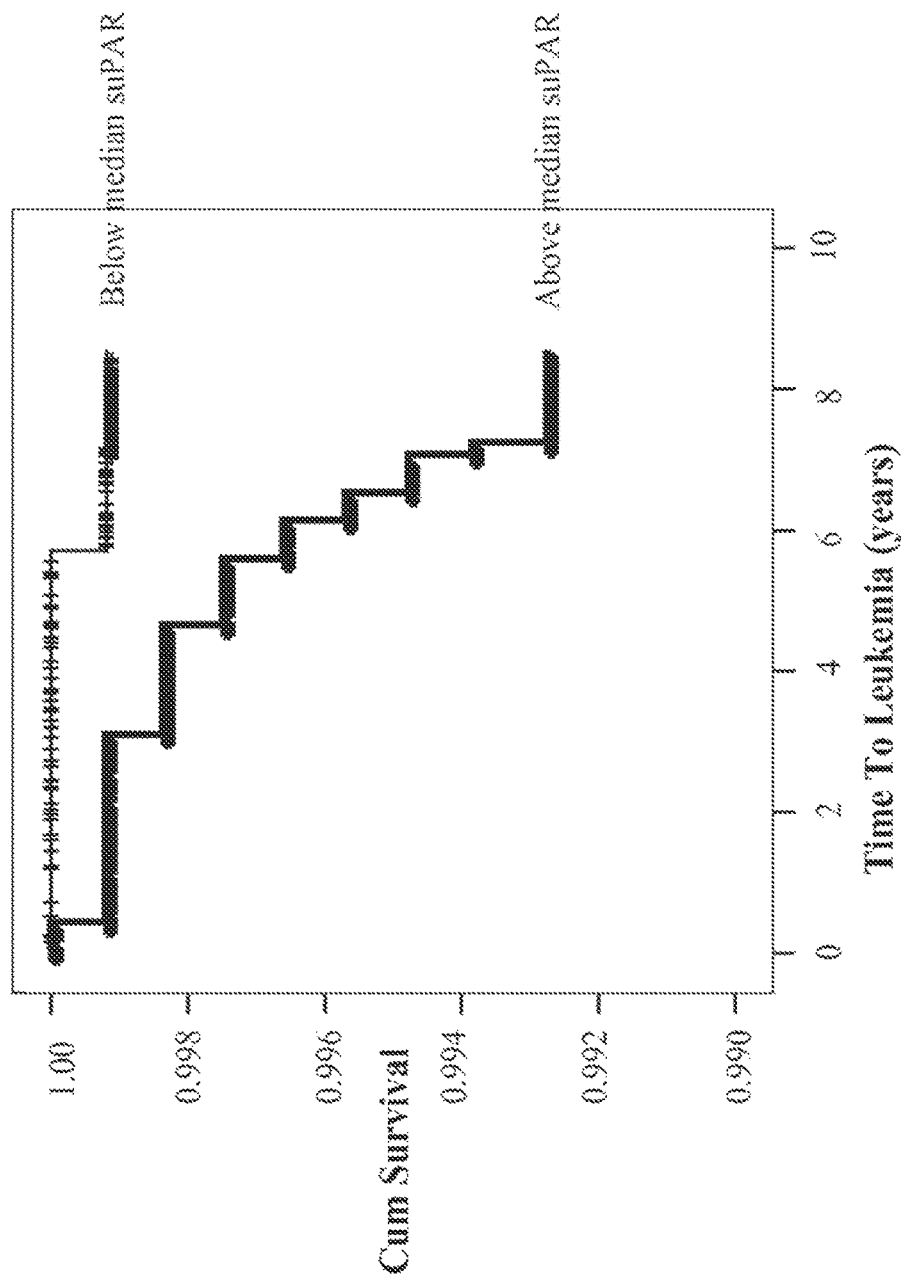
FIG. 17 shows Kaplan Meier analysis of risk of developing leukemia over time. Lower continuous line (with high risk) represents individuals with suPAR above-median, while upper line (dotted line) individuals with suPAR below-median.

Leukemia: During follow-up, 9 individuals developed leukemia. In univariate analysis, suPAR (RH=1.45, 95% Cl: 1.15-1.82 per ng increase) was significantly associated with risk of developing leukaemia. Neither age (RH=1.06, 95% Cl: 0.99-1.14), sex (RH=0.28 for being a man, 95% Cl 0.6-1.2) or smoking (RH=2.85, 95% Cl: 0.7-11.4) was significantly associated with risk of developing leukemia. Due to the small number of events (9 developed leukaemia), Kaplan Meier plot was carried out using median suPAR on the 2602 individuals excluding those who had cancer at baseline (See FIG. 17).

TABLE 19

Leukemia

| suPAR0123 | Total N | N of Events | Censored N | Percent |
|---|---|---|---|---|
| Low suPAR | 642 | 0 | 642 | 100.0% |
| Median low suPAR | 638 | 1 | 637 | 99.8% |
| Median high suPAR | 631 | 2 | 629 | 99.7% |
| High suPAR | 625 | 6 | 619 | 99.0% |
| Overall | 2536 | 9 | 2527 | 99.6% |

TABLE 20

Overall Comparisons

| | Chi-Square | df | Sig. |
|---|---|---|---|
| Log Rank (Mantel-Cox) | 8.882 | 1 | .003 |

Prostate Cancer: During follow-up, 10 individuals developed prostate cancer. SuPAR tended to predict development with a RH of 1.31 per ng suPAR/ml increase (95% CI: 0.98-1.75). Number of events in each suPAR quartile shown below (p=0.12)

TABLE 21

Prostate Cancer

| suPAR0123 | Total N | N of Events | Censored N | Percent |
|---|---|---|---|---|
| .00 | 642 | 1 | 641 | 99.8% |
| 1.00 | 638 | 2 | 636 | 99.7% |
| 2.00 | 631 | 3 | 628 | 99.5% |
| 3.00 | 625 | 4 | 621 | 99.4% |
| Overall | 2536 | 10 | 2526 | 99.6% |

Discussion: The results indicate that suPAR is a highly significant and independent predictor of future risk of developing cancer in individuals who do not have cancer at time of blood sampling. According to the wald-value, suPAR was the strongest predictor of development of overall cancer (see Table 22). Subgroup analysis showed, independent of other predictors, including age, sex and smoking, that increased suPAR levels at baseline increases significantly the risk of developing lung, breast and leukaemia and a trend was observed with regard to prostate-cancer. With regard to minor cancer forms (excluding breast and lung cancer) suPAR was significantly associated with the development of non-lung/non-breast cancer. The minor cancer forms included colorectal, neoplasms, melanoma, cervix, endometrium, ovary, prostate and bladder cancers.

TABLE 22

All Cancers

| | Wald | Sig. | Exp(B) | 95.0% CI for Exp(B) | |
|---|---|---|---|---|---|
| | | | | Lower | Upper |
| SuPAR (ng/ml) | 20.1 | 0.000 | 1.27 | 1.15 | 1.41 |
| sex | 0.1 | 0.825 | 1.04 | 0.73 | 1.48 |
| smoking | 7.7 | 0.006 | 1.70 | 1.17 | 2.48 |
| Total cholesterol | 3.5 | 0.060 | 1.00 | 0.99 | 1.00 |
| Exercise | 3.4 | 0.065 | 0.77 | 0.587 | 1.02 |
| BMI | 2.1 | 0.145 | 0.97 | 0.928 | 1.01 |

TABLE 23

Age-adjusted cox regression multivariate analysis on development of over-all cancer (N = 136)

| | Wald | Sig. | Exp(B) | 95.0% CI for Exp(B) | |
|---|---|---|---|---|---|
| | | | | Lower | Upper |
| SuPAR (per ng/ml increase) | 39.535 | 0.000 | 1.492 | 1.317 | 1.690 |
| AGE (per year older) | 24.377 | 0.000 | 1.098 | 1.058 | 1.140 |
| Sex (men vs. women) | 8.540 | 0.003 | 3.083 | 1.449 | 6.561 |
| Smoking (daily vs non-daily smokers) | 14.385 | 0.000 | 5.157 | 2.209 | 12.038 |

Figure 18:
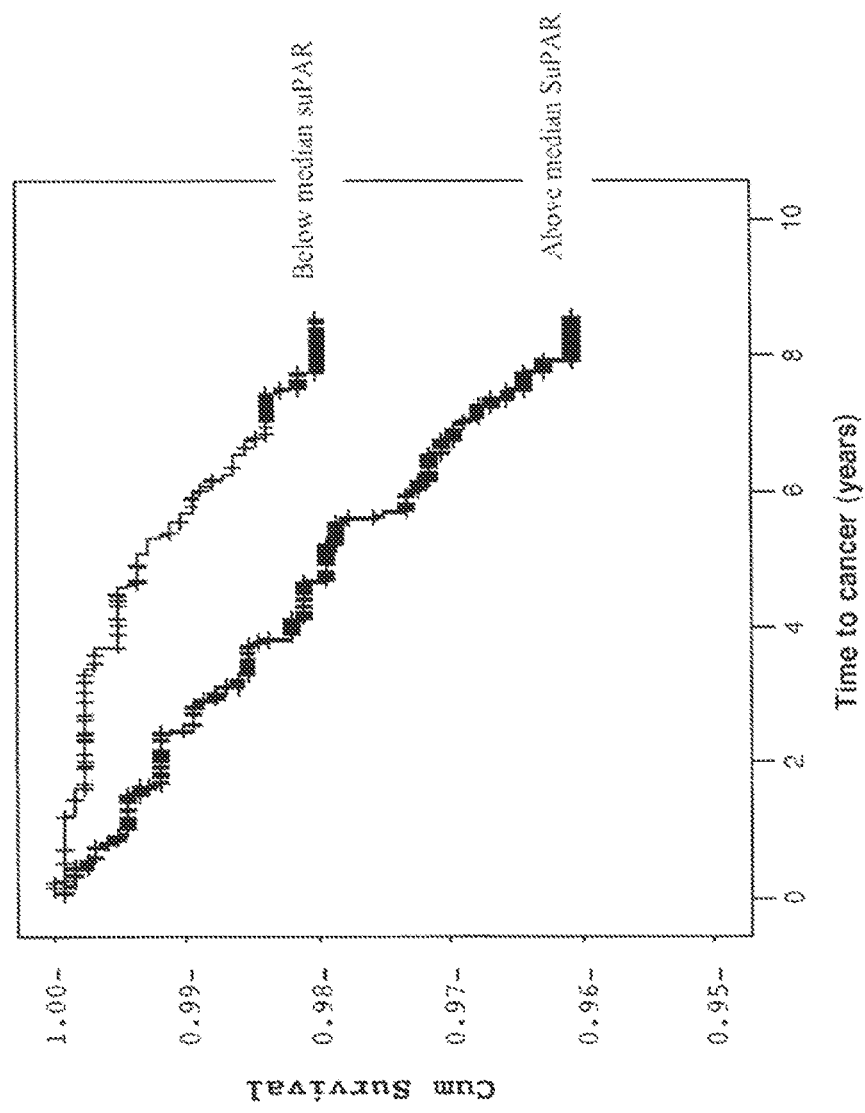
FIG. 18 shows Kaplan Meier analysis of risk of developing cancer, excluding breast or lung cancer, over time. Lower continuous line (with high risk) represents individuals with suPAR above-median, while upper line (dotted line) individuals with suPAR below-median.

As noted above, Kaplan Meier analysis of time to overall-cancer diagnosis is shown in FIG. 14. The thin upper line represents the lowest suPAR quartile, the one below (median thin line) represents the second lowest suPAR quartile, the medium thick line represents the second highest suPAR quartile and the fattest (bottom line) represents the highest suPAR quartile. P<0.001, log rank test. SuPAR and risk of developing non-lung/non-breast cancer When excluding lung and breast cancer, 66 individuals developed other forms of cancer. According to median suPAR levels, those with suPAR above median had significantly higher chance of developing non-lung/non-breast cancer during the follow-up (FIG. 18).

Example 11

Further Studies on the Use of SuPAR, as a Predictor of Cardiovascular Disease and Mortality in Apparently Healthy Individuals Materials And Methods The MONICA 10 cohort: In 1982 to 1984, 4807 individuals aged 30, 40, 50 or 60 years of age selected randomly from the population living in the vicinity of Glostrup University Hospital, Denmark, were invited to participate in a population survey. In 1993 to 1994, 3785 were re-invited and 2656 came and participated in subsequent investigations and gave blood. 2605 plasma samples obtained from June 1993 to December 94 were available for the study. The 2605 participants completed a self-administrative questionnaire.

Based on self-reported physical activity, participants were divided into 4 groups: subjects without physical activity (20%), subjects with light physical activity (daily walking, bicycling or less than half an hour sport activity each day (55%), subjects exercising more than half an hour every day (21%) and professional athletes (N=17). 4% did not fill out questionnaire concerning exercise. 1091 participants were daily smokers (42%), 106 (4%) reported occasional smoking and 1405 (54%) were non-smokers. When entered into the statistical models, occasional smokers were grouped with non-smokers. Alcohol intake was grouped into two groups based on whether the participants drank more or less than the Danish Health Ministries recommendation (21 alcohol units (1 unit=12 g alcohol) per week for men and 14 for women). Information of CVD was obtained in December 2001 through the Danish National Health Register and the data has previously been validated. A composite CVD endpoint of CV death, non-fatal myocardial infarction and non-fatal stroke were used for statistical analysis because prior occurrences of these endpoints were recorded at baseline. Median CVD follow-up time was 7.6 years. During the follow-up, 316 developed CVD of which 291 were non-fatal. Of the 316, 118 developed an IHD of whom 70 were diagnosed with AMI. After a median of 11.0 years of follow-up (December 2005), information on mortality was obtained through the Civil Registration System. During the follow-up, 388 died, and 13 were lost to follow-up. BMI was calculated as the weight divided by the squared height ($kg/m^2$).

Blood pressure was measured sitting after 5 minutes of rest using a mercury sphygmomanometer and the mean of two measurements was reported.

Exercise: Based on self-reported physical activity, the subjects were divided into four groups: 1), subjects without physical activity, 2), subjects with light physical activity (daily walking, frequently bicycling or less than half an hour of sport activity each day), 3), subjects participating in sport activities for more than half an hour each day and 4), professional athletes. The study was approved by the local ethical committee and the subjects gave informed consent.

SuPAR measurements: SuPAR was measured using the SuPARnostic™ kit (ViroGates, Copenhagen, Denmark). The kit was developed to measure disease progression in HIV-1 infected individuals. Briefly, the kit comes with catching monoclonal antibody pre-coated plates and a HRP-labelled detection monoclonal antibody which is added to the sample dilution buffer. Then 25 µl of plasma sample is mixed with 225 µl of dilution buffer and 100 µl in duplicates are added to the pre-coated plate and incubated for one hour. Following wash, 50 µl substrate was added for 20 minutes and the reaction stopped with 50 µl 0.5M $H_2SO_4$. Plates were measured at 450 nM with reference 630 nM. The samples were labelled with a number and the technician was unaware of identity of patient sample. The intra-assay variation was 2.75% and inter-assay variation was 9.17%. 2605 samples were measured. The kit standard curve is validated to measure suPAR levels between 0.6 to 22.0 ng/ml. Three samples gave suPAR levels below (2) or above (1) the validated range of the assay and were excluded from the analysis. There was no correlation between suPAR levels and the date of plasma sampling (samples were obtained between June 1993 and December 1994) indicating the time of sample freezing did not influence on the plasma level of suPAR (rho=0.001, p=0.96).

Statistics: The prognostic significance of suPAR was investigated for two different outcomes. These were the time that passed from the blood sample in 1993-94 until 1) diagnosis of CVD and 2) death. After stratifying suPAR in four groups according to its quartiles, a Kaplan-Meier plot was drawn for the time until death. For the time until CVD, a competing risks analysis was carried out with CVD and death as the competing risks, and the estimate of the time until CVD was drawn. Cox's proportional hazards model was used for the analysis yielding hazard ratios for quantification of effect size. First, the effect of suPAR was estimated in different models, all including age and gender. To investigate whether the effects of suPAR on the outcomes were confounded, three groups of variables, termed Lifestyle, Lipids, and Cardiovascular, were included separately and jointly, and the effect of suPAR was estimated in these models. In the analysis, the following variables were entered as continuous: age, suPAR, total cholesterol, HDL cholesterol, triglycerides, systolic blood pressure, diastolic blood pressure, BMI and waist circumference. The following variables were entered as categorical: gender, smoking (def), exercise (def) and alcohol (def). Second, adjusted for age and gender, hazard ratios are calculated for all other variables.

Using multiple regression analyses, relative hazards were adjusted for age and gender, calculating the standardized regression quotient for lifestyle measures (daily exercise, alcohol consumption and smoking status), lipids (total cholesterol, HDL cholesterol and triglycerides) and metabolic risk factors (Diastolic and systolic blood pressure, BMI, waist).

Results: SuPAR was quantified in 2602 individuals. Median suPAR was 4.03 ng/ml plasma (range 1.3-19.9). SuPAR levels increased with age and were higher among women (N=1292, median suPAR 4.26, range 1.9-19.9) compared to men (N=1310, median suPAR 3.84, range 1.3-17.8), p<0.001.

SuPAR predicts CVD independent of classical cardiovascular markers: At the time of blood sampling, 209 individuals had suffered a cardiovascular event and were excluded from the CVD analysis. During the follow-up, 316 developed a cardiovascular event. In age and sex-adjusted Cox regression analysis, a 1 ng/ml suPAR increase was associated with a 19% increased risk (95% CI: 12-25%) of developing a cardiovascular event. To determine whether suPAR was an independent marker of CVD, the influence of classical cardiovascular risk markers on the hazard ratio (HR) of suPAR was determined (see Table 24).

TABLE 24

The relative hazard per ng suPAR increase adjusted for other risk factors

|  | CVD HR (95% CI) | Mortality HR (95% CI) |
|---|---|---|
| SuPAR | N = 2379 | N = 2602 |
|  | 1.19 (1.12-1.25) | 1.24 (1.19-1.29) |
| Lifestyle | N = 2324 | N = 2537 |
| (Smoking, exercise, alcohol) | 1.15 (1.08-1.22) | 1.21 (1.16-1.27) |
| Lipids | N = 2378 | N = 2601 |
| (Total cholesterol, HDL cholesterol, triglycerides) | 1.19 (1.12-1.25) | 1.24 (1.19-1.29) |
| CVD risk factors | N = 2379 | N = 2602 |
| (Diastolic and systolic blood pressure, BMI, waist) | 1.18 (1.12-1.25) | 1.25 (1.19-1.30) |
| All | N = 2323 | N = 2536 |
|  | 1.13 (1.06-1.22) | 1.22 (1.16-1.28) |

As shown in Table 24, the effect on suPAR remained largely unaltered when including the cardiovascular risk markers and it may be concluded that suPAR is an independent predictor of CVD.

In order to directly compare the predictive values of suPAR and classical risk markers on the future risk of developing CVD, the change of one standard deviation (SD)

were used. As shown in Table 25, suPAR was the second best predictor (after diastolic blood pressure) for the assessment of a future CVD event.

TABLE 25

Hazard ratios of a 1 SD change for risk of developing CVD and mortality.

|  | CVD HR (95% CI) | Total mortality |
|---|---|---|
| suPAR | 1.26 (1.17-1.36) | 1.34 (1.27-1.41) |
| HDL | 0.92 (0.81-1.04) | 0.96 (0.86-1.07) |
| Total cholesterol | 1.07 (0.96-1.20) | 0.95 (0.85-1.05) |
| Triglycerides | 1.10 (1.00-1.21) | 1.03 (0.93-1.15) |
| Systemic blood pressure | 1.07 (0.96-1.20) | 1.15 (1.04-1.28) |
| Diastolic blood pressure | 1.41 (1.26-1.58) | 1.14 (1.03-1.26) |
| Body Mass Index | 1.05 (0.93-1.18) | 0.93 (0.84-1.04) |
| Waist | 1.22 (1.08-1.38) | 1.07 (0.95-1.20) |

SuPAR Levels are Predictive of Longevity

During the 11-year follow-up, 388 died (150 women and 238 men) and 13 were lost to follow-up. When dividing the cohort into quartiles based on suPAR values, a significant difference in survival was observed between all quartiles.

In Cox regression analysis, a 1 ng/ml higher suPAR was associated with a 24% increased risk of mortality during follow-up (95% CI: 19-29%). In multivariate analysis (Table 24), the risk was largely unaltered by the addition of other mortality risk factors. In the direct comparison with other measured and registered variables, a 1 SD change in suPAR was the strongest marker of mortality. To determine whether the effect of suPAR was most pronounced in the early or late stage of life, a subgroup analysis for the four age-groups was carried out. The RH of mortality among 41 year olds was 1.47 (95% CI: 1.30-1.67 per 1 ng/ml suPAR increase), for 51 year olds 1.53 (95% CI: 1.31-1.79), for 61 year olds 1.36 (95% CI: 1.23-1.49), and for 71 year olds 1.12 (95% CI: 1.05-1.20).

SuPAR Levels are Correlated to Lifestyle

Of the 2602 individuals, 1091 were daily smokers, 1511 were non-smokers or non-regular smokers (106 of the 1511). In both men and women, daily smoking was associated with significantly elevated suPAR levels. Non-smoking men (N=730) had a mean suPAR level of 3.72 ng/ml (SD 1.20) which was significantly lower than smoking men (N=580, mean suPAR=4.57, SD 1.45 ng/ml), p<0.001. Similarly, Non-smoking women (N=781) had a mean suPAR of 4.07 (SD 1.13) and smoking women (N=511) of 5.11 (SD 1.38), p<0.001. Among the 1511 non-smokers, 614 reported being previous daily smokers. Previous smokers had significantly lower suPAR levels compared to individuals that continued smoking (4.0 vs 4.8 ng/ml, p<0.001). The risk of CVD was significant among both non-smokers (age and sex-adjusted, RH=1.11 per ng/ml increase (95% CI: 1.01-1.23) and smokers (RH=1.21, 95% CI: 1.10-1.31). With regard to total mortality, the HR among non-smokers was 1.17 (95% CI: 1.10-1.25) and among daily smokers 1.31 (95% CI: 1.21-1.42) per ng suPAR increase.

It was also determined whether uPAR levels were influenced by exercise. Using the Mann Whitney test, it was found that individuals that exercised more than 30 minutes per day had significantly lower suPAR levels than individuals reporting not to exercise, an observation that was significant among the 41 (p<0.001), 51 (p<0.001), and 61 (p=0.01) year olds.

The results indicate that the plasma level of suPAR predicts future cardiovascular disease. The risk increase per ng/ml increase in suPAR was not decreased by adding classical markers of CVD, indicating that suPAR is a novel and independent marker of CVD.

Example 12

From Healthy to Disease, a Composite Analysis

Materials and Methods

The MONICA 10 cohort as described above.

To determine the ability of suPAR to predict the risk of developing a disease (CVD, T2DM, cancer or dying) in healthy individuals, we excluded the 220 individuals who had a previous diagnosed event of CVD, T2DM, or cancer at baseline. In the 2382 remaining individuals, age and sex-adjusted Cox regression analysis, a 1 quartile increase in suPAR was associated with a 59% increased risk of developing the composite endpoint consisting of the diseases CVD, T2D, cancer or death (95% CI: 47-72%, Table 26). After adjustment for other markers, suPAR remained a significant predictor of disease with a HR of 41% (95% CI: 29-57%) (Table 26). Individuals within the highest suPAR quartile were at highest risk of developing disease (P<0.001).

Table 26, below, shows the hazard ratio for inter-quartile range of each variable (except smoking, exercise and alcohol which were entered as grouped variables). The inter-quartile ranges are shown in Table 1. Individuals with history of the disease investigated were excluded from the analysis. All hazard ratios were adjusted for gender and age.

TABLE 26

| Variable | Groups/unit | CVD | Diabetes | Cancer | Mortality | Composite |
|---|---|---|---|---|---|---|
| suPAR | per 1.55 ng/ml | 1.35 (1.23-1.49) | 1.46 (1.20-1.76) | 1.59 (1.39-1.81) | 1.39 (1.31-1.48) | 1.59 (1.46-1.73) |
| Smoking | No | 1 | 1 | 1 | 1 | 1 |
|  | Occasional | 0.89 (0.47-1.69) | 0.58 (0.08-4.34) | 1.99 (0.95-4.16) | 0.86 (0.45-1.62) | 1.02 (0.59-1.76) |
|  | Regular | 1.78 (1.42-2.24) | 0.86 (0.43-1.71) | 2.58 (1.85-3.60) | 2.11 (1.72-2.59) | 2.15 (1.76-2.63) |
| Exercise | Inactive | 1 | Not analyzed* | 1 | 1 | 1 |
|  | Light active | 0.65 (0.49-0.86) | Not analyzed* | 0.72 (0.49-1.05) | 0.56 (0.44-0.71) | 0.36 (0.11-1.16) |
|  | Highly active | 0.51 (0.36-0.73) | Not analyzed* | 0.42 (0.25-0.73) | 0.39 (0.28-0.52) | 0.52 (0.17-1.64) |
|  | Professionals | 0.41 (0.06-2.20) | Not analyzed* | 1.25 (0.91-1.71) | 1.6 (0.5-5.11) | 0.83 (0.26-2.62) |
| Alcohol Intake | Below recommended | 1 | 1 | 1 | 1 | 1 |
|  | Above recommended | 1.48 (1.12-1.95) | 2.25 (1.09-4.65) | 1.22 (0.82-1.83) | 1.63 (1.28-2.08) | 1.52 (1.19-1.93) |
| HDL | Per 0.53 mmol/l | 0.90 (0.77-1.05) | 0.92 (0.18-4.70) | 0.88 (0.71-1.09) | 0.95 (0.83-1.10) | 0.74 (0.46-1.10) |
| Triglycerides | Per 0.83 mmol/l | 1.08 (1.00-1.17) | 1.28 (1.16-1.40) | 1.29 (1.03-1.64) | 1.03 (0.94-1.12) | 1.07 (0.99-1.15) |

TABLE 26-continued

| Variable | Groups/unit | CVD | Diabetes | Cancer | Mortality | Composite |
|---|---|---|---|---|---|---|
| Total cholesterol | per 1.4 mmol/l | 1.10 (0.95-1.26) | 0.89 (0.64-1.24) | 0.77 (0.50-1.20) | 0.94 (0.82-1.07) | 1.03 (0.91-1.16) |
| Systolic blood pressure | | 1.60 (1.39-1.85) | 1.74 (1.28-2.36) | 1.76 (1.19-2.61) | 1.19 (1.04-1.37) | 1.34 (1.18-1.52) |
| Diastolic blood pressure | | 1.32 (1.21-1.44) | 1.85 (1.34-2.56) | 1.96 (1.31-2.93) | 1.12 (1.03-1.21) | 1.26 (1.10-1.44) |
| BMI | Per 5.27 kg/m2 | 1.07 (0.93-1.23) | 2.07 (1.48-2.87) | 0.78 (0.63-0.97) | 0.92 (0.80-1.05) | 0.98 (0.88-1.11) |
| Waist | Per 18 cm | 1.33 (1.11-1.59) | 2.55 (1.61-4.04) | 0.89 (0.68-1.16) | 1.10 (0.93-1.30) | 1.16 (0.99-1.37) |
| Blood glucose | Per 0.6 mmol/l | 1.11 (1.05-1.16) | 8.43 (3.72-19.1) | 1.01 (0.92-1.10) | 1.09 (1.05-1.13) | 1.23 (1.10-1.38) |
| hsCRP | Per 3.17 mg/ml | 1.59 (1.31-1.94) | 1.12 (1.01-1.24) | 1.23 (0.96-1.57) | 1.58 (1.35-1.84) | 1.11 (1.07-1.14) |
| Leucocytes | Per $2.2 \times 10^9$ cells/l | 1.35 (1.17-1.56) | 1.37 (0.98-1.93) | 1.22 (1.03-1.46) | 1.37 (1.23-1.53) | 1.37 (1.24-1.52) |

*Not analysed due to too few endpoints

Example 13

Antibodies for the Quantification of SuPAR in a Sample from an Individual

Figure 19:
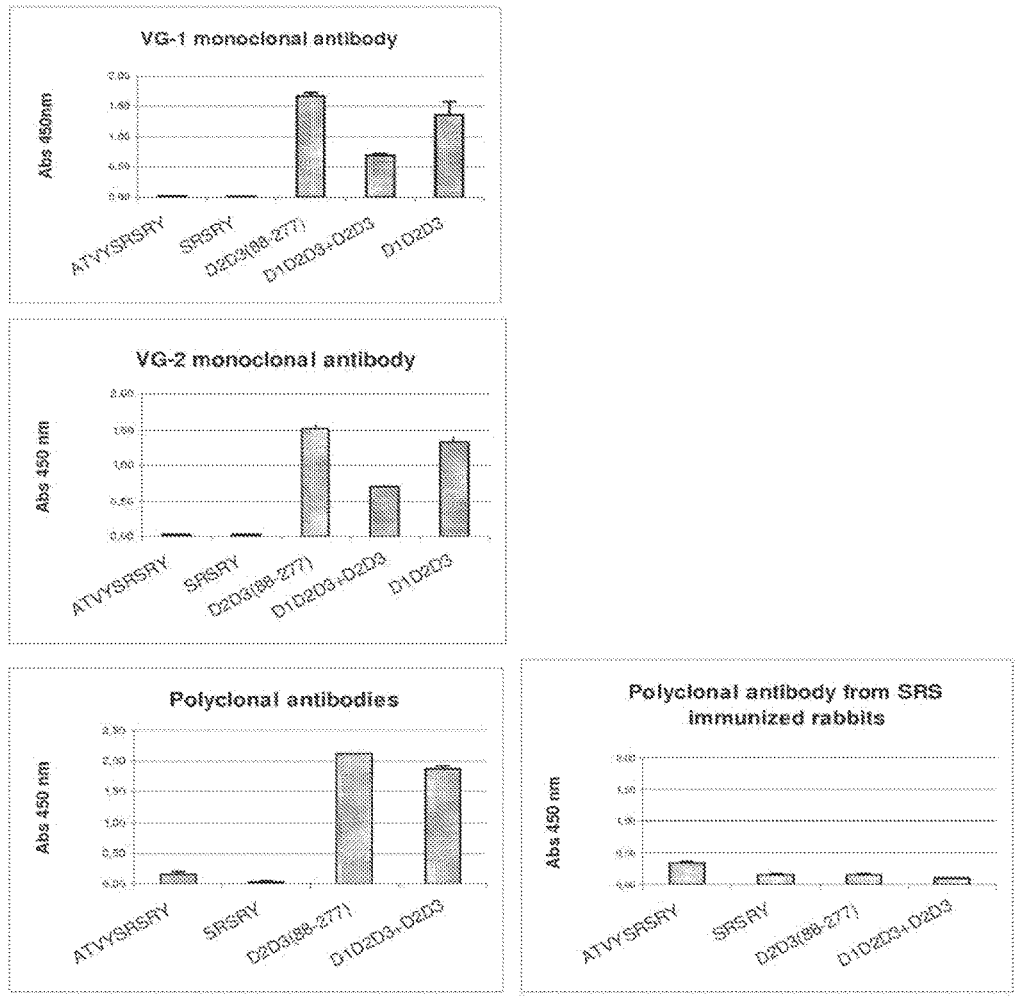
FIG. 19 (Example 13) shows that full length suPAR, $D_1D_2D_{3(1-277)}$, and the chemotactic active suPAR fragment, $D_2D_{3(88-277)}$, were purified by immune-affinity chromatography using antibodies that specifically recognized either $D_1$ (antibodies R3 and R5) or $D_3$ (VG-1 antibody). TAG Copenhagen synthesized the amino acid sequences SRSRY and ATVYSRSRY. A microtiter plate was coated with either purified $D_1D_2D_{3(1-277)}$ (30 ng/ml), purified $D_2D_{3(88-277)}$ (30 ng/ml), SRSRY (50 ng/ml), ATVYSRSRY (50 ng/ml) or a mix of $D_1D_2D_{3(1-277)}$ and $D_2D_{3(88-277)}$ (58 ng/ml). The wells were coated in triplicates and incubated with the antibodies. The antibodies was detected with a horse-radish peroxidase-conjugated goat-anti-mouse antibody, which was developed by the addition of the 3,3',5,5'-tetramethylbenzidine (TMB) substrate and stopped by the application of $H_2SO_4$. An ELISA reader measured the absorbance at 450 nm.
Figure 20:
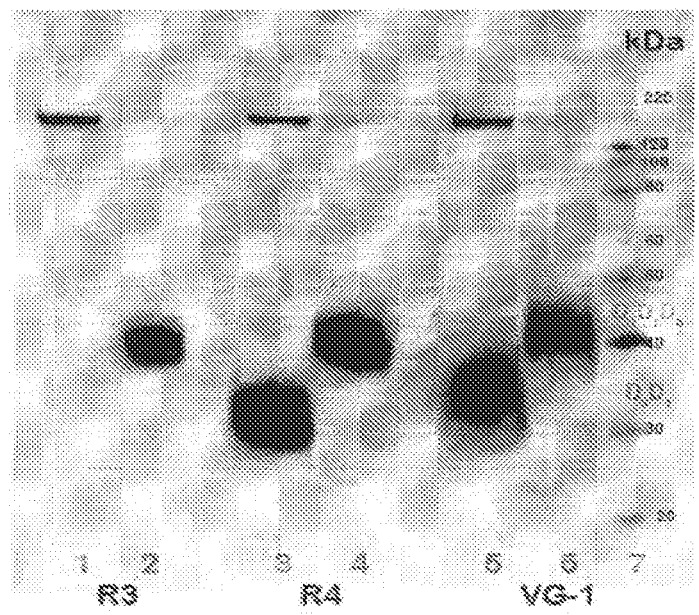
FIG. 20. Purified full length suPAR, $D_1D_2D_{3(1-277)}$ and purified chymotrypsin-cleaved suPAR fragment, $D_2D_{3(88-277)}$ were subjected to immuno-blotting analysis using both the antibodies of the present invention. The VG-1 antibody recognized both full length suPAR, $D_1D_2D_{3(1-277)}$ and the cleaved form, $D_2D_{3(88-277)}$. However, the VG-2 antibody showed not to be applicable for the western blot procedure. $D_1D_2D_{3(1-277)}$ was loaded in lane 2, 4 and 6, while $D_2D_{3(88-277)}$ was loaded in lane 1, 3 and 5. Lane 1 and 2 were incubated with a D1 specific antibody), lane 3 and 4 with a D3 specific antibody) and lane 5, 6 and 7 were incubated with VG-1.

A method for measuring suPAR and suPAR fragments in a biological sample from an individual employs the antibodies (VG-1 and VG-2) having the following characteristics:
- are able to recognize and bind full length suPAR
- are able to recognize and bind the $D_2D_{3(88-277)}$ suPAR fragment obtained by cleavage with chymotrypsin
- do not recognize or bind the chemotactic amino acid sequence SRSRY, which is displayed through cleavage of suPAR with chymotrypsin
- do not recognize or bind the amino acid sequence ATVYSRSRY, which is located from amino acids 84 to 92 in the linker region between $D_1$ and $D_2D_3$ Description of the VG-1 and VG-2 Antibody Specificity The specificity of antibodies used in the ELISA, SuPARnostic® (commercially available from Virogates A/S, Denmark) namely VG-1 (coating antibody) and VG-2 (detection antibody), are shown in FIGS. 19 and 20. These monoclonal antibodies, raised against full length human suPAR in rat (VG-1) and mouse (VG-2), specifically recognize full length suPAR, $D_1D_2D_{3(1-277)}$. The antibodies also specifically recognize the suPAR fragment, $D_2D_{3(88-277)}$, which is obtained by cleavage with chymotrypsin. The antibodies do not recognize the synthesized amino acid sequence SRSRY, which corresponds to the chemotactic active residues 88 to 92 of $D_2D_{3(88-277)}$ that is displayed at the amino-terminal end following cleavage with chymotrypsin (FIG. 19). Neither do the antibodies recognize the synthesized amino acid sequence ATVYSRSRY, which corresponds to the amino-terminal residues 84 to 92 that can be obtained by cleavage with uPA. However, a polyclonal antibody mixture obtained by immunization of rabbits with full length suPAR was able to recognize—though yielding low intensities—the peptide sequence ATVYSRSRY. Furthermore, a polyclonal antibody obtained from rabbits immunized with the SRSRY peptide sequence recognized both the SRSRY and the ATVYSRSRY sequences.

In conclusion, it has been shown that the antibodies (VG-1 and VG-2) both recognize and bind full length suPAR and the suPAR fragment $D_2D_{3(88-277)}$ obtained by cleavage with chymotrypsin. However, the antibodies do not recognize or bind to the chemotactic active sequence SRSRY or the amino-terminal end AVTYSRSRY, which can be obtained by cleavage with uPA.

Antibodies of the VG-1 and VG-2 type are suitable for use in any of the methods of the present invention.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Example 14

SuPAR is an Inducer of Inflammation

Elevated suPAR levels are shown to be diagnostic of a pro-inflammatory condition and to predict the risk of disease. If suPAR induces the pro-inflammatory condition, removal of suPAR e.g. by administrating anti-suPAR antibodies, would lower the inflammation of the individual.

The purpose of the present example was to investigate whether suPAR induces the sub-clinical pro-inflammatory condition or whether it reflects a pro-inflammatory condition. In the present example, purified full-length suPAR ($D1D2D3_{(1-277)}$) as well as the D2D3 fragment of suPAR ($D2D3_{(88-27)}$), was added to freshly drawn human blood and 10 relevant cytokines were measured at different time points following stimulation.

Materials and Methods

An overview of the experimental flow is shown below

Materials and methods

An overview of the experimental flow is shown below

CHO-cell line production of suPAR D1D2D3$_{(1-277)}$
↓
D1D2D3$_{(1-277)}$ purification from cell culture medium by affinity chromatography
↓
Chymotrypsin digestion of D1D2D3$_{(1-277)}$ into D2D3$_{(88-277)}$ and D1$_{(1-87)}$

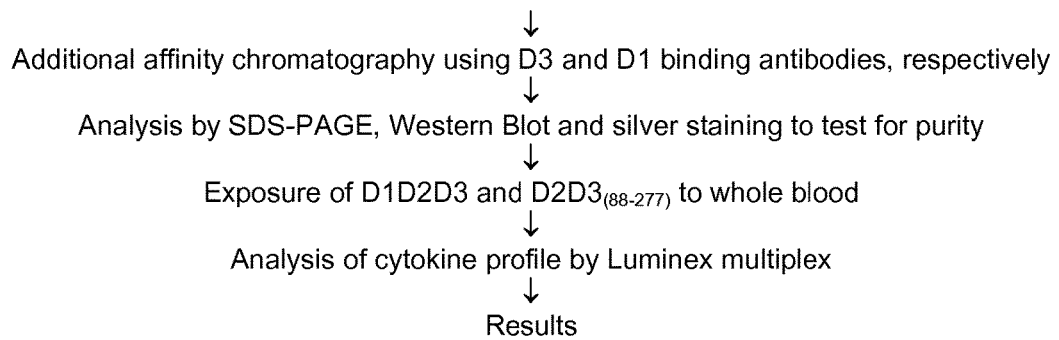

CHO-Cell Line Production of suPAR D1D2D3$_{(1-277)}$

The CHO cell line was stably transfected with recombinant human full length uPAR gene.

The CHO was grown in 90% Dulbecco's Modified Eagle's Medium with GlutaMAX™ I, Sodium Pyruvate (D-MEM, Invitrogen Cat. No. 31966-021) and 10% FBS at 37° C. in a humidified 5% $CO_2$ incubator supplemented with 50 Units/ml penicillin and 50 µg/ml streptamycin (Sigma, Cat No. P4333) and 100 nM methotrexate (MTX, Sigma-Aldrich Cat. No. A6770) as a selective agent ensuring that only stable transfected cells would dominate the population.

D1D2D3$_{(1-277)}$ Purification from Cell Culture Medium by Affinity Chromatography A VG-1 anti-suPAR column (ViroGates, Denmark) was equilibrated with 20 ml PBS before the CHO-cell-line media containing recombinant human suPAR was applied at a volumetric pump rate of 1.5 ml/min. After sample application, the column was washed with 20 ml PBS pH 7.4 to remove unbound proteins and medium components, especially albumin, the most abundant protein in the bovine serum growth supplement. Finally, the suPAR bound by immunoaffinity to VG-1 was eluted with 0.1 M citrate buffer pH 3.0 (Sigma-Aldrich Cat. No. C1909) to break the non-covalent bonds and elute suPAR fragments only. The eluates were collected in 2.5 ml volumes and buffer exchanged into 0.1 M PBS pH 7.4 using the PD-10 columns as previously described and kept either at −20° C. until further analysis.

Figure 21:
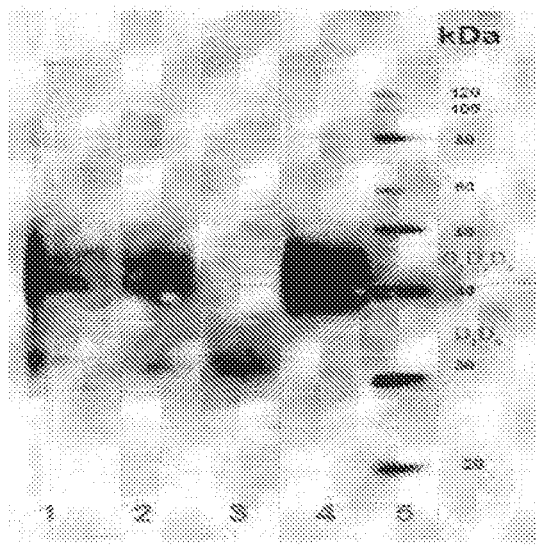
FIG. 21: purified suPAR (4.6 μg/ml) was digested with chymotrypsin in concentrations between 1 and 300 ng/ml for 4 or 24 hours, or analyzed directly without digestion (lane 4), separated in size by SDS-PAGE and then blotted to a PVDF membrane by western blotting. When digesting with 40 ng/ml of chymotrypsin for 4 hours only a small portion of full length suPAR was digested (lane 1). When using 40 ng/ml for 24 hours the suPAR was only partially digested (lane 2). When using 100 ng/ml for 24 hours, completely digested full length suPAR was obtained (lane 3). Magic-Mark was used as a protein ladder (lane 5).

Chymotrypsin Digestion of D1D2D3$_{(1-277)}$ to D2D3$_{(88-277)}$ and D1$_{(1-87)}$ To generate D2D3(88-277) from full length suPAR, the eluates were treated with chymotrypsin (Chymotrypsin sequencing grade Roche Applied Biosciences (Cat. No. 11 418 467 001) which cleaves between the amino acids 87 and 88). 3.5 mL suPAR eluate at a concentration of 9.2 µg/mL suPAR was mixed with 3.5 mL digestion buffer consisting of 0.1% CHAPS and 0.1 M Tris.HCl pH 8.1 giving a final buffer concentration of 0.05% CHAPS and 0.05% Tris-HCl and a final suPAR concentration of 4.6 µg/ml. The solution was aliquoted in eppendorf tubes in volumes of 250 µl and chymotrypsin added to yield the desired final concentration ranging from 1 to 300 ng/mL chymotrypsin. PBS was added to give a final volume of 500 µl. After 4 or 24 hours of incubation at 37° C. the enzymatic reaction was terminated by freezing the relevant sample at −20° C. The resulting products were size separated by SDS-PAGE and then transferred to PVDF membrane by western blotting (FIG. 21).

Additional Affinity Chromatography Using D3 and D1 Binding Antibodies, Respectively Generation of Pure D1D2D3

After the primary affinity purification by the VG-1 column, the eluate was buffer exchanged into a PBS buffer pH 7.4 and applied to a D1 antibody column to remove any $D_2D_3$, giving a pure D1D2D3 eluate. This was buffer exchanged into PBS pH 7.4 and the concentration was determined using the suPARnostic ELISA kit.

Generation of Pure D2D3 SuPAR Fragment

Figure 22:
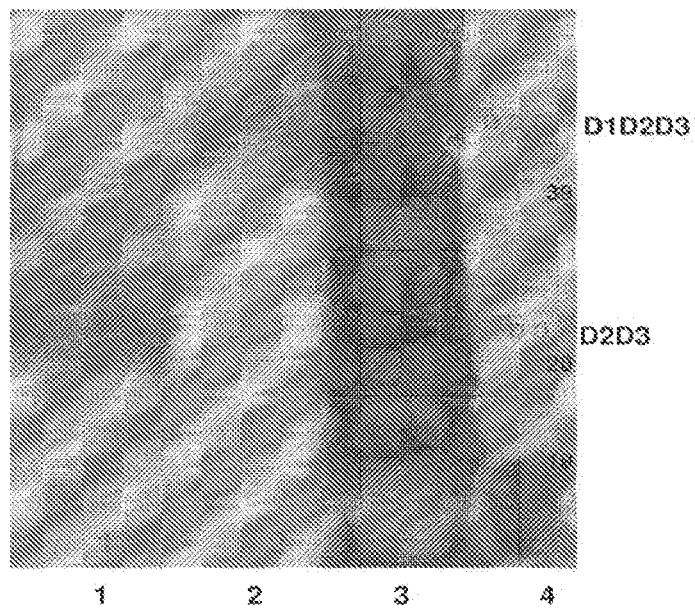
FIG. 22: Silver staining of D2D3(88-277) (lane 1), D1 D2D3 (lane 2), a sample of albumin (lane 3) and SeeBlue (lane 4) following affinity chromatography.

When preparing an eluate consisting of D2D3, the procedure required additional steps. Preceding the primary purification of suPAR, and a buffer exchange into PBS, an enzymatic digestion with chymotrypsin was employed as described above yielding the fragments $D_1$, D2D3 and possibly still some D1D2D3. In order to purify D2D3 from the remaining suPAR fragments, the anti-D1 antibody column was used for negative selection, whereby the flowthrough containing D2D3 and chymotrypsin was collected. This was run through the VG-1 column one more time. Finally, the eluate was buffer exchanged into PBS pH 7.4 and the concentration determined. Purity of the obtained D1D2D3 and D2D3 fragments were visualized using silver staining (FIG. 22) and validated as suPAR molecules using western blotting (FIG. 20) and showed that the correct, pure, compounds had been prepared.

In order to compare and normalize the effects of adding suPAR to blood, the mock sample (negative control) was prepared by adding citrate elution buffer to the column without prior loading of suPAR containing sample and then buffer exchanging the eluate (with no suPAR) into PBS pH 7.4, to mimic the buffer of the suPAR samples. If the elution would cause any bonds to break, either internally in the antibody or between the antibody and the sepharose beads, and contaminate the suPAR eluates, the mock samples would contain the same background as the suPAR eluates Exposure of D1D2D3 and D2D3$_{(88-277)}$ to Whole Blood A 27-year-old healthy female was used as blood donor and no food was ingested 2 hours prior blood sampling in either of the assays. Blood was collected by venipuncture into seven sterile 10 ml lithium-heparin coated tubes (Venoject Li-Heparin tubes, Terumo Cat. No. VT-100SHL), which were to be used for the experiment, and two 4 ml EDTA tubes that were immediately sent for blood data analysis at the Clinical Biochemical Department, Unit 339, Hvidovre Hospital. The concentration of the respective blood cells was determined by enzyme based optical cytometry (employing light scatter) using a Bayer Advia® 120 Hematology Analyzer and the distinction between CD4 and CD8 T-cells by flow cytometry with fluorescence labelled antibodies (Center for Disease Control recommended 4 colour method with gatening on CD45+-lymphocytes. Neutrophil concentration was in the $1^{st}$, $2^{nd}$ and $3^{rd}$ experiment 4.0, 4.3 and $3.1*10^9$ cells/L respectively, eosinophils 0.02, 0.05 and $0.07*10^9$ cells/L, monocytes 0.3, 0.5 and $0.4*10^9$ cells/L and lymphocytes (unspecified) 1.5, 1.7 and $1.9*10^9$ cells/L. Basophil concentration was $0.01*10^9$ cells/L in all the experiments. The overall concentration of leukocytes varied from 5.5, 6.6 to $5.8*10^9$ cells/L.

Analysis of Cytokine Profile by Luminex Multiplex

Plasma was thawed, kept on ice and analyzed following the manufacturer's instructions for the Cytokine 10-plex AB Bead Kit, hu (BioSource™, Invitrogen, Cat. No. LHC0001) or 10-plex Cytokine UltraSensitive™ AB Bead Kit, hu (BioSource™, Invitrogen, Cat. No. LHC6004) on the Luminex® xMAP system (Luminex Corporation) using the software Starstation 2.0 (Applied Cytometry Systems). If intra-assay variation exceeded 20%, the sample was re-measured. Based on the intra-assay variation of the assay, an increase of a markers was considered biologically significant if the analyse in question exceeded the control (mock) by more than 50%.

Results

Three independent experiments were carried out where the whole blood samples were stimulated 5 min, 3 h, 6 h or 24 h with 100 ng/ml D1D2D3$_{(1-277)}$, D2D3$_{(88-277)}$ or with the mock eluate. Samples from each of the experiments were measured in duplicates.

GM-CSF, IL-2, IL-4 and IL-5 were not significantly induced by D1D2D3 or by D2D3. With regard to GM-CSF and IL-5, the obtained results were below the lower limit of quantification. Table 27 show representative results from three independent experiments.

TABLE 27

Cytokine concentrations (pg/ml) of whole blood samples stimulated 5 min, 3 h, 6 h or 24 h with either 100 ng/ml D1D2D3$_{(1-277)}$, D2D3$_{(88-277)}$ or with the mock eluate.

| | \multicolumn{4}{c}{Assay results} | | | |
|---|---|---|---|---|
| | 5 min | 3 h | 6 h | 24 h |
| GM-CSF | | | | |
| Mock (1.) | 0.59 | 0.59 | 0.59 | 0.59 |
| 100 ng/ml D1D2D3 | 0.59 | 0.59 | 0.59 | 0.59 |
| 100 ng/ml D2D3$_{(88-277)}$ | 0.59 | 0.59 | 0.59 | 0.59 |
| IL-2 | | | | |
| Mock (1.) | 0.59 | 0.59 | 0.92 | 3.27 |
| 100 ng/ml D1D2D3 | 0.59 | 0.59 | 0.92 | 3.89 |
| 100 ng/ml D2D3$_{(88-277)}$ | 0.59 | 0.59 | 1.61 | 3.13 |
| IL-4 | | | | |
| Mock (1.) | 1.23 | 1.87 | 4.26 | 8.08 |
| 100 ng/ml D1D2D3 | 1.07 | 2.62 | 4.79 | 12.95 |
| 100 ng/ml D2D3$_{(88-277)}$ | 1.26 | 2.40 | 3.09 | 7.35 |
| IL-5 | | | | |
| Mock (1.) | 0.60 | 0.60 | 0.60 | 0.60 |
| 100 ng/ml D1D2D3 | 0.60 | 0.60 | 0.60 | 0.60 |
| 100 ng/ml D2D3$_{(88-277)}$ | 0.60 | 0.60 | 0.60 | 0.60 |

Figure 23:
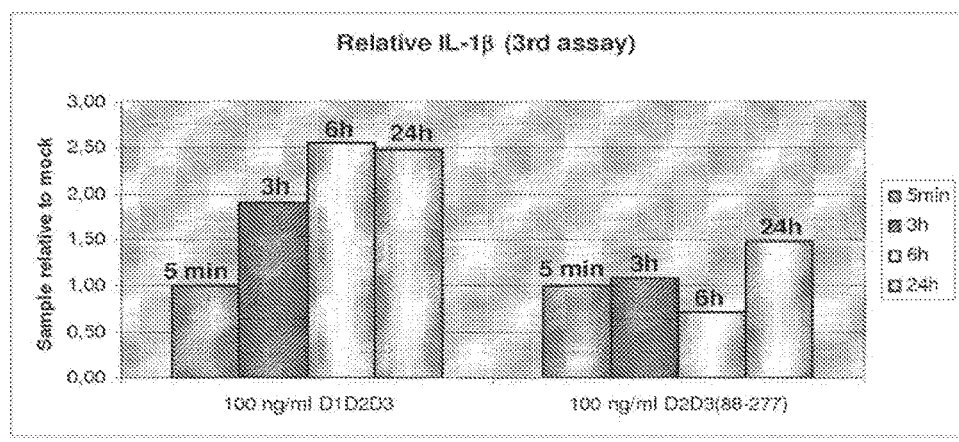
FIG. 23. Graphs of the upregulated cytokines. Relative concentration (The mean of each sample was divided with the mean of the mock samples) in the samples stimulated with 100 ng/ml $D1D2D3_{(1-277)}$ or $D2D3_{(88-277)}$.
Figure 23:
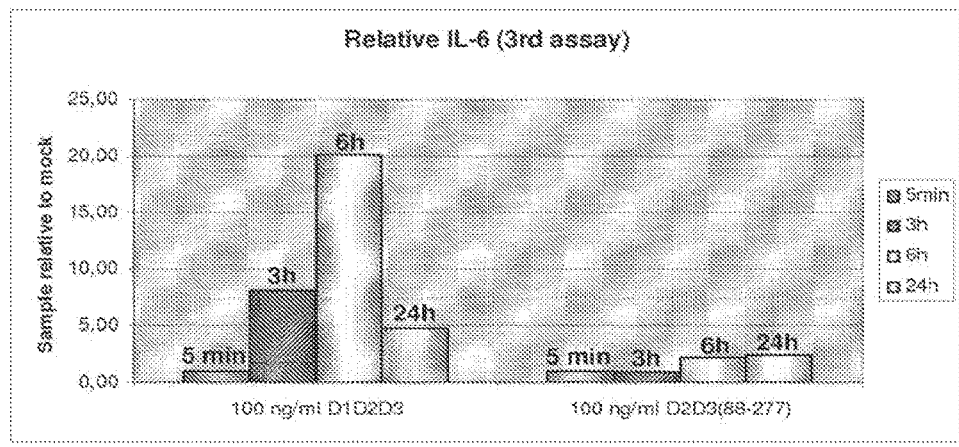
Figure 23:
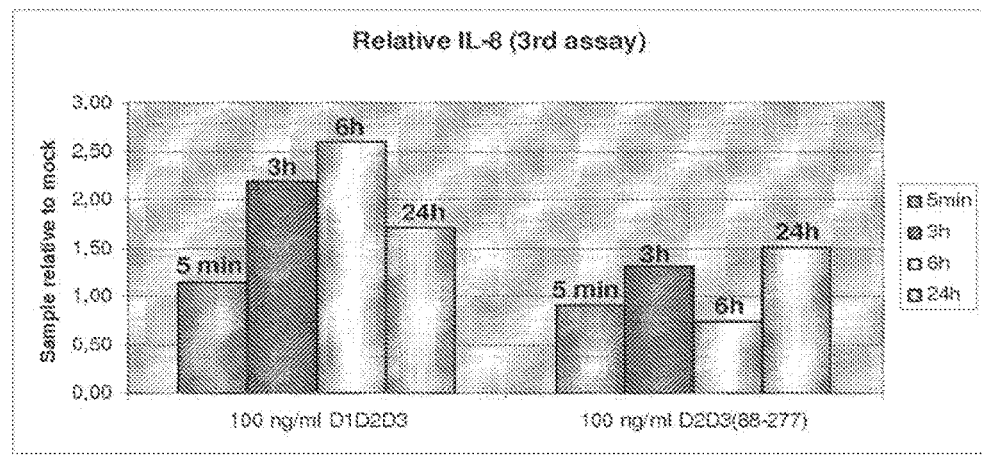
Figure 23:
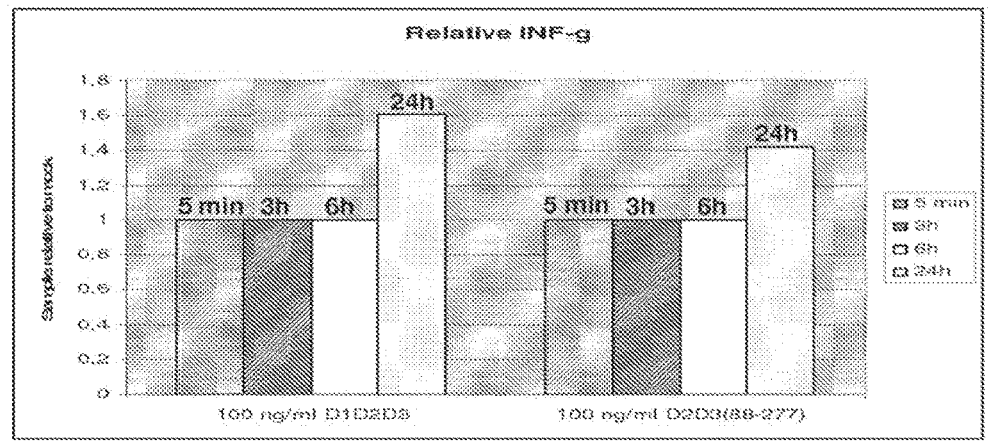
Figure 23:
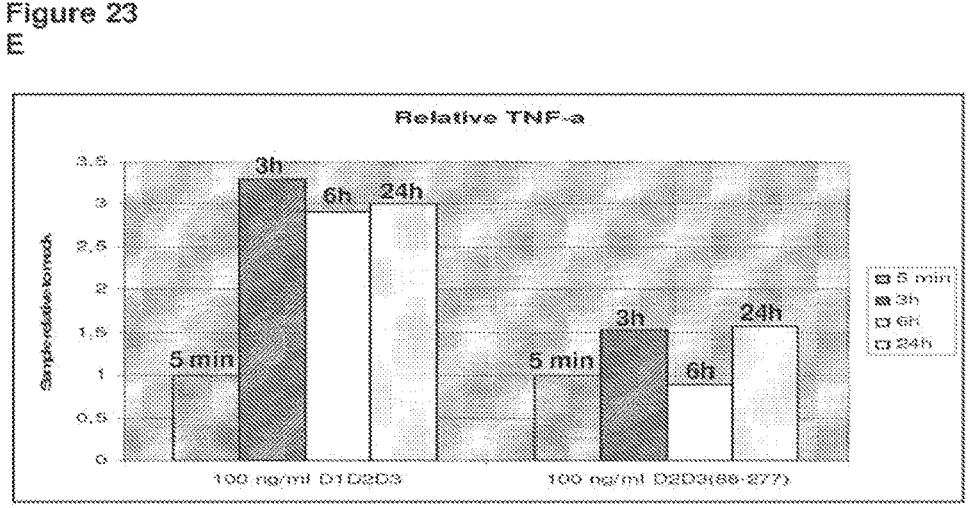
Figure 23:
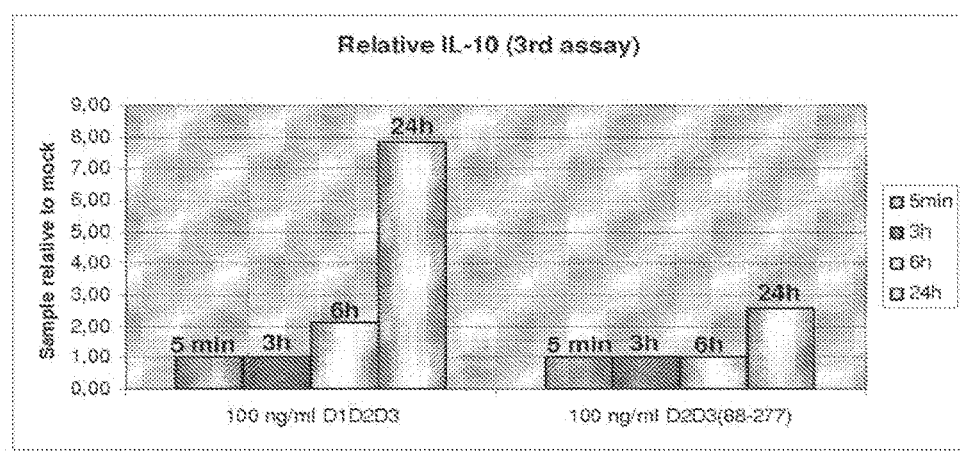

In contrast, the pro-inflammatory cytokines, INF-gamma, IL-1 beta, IL-6, IL-8 and TNF-alfa were up-regulated by $D_1D_2D_{3(1-277)}$ while D2D3 had less effect although TNF-alfa up-regulation was observed (FIG. 23)

CONCLUSIONS

This example showed that full length suPAR is an inducer of certain cytokines as well as the chemokine IL-8. As can been seen in table 28 below, the induction in the early phase (up to 6 hours after stimulation) was observed with regard to IL-1 beta, IL-6, IL-8 and TNF-alfa while no significant upregulation was observed of the other 6 cytokines investigated. The early upregulated cytokines are all pro-inflammatory markers. As often seen when adding a pro-inflammatory marker, the induced effect is counteracted by the late induction (after 24 hours) of IL-10, which was also the case with regard to 24-hour stimulation with D1D2D3.

Based on these results, we conclude that full length suPAR is an active inducer of the inflammatory pathways.

TABLE 28

Schematic overview of the measured cytokines and chemokine (IL-8), source- and target cells and function of cytokines on target cells.

| | Function | Pro- or anti-inflammatory | D2D3 early | D2D3 late | D1D2D3 early | D1D2D3 late |
|---|---|---|---|---|---|---|
| GM-CSF | Inhibits apoptosis of target cells, proliferation and differentiation into granulocytic and macrophage lineages, functional activation of a wide range of cells | Neither | No effect | No effect | No effect | No effect |
| IFN-γ | Up-regulates class I and II MHC expression on macrophages. Activates macrophages, NK and T cells. Ig class switch to IgG2a of activated B cells. Inhibit viral-, bacterial and parasitical replications. | | No effect | No effect | No effect | Up-regulated |
| IL-1β | Induction of other cytokines. Costimulates activation of T cells with IL-2. Activates NK cells. B cell maturation and proliferation. Fibroblast proliferation. Increase expression of adhesion molecules on endothelial cells. Mediator of acute-phase response. Pyrogenic. Induce inflammation. Stimulate hepatocytes to produce acute-phase proteins. | Pro-: participate in the acute-phase response and synergize to mediate inflammation, fever, shock, and death. | No effect | No effect | Up-regulated | Up-regulated |
| IL-2 | Activation, maturation and proliferation of T, B, NK cells, monocytes and macrophages. Stimulates cytolytic activity of activated T cells, large granular lymphocytes and monocytes. Stimulates T cell motility. | | No effect | No effect | No effect | No effect |
| IL-4 | Proliferation and differentiation of B cells. Activation to IgG1 and IgE synthesis. Activation of monocytes. Macrophage up-regulation of | Anti-: reduces endotoxin-induced TNF and IL-I production | No effect | No effect | No effect | No effect |

TABLE 28-continued

Schematic overview of the measured cytokines and chemokine (IL-8), source- and target cells and function of cytokines on target cells.

| | Function | Pro- or anti-inflammatory | D2D3 early | D2D3 late | D1D2D3 early | D1D2D3 late |
|---|---|---|---|---|---|---|
| | MHC Class II. Expansion of Th$_2$ subset. Mast cell development and proliferation. | | | | | |
| IL-5 | Eosinophil activation, differentiation, proliferation and chemotaxis. Basophil activation. Proliferation and differentiation of B cells. IgA synthesis of B cells. | | No effect | No effect | No effect | No effect |
| IL-6 | Proliferation and differentiation of B cells into plasma cells. Antibody production of plasma cells. Differentiation of T cells into cytotoxic T cells. Stimulates production of acute phase response proteins from the liver. Mediates and regulates inflammatory responses. | Pro-: participate in the acute-phase response and synergize to mediate inflammation, shock, and death. Anti-: inhibits TNF production | No effect | No effect | Up-regulated | Up-regulated |
| IL-8 | Chemotactic for neutrophils and macrophages | Pro-: is one of the first cytokines to be released in inflammation | No effect | No effect | Up regulated | Up-regulated |
| IL-10 | Inhibits production of pro-inflammatory cytokines by monocytes, macrophages and mast cells. Inhibits IL-2 production of T cells. Inhibits antigen-specific activation of T cells and production of cytokines. Growth and differentiation factor for B cells. Inhibits monocyte and macrophage MCH class II and costimulatory molecule expression, and NO production. | Anti-: suppresses lymphocyte functions and regulates production of pro-inflammatory cytokines | No effect | Up-regulated | No effect | Up-regulated |
| TNF-α | Mediates host response to Gram-negative bacteria and other infectious agents. Death of tumor cells. CAM and cytokine expression of macrophages. Increase expression of adhesion molecules on endothelial cells. Induce inflammation. | Pro-: participate in the acute-phase response and synergize to mediate inflammation, shock, and death. | No effect | Boarderline Up-regulated | Up-regulated | Up-regulted |

Abbreviations: DC: dendritic cells; NK: natural killer

Various references are cited herein, the disclosures of which are incorporated by reference in their entireties.

---

What is claimed is:

1. A method for determining whether to prescribe prophylactic action for cardiovascular disease, chronic obstructive lung disease, diabetes type 2, asthma bronchiale, or an autoimmune disease in a mammalian subject comprising:
   (a) isolating a sample of blood serum, blood plasma, or urine from a subject;
   (b) measuring the total level of (i) soluble urokinase plasminogen activator receptor (suPAR) and (ii) D2D3 cleavage products of suPAR in said sample of (a);
   (c) comparing the measurement obtained in step (b) with a reference value that is 3 ng/ml blood plasma if the subject is male and 3.5 ng/ml blood plasma if the subject is female, and (d) prescribing the said prophylactic action if the measurement is above the reference value and not prescribing the said prophylactic action if the measurement is at or below the reference value.

2. The method according to claim 1, wherein said method further comprises conducting a glucose tolerance test, assaying TNF-alpha, IL-6, leukocyte count, fasting plasma-glucose or fasting blood-glucose, blood pressure, cholesterol, C-reactive protein and/or triglyceride levels.

3. The method according to claim 1, wherein said prophylactic course of action comprises physical exercise, smoking cessation, lowering of alcohol consumption, or a combination thereof.

4. The method according to claim 1, wherein said subject is apparently healthy.

5. A method of selecting and prophylactically treating a subject for inflammation or a metabolic syndrome-related disease comprising:
(a) measuring the level(s) of soluble urokinase plasminogen activator receptor (suPAR), D2D3 cleavage products of suPAR, or the combination thereof in a blood serum, blood plasma, or urine sample obtained from the subject;
(b) selecting the subject if
  (i) the subject is a male and the level of suPAR, the level of D2D3 cleavage products of suPAR, or the aggregate of suPAR and D2D3 cleavage products of suPAR in the sample is greater than the equivalent of 3 ng/ml in blood plasma, or
  (ii) the subject is a female and the level of suPAR, the level of D2D3 cleavage products of suPAR, or the aggregate of suPAR and D2D3 cleavage products of suPAR in the sample is greater than the equivalent of 3.5 ng/ml in blood plasma;
and;
(c) treating the selected subject by prescribing a prophylactic course of action.

6. The method of claim 5, wherein the prophylactic course of action comprises an increase in the subject's physical exercise, a reduction in the subject's smoking, a reduction in the subject's alcohol consumption, or a combination thereof.

7. The method of claim 5, wherein the inflammation or metabolic syndrome-related disease is selected from the group consisting of cardiovascular disease, chronic obstructive lung disease, diabetes type 2, asthma bronchiale, and an autoimmune disease.

* * * * *